US012790591B2

(12) United States Patent
Zhang et al.

(10) Patent No.: US 12,790,591 B2
(45) Date of Patent: Nov. 10, 2026

(54) EPITHELIAL CELL SPHEROIDS HAVING EXTERIOR APICAL MEMBRANE

(71) Applicant: PROPAGENIX INC., Gaithersburg, MD (US)

(72) Inventors: Chengkang Zhang, Germantown, MD (US); Anura Shrivastava, Arlington, VA (US)

(73) Assignee: PROPAGENIX INC.

( * ) Notice: Subject to any disclaimer, the term of this patent is extended or adjusted under 35 U.S.C. 154(b) by 697 days.

(21) Appl. No.: 17/268,670

(22) PCT Filed: Aug. 14, 2019

(86) PCT No.: PCT/US2019/046493
§ 371 (c)(1),
(2) Date: Feb. 16, 2021

(87) PCT Pub. No.: WO2020/041065
PCT Pub. Date: Feb. 27, 2020

(65) Prior Publication Data

US 2021/0189351 A1 Jun. 24, 2021

Related U.S. Application Data

(60) Provisional application No. 62/726,580, filed on Sep. 4, 2018, provisional application No. 62/720,010, filed on Aug. 20, 2018.

(51) Int. Cl.
*C12N 5/071* (2010.01)
*C12N 5/00* (2006.01)

(52) U.S. Cl.
CPC ......... *C12N 5/0688* (2013.01); *C12N 5/0012* (2013.01); *C12N 2501/11* (2013.01); *C12N 2501/15* (2013.01); *C12N 2501/727* (2013.01); *C12N 2513/00* (2013.01); *C12N 2533/52* (2013.01); *C12N 2533/54* (2013.01); *C12N 2533/74* (2013.01)

(58) Field of Classification Search
CPC ................ C12N 5/0688; C12N 5/0012; C12N 2501/11; C12N 2501/15; C12N 2501/727; C12N 2513/00; C12N 2533/52; C12N 2533/54; C12N 2533/74
See application file for complete search history.

(56) References Cited

U.S. PATENT DOCUMENTS 5,962,324 A * 10/1999 O'Connor ............ C12N 5/0062 435/378
6,692,961 B1 2/2004 Judd et al.
7,199,147 B2 4/2007 Imazaki et al.
7,217,722 B2 5/2007 Takami et al.
8,476,081 B2 7/2013 Kranz et al.
8,895,300 B2 11/2014 Schulz
9,790,471 B2 10/2017 Zhang
9,963,680 B2 5/2018 Zhang
2003/0220357 A1 11/2003 Bankston et al.
2005/0182040 A1 8/2005 Imazaki et al.
2005/0197328 A1 9/2005 Bailey et al.
2006/0241127 A1 10/2006 Feurer et al.
2012/0196312 A1* 8/2012 Sato .................... C12N 5/0677 435/405
2017/0029779 A1 2/2017 Zhang
2017/0029780 A1 2/2017 Zhang
2017/0073635 A1 3/2017 Zhang
2017/0242033 A1 8/2017 Gentzsch et al.
2018/0002669 A1 1/2018 Zhang
2018/0051258 A1 2/2018 Zhang et al.
2018/0208899 A1 7/2018 Zhang
2018/0208900 A1 7/2018 Zhang

FOREIGN PATENT DOCUMENTS

WO 03/059913 A1 7/2003
WO 03/062225 A1 7/2003
WO 03/062227 A1 7/2003
WO 03/064397 A1 8/2003
WO 2004/112719 A2 12/2004
WO 2005/003101 A2 1/2005
WO 2016/161192 A1 10/2016
WO 2017/044454 A1 3/2017
WO 2020/041065 A1 2/2020

OTHER PUBLICATIONS

Yonemura, S., "Differential sensitivity of epithelial cells to extracellular matrix in polarity establishment," PLoS One 9(11): e112922. doi: 10.1371/journal.pone.0112922. Nov. 13, 2014. (Year: 2014).*
Barrila, J., et al., "Organotypic 3D cell culture models: using the rotating wall vessel to study host-pathogen interactions," Nat Rev Microbiol 8(11): 791-801. doi: 10.1038/nrmicro2423. (Year: 2010).*
Massia, S. P., and Hubbell, J. A., "Covalent surface immobilization of Arg-Gly-Asp- and Tyr-Ile-Gly-Ser-Arg-containing peptides to obtain well-defined cell-adhesive substrates," Anal Biochem 187(2): 292-301. doi: 10.1016/0003-2697(90)90459-m. (Year: 1990).*
Altmann, K. H., "The cytoskeleton and its interactions with small molecules," Bioorg Med Chem 22(18): 5038-5039. doi: 10.1016/j.bmc.2014.06.037. (Year: 2014).*
Miyoshi, H., et al., "An improved method for culturing patient-derived colorectal cancer spheroids," Oncotarget 9(31): 21950-21964. doi: 10.18632/oncotarget.25134. Apr. 24, 2018 (Year: 2018).*
StemPro® hESC SFM, Gibco® by Life Technologies™, Publication No. MAN0000744, Rev. 2.00 (Year: 2014).*
Proteintech Group, Cell polarity markers, https://www.ptglab.com/products/featured-products/cell-polarity-markers/ (Year: 2025).*
Kolachala, V. L., et al., "Epithelial-derived fibronectin expression, signaling, and function in intestinal inflammation," J Biol Chem 282(45): 32965-32973. doi: 10.1074/jbc.M704388200. (Year: 2007).*
Conrad, D. R. "Calcium in Cell Culture," Millipore Sigma; Merck KGaA. (Year: 2025).*

(Continued)

*Primary Examiner* — Tracy Vivlemore
*Assistant Examiner* — Eric J Rogers
(74) *Attorney, Agent, or Firm* — Smart & Biggar LP; Micheline Gravelle

(57) ABSTRACT

The technology relates in part to epithelial cell spheroids and methods of producing epithelial cell spheroids.

11 Claims, 15 Drawing Sheets

(56) References Cited

OTHER PUBLICATIONS

Ovsianikov, A., et al., "The Synergy of Scaffold-Based and Scaffold-Free Tissue Engineering Strategies," Trends Biotechnol 36(4): 348-357. doi: 10.1016/j.tibtech.2018.01.005. Epub Feb. 20, 2018. (Year: 2018).*
Hjelm, B. E., et al., "Development and characterization of a three-dimensional organotypic human vaginal epithelial cell model," Biol Reprod 82(3):617-627. doi: 10.1095/biolreprod.109.080408. (Year: 2010).*
Rasouli, M., et al., "Principles of Hanging Drop Method (Spheroid Formation) in Cell Culture," Methods Mol Biol 2879:289-300. doi: 10.1007/7651_2024_527. (Year: 2025).*
Peng, J., et al., Phosphoinositide 3-kinase p110δ promotes lumen formation through the enhancement of apico-basal polarity and basal membrane organization, Nat Commun 6:5937. doi: 10.1038/ncomms6937. (Year: 2015).*
International Preliminary Report on Patentability mailed on Mar. 4, 2021 in International Patent Application No. PCT/US2019/046493, filed on Aug. 14, 2019, 10 pages.
International Search Report and Written Opinion mailed on Nov. 5, 2019 in International Patent Application No. PCT/US2019/046493, filed on Aug. 14, 2019, 17 pages.
Product Information "Product Name: A 83-01", Tocris—A Biotechne Brand, Nov. 23, 2017, 1 page.
Product Information "Product Name: GW 788388", Tocris—A Biotechne Brand, Jan. 14, 2016, 1 page.
Product Information "Product Name: RepSox", Tocris—A Biotechne Brand, Feb. 14, 2019, 1 page.
Product Information "Product Name: SB 431542", Tocris—A Biotechne Brand, Jun. 6, 2019, 1 page.
UniProt Accession No. NM004850, created Jul. 2, 2016.
UniProt Accession No. NM005406, created Aug. 26, 2016.
UniProt Accession No. O75116 replacement for P05777, created Nov. 1, 1988.
UniProt Accession No. Q13464, created May 24, 2004.
Bai et al., "Phenotypic Responses of Differentiated Asthmatic Human Airway Epithelial Cultures to Rhinovirus", PLOS One, Feb. 23, 2015, 10(2):e0118286.
Barkauskas et al., "Lung Organoids: Current Uses and Future Promise", Development, Mar. 15, 2017, 144(6):986-997.
Cao et al., "Evaluating the Toxicity of Cigarette Whole Smoke Solutions in an Air-Liquid-Interface Human In Vitro Airway Tissue Model", Toxicological Sciences, 2017, 156(1):14-24.
Carlson et al., "Three-Dimensional Tissue Models of Normal and Diseased Skin", Current Protocols in Cell Biology, Chapter: Unit—19.9, Dec. 2008, 23 pages.
Chanson et al., "Self-Organization Is a Dynamic and Lineage-Intrinsic Property of Mammary Epithelial Cells", Proceedings of the National Academy of Sciences, Feb. 22, 2011, 108(8):3264-3269.
Co et al., "Controlling Epithelial Polarity: A Human Enteroid Model for Host-Pathogen Interactions", Cell Reports, Feb. 26, 2019, 26(9):2509-2520.
Dekkers et al., "A Functional CFTR Assay Using Primary Cystic Fibrosis Intestinal Organoids", Nature Medicine, Jul. 2013, 19(7):939-945.
Deslee et al., "Bronchial Epithelial Spheroids: An Alternative Culture Model to Investigate Epithelium Inflammation-Mediated COPD", Respiratory Research, Nov. 26, 2007, 8:13 pages.
Fulcher et al., "Well-Differentiated Human Airway Epithelial Cell Cultures", Methods in Molecular Medicine, 2005, 107:183-206.
Gao et al., "Organoid Cultures Derived from Patients with Advanced Prostate Cancer", Cell, Sep. 25, 2014, 159:176-187.
Gerovac et al., "Submersion and Hypoxia Inhibit Ciliated Cell Differentiation in a Notch-Dependent Manner", American Journal of Respiratory Cell and Molecular Biology, Oct. 2014, 51(4):516-525.
Guimbellot et al., "Nasospheroids Permit Measurements of CFTR-Dependent Fluid Transport", JCI Insight, Nov. 16, 2017, 2(22):e95734:11 pages.
Hiatt et al., "Ultra-High Throughput Production of Spheroids with AggreWell™", https://cdn.stemcell.com/media/files/poster/SP00192-Ultra_High_Throughput_Production_of_Spheroids_with_Aggrewell.pdf, Retrieved on Aug. 14, 2018, 1 page.
Hu et al., "Rho Kinase as Potential Therapeutic Target for Cardiovascular Diseases: Opportunities and Challenges", Expert Opinion on Therapeutic Targets, 2005, 9(4):715-736.
Hynds et al., "Concise Review: The Relevance of Human Stem Cell-Derived Organoid Models for Epithelial Translational Medicine", Stem Cells, Mar. 2013, 31(3):417-422.
Jin et al., "Characterization of Primary Human Mammary Epithelial Cells Isolated and Propagated by Conditional Reprogrammed Cell Culture", Oncotarget, XP055634675, 2018, 9(14):11503-11514.
Laurent et al., "Convergence of Microengineering and Cellular Self-Organization Towards Functional Tissue Manufacturing", Nature Biomedical Engineering, XP036428875, Dec. 12, 2017, 1:939-956.
Lee et al., "Air-Liquid Interface Culture of Serially Passaged Human Nasal Epithelial Cell Monolayer for In Vitro Drug Transport Studies", Drug Delivery, 2005, 12:305-311.
Lee et al., "Integrins and Epithelial Cell Polarity", Journal of Cell Science, 2014, 127:3217-3225.
Loirand et al., "Rho Kinases in Cardiovascular Physiology and Pathophysiology", Circulation Research, Feb. 17, 2006, 98(3):322-334.
Lu et al., "Isolation of Circulating Epithelial and Tumor Progenitor Cells with an Invasive Phenotype from Breast Cancer Patients", International Journal of Cancer, Feb. 1, 2010, 126(3):669-683.
Marthin et al., "Patient-Specific Three-Dimensional Explant Spheroids Derived from Human Nasal Airway Epithelium: A Simple Methodological Approach for Ex Vivo Studies of Primary Ciliary Dyskinesia", Cilia, 2017, 6:3:9 pages.
Neuberger et al., "Use of Primary Cultures of Human Bronchial Epithelial Cells Isolated from Cystic Fibrosis Patients for the Pre-Clinical Testing of CFTR Modulators", Methods in Molecular Biology, 2011, 741:39-54.
Okuyama et al., "Dynamic Change of Polarity in Primary Cultured Spheroids of Human Colorectal Adenocarcinoma and Its Role in Metastasis", The American Journal of Pathology, XP055634518, Apr. 2016, 186(4):899-911.
Pedersen et al., "Fluid Absorption Related to Ion Transport in Human Airway Epithelial Spheroids", American Physiological Society, Dec. 1999, 277(6):L1096-L1103.
Pedersen et al., "Ion Transport in Epithelial Spheroids Derived from Human Airway Cells", American Physiological Society, Jan. 1999, 276(1):L75-L80.
Riento et al., "Rocks: Multifunctional Kinases in Cell Behaviour", Nature Reviews Molecular Cell Biology, 2003, 4:446-456.
Sachs et al., "Long-Term Expanding Human Airway Organoids for Disease Modeling", bioRxiv, May 9, 2018, 318444:48 pages.
Sato et al., "Long-term Expansion of Epithelial Organoids from Human Colon, Adenoma, Adenocarcinoma, and Barrett's Epithelium", Gastroenterology, 2011, 141:1762-1772.
Wang et al., "Steps in the Morphogenesis of a Polarized Epithelium. I. Uncoupling the Roles of Cell-Cell and Cell-Substratum Contact in Establishing Plasma Membrane Polarity in Multicellular Epithelial (MDCK) Cysts", Journal of Cell Science, 1990, 95:137-151.
Yonemura Shigenobu, "Differential Sensitivity of Epithelial Cells to Extracellular Matrix in Polarity Establishment", PLOS One, XP055634490, Nov. 2014, 9(11):10 pages.
Yu et al., "Circulating Tumor Cells: Approaches to Isolation and Characterization", Journal of Cell Biology, Feb. 7, 2011, 192(3):373-382.
Zhou et al., "Differentiated Human Airway Organoids to Assess Infectivity of Emerging Influenza Virus", Proceedings of the National Academy of Sciences, www.pnas.org/cgi/doi/10.1073/pnas.1806308115, 2018, 6 pages.
Barrila et al., "Organotypic 3D Cell Culture Models: Using the Rotating Wall Vessel to Study Host-Pathogen Interactions", Nature Reviews Microbiologym, Nov. 1020, vol. 8, pp. 791-801.

(56) References Cited

OTHER PUBLICATIONS

Flood et al., "Free-Floating Epithelial Micro-Tissue Arrays: a Low Cost and Versatile Technique", International Society for Biofabrication, Oct. 10, 2016, pp. 1-15.
Skardal et al., "The Generation of 3-D Tissue Models based on Hyaluronan Hydrogel-Coated Microcarriers within a Rotating Wall Vessel Bioreactor", Biomaterials, Aug. 7, 2010, pp. 8426-8435.
Castillon et al., "Regeneration of a well-differentiated human airway surface epithelium by spheroid and lentivirus vector-transduced airway cells", J. Gene Med., 6, pp. 846-856, Published online Mar. 24, 2004.
Castillon et al., Polarized expression of CFTR and associated epithelial proteins during the regeneration of human airway surface epithelium in three-dimensional culture., Lab. Invest., 82, pp. 989-998, Aug. 1, 2002.

* cited by examiner

EPITHELIAL CELL SPHEROIDS HAVING EXTERIOR APICAL MEMBRANE

RELATED PATENT APPLICATIONS

This patent application is a 35 U.S.C. 371 national phase patent application of PCT/US2019/046493, filed on Aug. 14, 2019, entitled EPITHELIAL CELL SPHEROIDS, naming Chengkang Zhang and Anura Shrivastava as inventors, designated by, which claims the benefit of U.S. provisional patent application No. 62/720,010 filed on Aug. 20, 2018, entitled EPITHELIAL CELL SPHEROIDS, naming Chengkang Zhang and Anura Shrivastava as inventors, and designated by; and claims the benefit of U.S. provisional patent application No. 62/726,580 filed on Sep. 4, 2018, entitled EPITHELIAL CELL SPHEROIDS, naming Chengkang Zhang and Anura Shrivastava as inventors. The entire content of the foregoing applications is incorporated herein by reference, including all text, tables and drawings, for all purposes.

FIELD

The technology relates in part to epithelial cell spheroids and methods of producing epithelial cell spheroids.

BACKGROUND

Organs such as lung, kidney, liver, pancreas and skin can be characterized by, among other things, the presence of epithelia made of organ-specific epithelial cells. Often, epithelial cells are defined by one or more specific functions of each such organ. Specific functions may include, for example, gas exchange in the lung, filtration in the kidney, detoxification and conjugation in the liver, endocrine (e.g., insulin) production in the pancreatic islet cells or protection against hazardous conditions in the environment by the skin.

Epithelial cells may be directly attached to each other by cell-cell junctions, where cytoskeletal filaments are anchored, to form epithelia. Often, epithelia are anchored to other tissue on one side (i.e., the basal side) and generally are free of such attachment on their opposite side (i.e., the apical side). A basal lamina (or basement membrane) lies at the interface with underlying tissue, mediating the attachment. For certain tissues, the apical side of an epithelium generally is exposed to the environment. Access to the apical membrane of an epithelial cell is useful for various biological function studies, e.g., the interaction between infectious agents such as viruses and the epithelial cells.

An air-liquid interface (ALI) culture is an in vitro method currently used for creating an apical-basal polarized epithelial tissue model. Generally, epithelial cells are plated on a porous support in cell culture medium and allow to grow to confluence. The culture medium is then removed from the top side of the porous plastic support to expose the cells to air, which induces the cells to form apical-basal polarized epithelium. The side that is exposed to air becomes the apical side, and the side that is attached to the porous support becomes the basal side. Epithelial cell ALI culture can be a useful in vitro tool for a variety of studies, e.g., safety profile of compound exposure, infectivity of viruses, trans-epithelium drug delivery, and other cellular functions such as water and solute transport across an apical-basal polarized epithelium. A long in vitro maturation/differentiation process (generally a few weeks to over 1 month), a dependence on porous membrane inserts (e.g., 6-, 12-, 24- or 96-well) format, and a lack of suitable methods for cryopreserving mature ALI cultures, however, pose significant challenges for employing ALI culture in high-throughput assays to satisfy increasing demands for a physiologically-relevant assay model.

For certain applications, organoid culture protocols may be used, which can support the formation of apical-basal polarized epithelium in culture. Generally, individual epithelial cells are inoculated into thick extracellular matrix (e.g., Matrigel™), and cultured in medium to form epithelial organoids. The organoids typically are hollow enclosures lined by epithelial cells with the apical side facing inwards (away from the extracellular matrix), and the basal side connected to the extracellular matrix. This format precludes access to the apical side of the cells without penetrating the organoids. Retrieving organoids out of Matrigel™ can be difficult and often depends on the use of a protease, and cryopreservation of organoids is not commonly practiced.

Epithelial bodies (e.g., spheroids) made of epithelial cells having their apical sides facing outwards, readily obtainable from culture media, and amenable to cryopreservation would be useful for a variety of functional studies (e.g., toxicology studies, drug delivery, disease models, infectious agent analysis, and the like), and medical applications such as cell therapy.

SUMMARY

Provided herein in certain aspects are methods for producing a cellular spheroid comprising (a) aggregating a plurality of epithelial cells under aggregation conditions, thereby forming a cellular aggregate, where the epithelial cells comprise an apical membrane and a basal membrane; and (b) culturing the cellular aggregate under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior.

Also provided herein in certain aspects are methods for producing a cellular spheroid comprising (a) aggregating a plurality of epithelial cells under aggregation conditions, thereby forming a cellular aggregate, where the epithelial cells comprise an apical membrane and a basal membrane; and (b) culturing the cellular aggregate under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior; where the aggregation conditions and/or the spheroid-inducing culture conditions comprise one or more transforming growth factor beta (TGF-beta) inhibitors and one or more cytoskeletal structure modulators.

Also provided herein in certain aspects are methods for producing a cellular spheroid comprising (a) attaching one or more epithelial cells to a substrate under substrate attachment conditions, thereby forming a cell-substrate body, where the one or more epithelial cells comprise an apical membrane and a basal membrane; and (b) culturing the cell-substrate body under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior.

Also provided herein in certain aspects are methods for producing a cellular spheroid comprising (a) attaching one or more epithelial cells to a substrate under substrate attachment conditions, thereby forming a cell-substrate body, where the one or more epithelial cells comprise an apical membrane and a basal membrane; and (b) culturing the cell-substrate body under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior; where the substrate attachment conditions and/or the spheroid-inducing culture conditions comprise one or more transforming growth factor beta (TGF-beta) inhibitors and one or more cytoskeletal structure modulators.

Also provided herein in certain aspects are artificial cellular assemblies comprising epithelial cells assembled into a spheroid, where the spheroid comprises an interior and an exterior; each of the epithelial cells comprises an apical membrane and a basal membrane; and for some or all of the epithelial cells in the spheroid, the basal membrane is in the spheroid interior and the apical membrane is on the spheroid exterior.

Also provided herein in certain aspects are cellular spheroids produced by or obtainable by a method comprising (a) aggregating a plurality of epithelial cells under aggregation conditions, thereby forming a cellular aggregate, where the epithelial cells comprise an apical membrane and a basal membrane; and (b) culturing the cellular aggregate under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior.

Also provided herein in certain aspects are cellular spheroids produced by or obtainable by a method comprising (a) aggregating a plurality of epithelial cells under aggregation conditions, thereby forming a cellular aggregate, where the epithelial cells comprise an apical membrane and a basal membrane; and (b) culturing the cellular aggregate under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior; where the aggregation conditions and/or the spheroid-inducing culture conditions comprise one or more transforming growth factor beta (TGF-beta) inhibitors and one or more cytoskeletal structure modulators.

Also provided herein in certain aspects are cellular spheroids produced by or obtainable by a method comprising (a) attaching one or more epithelial cells to a substrate under substrate attachment conditions, thereby forming a cell-substrate body, where the one or more epithelial cells comprise an apical membrane and a basal membrane; and (b) culturing the cell-substrate body under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior.

Also provided herein in certain aspects are cellular spheroids produced by or obtainable by a method comprising (a) attaching one or more epithelial cells to a substrate under substrate attachment conditions, thereby forming a cell-substrate body, where the one or more epithelial cells comprise an apical membrane and a basal membrane; and (b) culturing the cell-substrate body under spheroid-inducing culture conditions, thereby generating a cellular spheroid where (i) the spheroid comprises an interior and an exterior, and (ii) for some or all of the epithelial cells in the spheroid, the basal membrane is in the spheroid interior and the apical membrane is on the spheroid exterior; where the substrate attachment conditions and/or the spheroid-inducing culture conditions comprise one or more transforming growth factor beta (TGF-beta) inhibitors and one or more cytoskeletal structure modulators.

Also provided herein in certain aspects are populations of cellular spheroids, where each spheroid comprises an interior and an exterior; each spheroid comprises epithelial cells, where the epithelial cells comprise primary epithelial cells; each of the epithelial cells comprises an apical membrane and a basal membrane; and for some or all of the epithelial cells in the spheroid, the basal membrane is in the spheroid interior and the apical membrane is on the spheroid exterior; and the population of cellular spheroids is a homogeneous population or a substantially homogeneous population.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 10B represents 50 microns.

FIGS. 11A-110 show antibody staining of ASO (apical side outward-oriented) spheroids made of airway epithelial cells cultured in PneumaCult™-ALI supplemented with A83-01 and Y-27632 (P+A+Y) medium. As shown in FIG. 11A, by day 14, the expanded airway epithelial cells formed ASO spheroids with multiciliated cells (stained with an antibody to acetylated tubulin (Ac Tubilin)) and secretory cells (stained with an antibody to mucin 5AC (MUC5AC). DAPI was used as nuclear counterstain. The size bar in FIG. 11A represents 50 microns.

DETAILED DESCRIPTION

Figure 1:
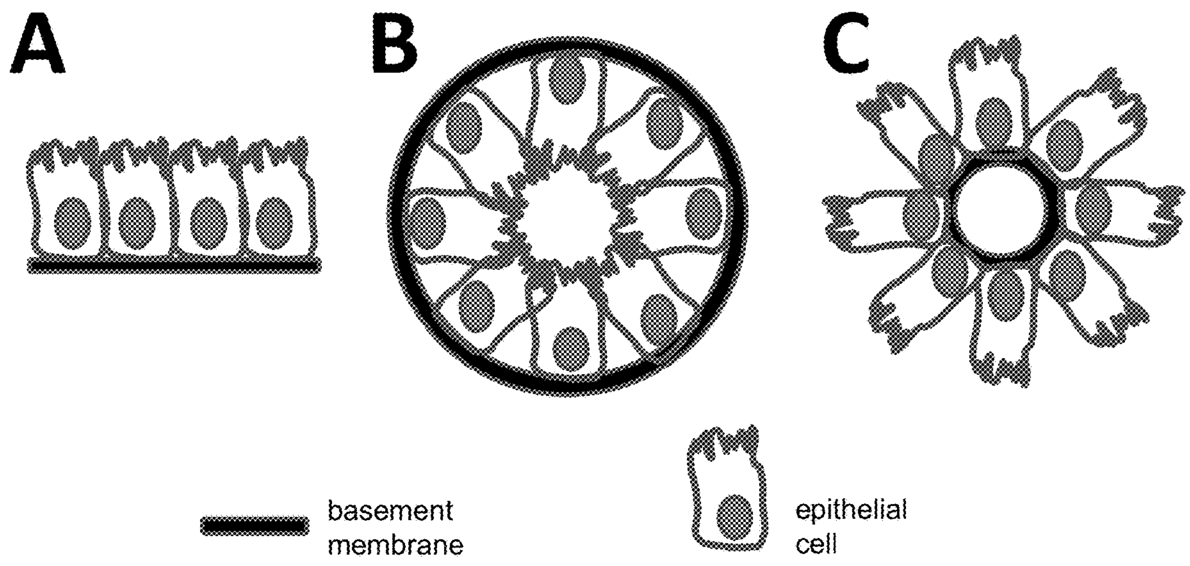
FIG. 1 shows a diagram of different methods that promote the formation of apical-basal polarized epithelium. Panel A shows an air-liquid interface method. Panel B shows an organoid method, in which the epithelial cells are inoculated into thick extracellular matrix and allowed to grow into a hollow spheroid with the apical side facing inwards. Panel C shows an apical side outward-oriented (ASO) epithelial spheroid, in which the epithelial cells are grown on a "core" comprising basement membrane proteins, and the apical side of the spheroid faces outwards.

Provided herein are epithelial cell spheroids and methods of producing epithelial cell spheroids. Epithelial cell spheroids provided herein, and epithelial cell spheroids produced by the methods described herein, may serve as apical-basal polarized epithelial tissue models, and may be useful, for example, for certain in vitro tissue studies and some medical applications. Generally, an epithelial cell spheroid provided herein comprises epithelial cells oriented such that the basal side of each epithelial cell faces the inside of the spheroid and the apical side of each epithelial cell faces the outside of the spheroid. Such spheroids may be referred to herein as apical side outward-oriented (ASO) epithelial spheroids.

Epithelial Cells

Provided herein are spheroids comprising epithelial cells (i.e., epithelial cell spheroids) and methods of producing epithelial cell spheroids. Methods of producing cell spheroids may comprise forming cellular aggregates and/or forming cell-substrate bodies. Accordingly, cell spheroids, cellular aggregates and/or cell-substrate bodies may comprise epithelial cells. An epithelial cell, or epithelium, typically refers to a cell or cells that line hollow organs, as well as those that make up glands and the outer surface of the body. Epithelial cells can comprise squamous epithelial cells, columnar epithelial cells, adenomatous epithelial cells or transitional epithelial cells. Epithelial cells can be arranged in single layers or can be arranged in multiple layers, depending on the organ and location.

Epithelial cells may have cell polarity. For example, certain epithelial cells have an apical-basal polarity. Such cells may comprise an apical membrane on one side and a basal membrane on an opposite side. Such cells also may comprise a lateral membrane. Generally, epithelial cells having an apical-basal polarity comprise an apical membrane on one side and a basal membrane on an opposite side, and an apical membrane located between the apical membrane and the basal membrane.

The basal side of an epithelial cell typically is anchored to other tissue. A basement membrane (or basal lamina) lies at the interface with underlying tissue, mediating the attachment. A basement membrane generally is a thin (e.g., about 100-nm) extracellular matrix (ECM) that contains a meshwork of proteins such as laminins, collagen IV, proteoglycans and nidogen. In certain instances, cell-matrix anchoring junctions tether the basal surface of an epithelial cell to the basement membrane. Cell-matrix anchoring junctions may include hemidesmosomes and actin-linked cell-matrix junctions. Hemidesmosomes generally anchor intermediate filaments in an epithelial cell to extracellular matrix (ECM). Actin-linked cell-matrix junctions generally anchor actin filaments in an epithelial cell to ECM. In certain instances, cells can interact with a basement membrane by binding basement membrane components through cell surface integrin receptors. These interactions allow the basement membrane to provide epithelia with survival, proliferation and differentiation signals, as well as directional cues to establish polarity. An epithelial cell may interact with the extracellular matrix (ECM) through integrin receptors. Cell-matrix interactions typically are involved in creating epithelial cell polarity (see e.g., Lee et al. 2014 J. Cell Sci. 127:3217-3225). The orientation of epithelial polarity typically requires extrinsic signals, which often originate within the ECM. Basal and lateral membranes share certain common protein markers which include, for example, Lethal Giant Larvae (Lgl), Discs Large (Dig), and Scribble (Scrib).

Epithelial cells having an apical-basal polarity generally are free of attachment on the apical side. For certain tissues, the apical side of an epithelial cell is exposed to the environment (e.g., apical side of an airway cell is exposed to inhaled air; apical side of an intestinal cell is exposed to ingested food and liquid). In certain instances, the apical side of an epithelial cell is exposed to the interior or lumen of a tubule or organ (e.g., interior of a renal tubule). For certain epithelial cells, apical membrane is characterized by the presence of cilia and/or microvilli. Cilia generally are found on ciliated epithelial cells, such as epithelial cells in the lungs. Cilia may move by waving rhythmically (e.g., to move debris and/or mucus out). Microvilli generally are found in tissues/organs specialized for absorption, such as the digestive tract or kidneys. Microvilli function by increasing the surface area of the cell membrane, thus allowing for more materials to be absorbed into the cell at a quicker rate. For example, microvilli are found in the small intestine and increase the surface area for nutrient absorption. Protein markers for apical membrane may include, for example, Cdc42, atypical protein kinase C (aPKC), Par6, Par3/Bazooka/ASIP, Crumbs, Stardust, and protein at tight junctions (PATJ).

Epithelial cells may be directly attached to each other at their lateral membranes by cell-cell junctions, where cytoskeletal filaments are anchored, to form epithelia. Cell-cell junctions may include, for example, tight junctions, cell-cell anchoring junctions (e.g., adherens junctions, desmosomes), and channel forming junctions (e.g., gap junctions). Tight junctions generally are parts of cell membranes joined together to seal gaps between epithelial cells and form an impermeable or substantially impermeable barrier to fluid; adherens junctions generally connect actin filament bundles in one cell with that in the next cell; desmosomes generally connect intermediate filaments in one cell to those in the next cell; and gap junctions allow passage of molecules (e.g., small water-soluble molecules) from cell to cell. In the most apical portion of the cell, the relative positions of the junctions are the same or similar in most vertebrate epithelia. A tight junction typically occupies the most apical position, followed by an adherens junction (adhesion belt) and then by a parallel row of desmosomes. Gap junctions and additional desmosomes generally are less regularly organized.

In some embodiments, epithelial cells form tight junctions under certain culture conditions. For example, epithelial cells may form tight junctions under aggregation conditions described herein, under substrate attachment conditions described herein, and/or under spheroid inducing conditions described herein. Formation of tight junctions may be visualized, for example, by immunofluorescence staining of tight junction proteins (e.g., ZO-1). In some embodiments, epithelial cells can be induced to form tight junctions under aggregation conditions. In some embodiments, epithelial cells can be induced to form tight junctions under substrate attachment conditions. In some embodiments, epithelial cells can be induced to form tight junctions under spheroid inducing conditions. For example, epithelial cells can be induced to form tight junctions when exposed to certain concentrations of calcium. In some embodiments, epithelial cells can be induced to form tight junctions when exposed to calcium concentrations that are about 0.5 mM or higher. For example, epithelial cells can be induced to form tight junctions when exposed to calcium concentrations that are about 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2.0 mM, or higher. In some embodiments, epithelial cells can be induced to form tight junctions when exposed to a calcium concentration of about 1.5 mM.

Epithelial cells can comprise keratinocyte epithelial (KE) cells or non-keratinocyte epithelial (NKE) cells. Keratinocytes form the squamous epithelium that is found at anatomic sites such as the skin, ocular surface, oral mucosa, esophagus and cervix. Keratinocytes terminally differentiate into flat, highly keratinized, non-viable cells that help protect against the environment and infection by forming a protective barrier. Examples of keratinocyte epithelial cells include, but are not limited to, dermal keratinocytes, ocular epithelial cells, corneal epithelial cells, oral mucosal epithelial cells, and cervical epithelial cells.

Non-keratinocyte epithelial (NKE) cells form the epithelium of the body such as found in the breast, prostate, liver, respiratory tract, retina and gastrointestinal tract. NKE cells typically differentiate into functional, viable cells which function, for example, in absorption and/or secretion. These cells typically do not form highly keratinized structures characteristic of squamous epithelial cells.

NKE cells described herein can be of any type or tissue of origin. Examples of NKE cells include, but are not limited to, prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, and hair follicle epithelial cells. In some embodiments, epithelial cells comprise airway epithelial cells. In some embodiments, epithelial cells comprise keratinocyte epithelial cells. In some embodiments, epithelial cells comprise prostate epithelial cells. In some embodiments, epithelial cells comprise mammary epithelial cells.

In some embodiments, epithelial cells comprise basal epithelial cells. Basal epithelial cells generally are cells in the deepest layer of stratified epithelium and multilayered epithelium. Basal epithelial cells may be cells whose nuclei locate close to the basal lamina in a pseudostratified epithelium. In some instances, basal epithelial cells may divide (e.g., by asymmetric cell division or symmetric cell division), giving rise to other basal cells and/or other epithelial cell types (e.g., other cell types in a stratified epithelium, multilayered epithelium or pseudostratified epithelium). A proportion of basal epithelial cells in some epithelia may have lifelong self-renew capability and can give rise to other epithelial cell types and basal cells, and sometimes are considered as epithelial stem cells. The proportion of basal epithelial cells that have lifelong self-renew capability and are considered as epithelial stem cells varies among different tissues.

In some embodiments, epithelial cells are isolated. The term isolated generally refers to cells removed from their original environment (e.g., the natural environment if they naturally occurring, or an in vitro cell source (e.g., embryonic stem (ES) cell culture, induced pluripotent stem cell (iPSCs) culture)), and thus are altered "by the hand of man" from their original environment. Epithelial cells may be separated from non-epithelial cells and/or extracellular components (e.g., tissue matrix components) present in a source sample. Isolated epithelial cells may be provided with fewer non-epithelial cells and/or extracellular components (e.g., tissue matrix components) than the amount of non-epithelial cells and/or extracellular components present in a source sample. A composition containing isolated epithelial cells can be substantially isolated (e.g., about 90%, 91%, 92%, 93%, 94%, 95%, 96%, 97%, 98%, 99% or greater than 99% free of non-epithelial cells and/or extracellular components). In some embodiments, a method herein comprises isolating epithelial cells from a subject. In some embodiments, a method herein comprises isolating epithelial cells from tissue from a subject. Epithelial cells isolated from tissue from a subject generally are free of extracellular components from the tissue. Accordingly, in some embodiments, isolated epithelial cells comprise no extracellular components from the tissue from the subject. Generally, extracellular components produced by isolated epithelial cells (e.g., after isolation; during aggregation; during spheroid formation) are not considered as extracellular components from the tissue from the subject.

Epithelial cells may be obtained or isolated from a subject and/or a cellular source. Cells obtained from a subject and/or a cellular source may be referred as an originating epithelial cell population. A cellular source may include epithelial cells from a particular tissue or organ in a subject. A cellular source may include epithelial cells from a sample from a subject. A cellular source may include a population of embryonic stem (ES) cells, induced pluripotent stem cells (iPSCs), and the like. In some embodiments, an originating epithelial cell population is isolated from an embryo or a stem cell culture derived from an embryo. In some embodiments, epithelial cells are isolated from an induced pluripotent stem cell (iPSC) culture. Epithelial cells may be obtained from a subject in a variety of manners (e.g., harvested from living tissue, such as a biopsy, plucked hair follicles, body fluids like urine or body-cavity fluids, or isolated from circulation). A subject may include any animal, including but not limited to any mammal, such as mouse, rat, canine, feline, bovine, equine, porcine, non-human primate and human. In certain embodiments, a subject is a human. In some embodiments, a subject is an embryo. In some embodiments, a subject is an animal or human that has gestated longer than an embryo in a uterine environment and often is a post-natal human or a post-natal animal (e.g., neonatal human, neonatal animal, adult human or adult animal). A subject sometimes is a juvenile animal, juvenile human, adult animal or adult human.

In some embodiments, epithelial cells are isolated from a sample from a subject. A sample can include any specimen that is isolated or obtained from a subject or part thereof. Non-limiting examples of specimens include fluid or tissue from a subject, including, without limitation, blood or a blood product (e.g., serum, plasma, or the like), umbilical cord blood, bone marrow, chorionic amniotic fluid, amnion, cerebrospinal fluid, spinal fluid, lavage fluid (e.g., bronchoalveolar, gastric, peritoneal, ductal, ear, arthroscopic), biopsy sample or tissue biopsy, buccal swab, plucked hair follicles, skin punch biopsy, nasal brushing, celocentesis sample, washings of female reproductive tract, urine, feces, sputum, saliva, nasal mucous, prostate fluid, lavage, semen, lymphatic fluid, bile, tears, sweat, breast milk, breast fluid, hard tissues (e.g., liver, spleen, kidney, lung, or ovary), the like or combinations thereof. The term blood encompasses whole blood, blood product or any fraction of blood, such as serum, plasma, buffy coat, or the like as conventionally defined. Blood plasma refers to the fraction of whole blood resulting from centrifugation of blood treated with anticoagulants. Blood serum refers to the watery portion of fluid remaining after a blood sample has coagulated. In some embodiments, fetal cells are isolated from a maternal sample (e.g., maternal blood, amniotic fluid).

In some embodiments, epithelial cells comprise normal, healthy cells (e.g., cells that are not diseased). In some embodiments, epithelial cells comprise diseased cells. Diseased epithelial cells may include cells from a subject carrying disease-causing mutation(s) (e.g., epithelial cells with genetic mutation(s) in the CFTR gene). Diseased epithelial cells may include cells from abnormal tissue, such as from a neoplasia, a hyperplasia, a malignant tumor or a benign tumor. In certain embodiments, diseased epithelial cells may include cells that are not tumor cells. In certain embodiments, diseased epithelial cells may include cells isolated from circulation (e.g., circulating tumor cells (CTCs)) of a subject. In certain embodiments, diseased epithelial cells may include cells isolated from bodily samples such as, for example, urine, semen, stool (feces), and the like.

In some embodiments, epithelial cells comprise cells that are altered, modified or engineered (e.g., genetically altered, genetically modified, genetically engineered). In some embodiments, epithelial cells are altered, modified or engineered (e.g., genetically altered, genetically modified, genetically engineered). The terms altered, engineered, and modified may be used interchangeably herein in reference to cell, and generally refer to a cell (e.g., epithelial cell) that has been manipulated such that it is distinct (e.g., detectably changed or physically different) from a naturally occurring cell. For example, the sum total of the cellular activities of a modified or engineered cell can be distinct from those of a naturally occurring cell, e.g., a modified cell may include or lack one or more activities relative to the activities present in an unmodified cell utilized as a starting point (e.g., host cell) for modification. In another example, one or more cellular activities of a modified or engineered cell may be altered relative to the cellular activity or activities of the host cell. A modified or engineered cell can be genetically modified through any alteration in its genetic composition. For example, a genetically modified cell can include one or more heterologous polynucleotides, can have one or more endogenous nucleic acid deletions and/or can have one or more genetic mutations. Mutations include point mutations, insertions and deletions of a single or multiple residues in a nucleic acid. In some embodiments, an engineered cell includes a heterologous polynucleotide, and in certain embodiments, an engineered cell has been subjected to selective conditions that alter an activity, or introduce an activity, relative to the host cell. Thus, a modified or engineered cell has been altered directly or indirectly by a human being. It is understood that the terms modified cell and engineered cell refer not only to the particular cell but to the progeny or potential progeny of such a cell. Because certain modifications may occur in succeeding generations due to either mutation or environmental influences, such progeny may not be identical to the parent cell, but are still included within the scope of the term as used herein. In some embodiments, epithelial cells comprise cells that are not genetically altered.

In some embodiments, epithelial cells comprise primary cells. Primary epithelial cells generally are taken directly from living tissue, such as a biopsy, plucked hair follicles, bodily samples such as a stool sample, body fluids like urine, semen or body-cavity fluids, or isolated from circulation. In certain instances, primary cells have not been passaged. In certain instances, primary cells have been passaged one time. Primary cells may be isolated from differentiated tissue (e.g., isolated from epithelium of various organs). Typically, primary cells have been freshly isolated, for example, through tissue digestion and plated. Primary cells may or may not be frozen and then thawed at a later time. In addition, the tissue from which the primary cells are isolated may or may not have been frozen or preserved in some other manner immediately prior to processing. Typically, cells are no longer primary cells after the cells have been passaged more than once. Cells passaged once or more and immediately frozen after passaging are also not considered as primary cells when thawed. In certain embodiments, epithelial cells are initially primary cells and become non-primary cells after passaging. Cells passaged more than once may be referred to as derived from primary epithelial cells. In some embodiments, epithelial cells are maintained or proliferated in cell culture after the cells are isolated from tissue and prior to forming epithelial cell spheroids described herein. In some embodiments, epithelial cells are derived from primary cells.

Cellular spheroids, cellular aggregates, and/or cell-substrate bodies described herein may comprise primary cells. For example, epithelial cells in cellular aggregates may comprise primary epithelial cells. In another example, epithelial cells in cell-substrate bodies may comprise primary epithelial cells. In another example, epithelial cells in cellular spheroids may comprise primary epithelial cells. In some embodiments, cellular spheroids, cellular aggregates, and/or cell-substrate bodies described herein may consist essentially of primary cells. For example, epithelial cells in cellular aggregates may consist essentially of primary epithelial cells. In another example, epithelial cells in cell-substrate bodies may consist essentially of primary epithelial cells. In another example, epithelial cells in cellular spheroids may consist essentially of primary epithelial cells. Cellular aggregates, cell-substrate bodies, and/or cellular spheroids consisting essentially of primary epithelial cells refers to cellular aggregates, cell-substrate bodies, and/or cellular spheroids where at least about 75% of the cells are primary epithelial cells. For example, cellular aggregates, cell-substrate bodies, and/or cellular spheroids consisting essentially of primary epithelial cells may contain at least about 80% primary epithelial cells, at least about 85% primary epithelial cells, at least about 90% primary epithelial cells, at least about 95% primary epithelial cells, at least about 96% primary epithelial cells, at least about 97% primary epithelial cells, at least about 98% primary epithelial cells, or at least about 99% primary epithelial cells. In some embodiments, cellular spheroids, cellular aggregates, and/or cell-substrate bodies described herein may consist of primary cells. For example, epithelial cells in cellular aggregates may consist of primary epithelial cells. In another example, epithelial cells in cell-substrate bodies may consist of primary epithelial cells. In another example, epithelial cells in cellular spheroids may consist of primary epithelial cells.

In some embodiments, primary epithelial cells undergo one or more cell division cycles prior to forming epithelial cell spheroids and/or during cell spheroid formation. For example, primary epithelial cells may divide to form daughter cells, daughter cells may divide to form further daughter cells or further primary cell descendants, and so on. Accordingly, in some embodiments, epithelial cells (e.g., epithelial cells in cellular aggregates, epithelial cells in cell-substrate bodies, epithelial cells in cellular spheroids) comprise primary epithelial cells and/or primary epithelial cell daughter cells and/or primary epithelial cell further daughter cells or further primary cell descendants. In some embodiments, epithelial cells (e.g., epithelial cells in cellular aggregates, epithelial cells in cell-substrate bodies, epithelial cells in cellular spheroids) consist essentially of primary epithelial cells and/or primary epithelial cell daughter cells and/or primary epithelial cell further daughter cells or further primary cell descendants. In some embodiments, epithelial cells (e.g., epithelial cells in cellular aggregates, epithelial cells in cell-substrate bodies, epithelial cells in cellular spheroids) consist of primary epithelial cells and/or primary epithelial cell daughter cells and/or primary epithelial cell further daughter cells or further primary cell descendants.

In some embodiments, epithelial cells comprise non-primary cells, such as cells from an established cell line (e.g., Madin-Darby Canine Kidney (MDCK) cells, immortalized cell line (HeLa cells, HEK 293 cells, immortalized HBE cells), transformed cells, thawed cells from a previously frozen collection and the like. In some embodiments, epithelial cells comprise no non-primary cells. In some embodiments, epithelial cells comprise no cells from an established cell line (e.g., no MDCK cells). In some embodiments, epithelial cells comprise no cells from an immortalized cell line (e.g., no HeLa cells; no HEK 293 cells; no immortalized HBE cells). Non-primary cells may be anchorage independent (i.e., cells that have lost the need for anchorage dependence, which often is essential for cell growth, division, and spreading; cells that have become anchorage-independent are often transformed or have become neoplastic in nature). In some embodiments, epithelial cells comprise no anchorage-independent cells. In some embodiments, epithelial cells comprise anchorage-dependent cells. In some embodiments, epithelial cells consist of comprise anchorage-dependent cells. Anchorage dependence generally refers to the need for cells to be adhered to or in contact with other cells, extracellular matrix, or tissue culture plastic (e.g., via proteins). Often, cells (e.g., primary cells, non-transformed cells) grown in culture require some sort of anchorage for survival. In certain embodiments, epithelial cells comprise secondary cells. In certain embodiments, epithelial cells comprise no secondary cells.

In some embodiments, epithelial cells comprise expanded epithelial cells (e.g., ex-vivo expanded epithelial cells). In some embodiments, epithelial cells are expanded epithelial cells. In some embodiments, epithelial cells are ex-vivo expanded epithelial cells. Epithelial cells may be expanded under any suitable expansion culture conditions, such as, for example, expansion culture conditions described herein. In some embodiments, epithelial cells comprise expanded primary epithelial cells. For example, primary cells may be obtained (e.g., harvested from a subject), expanded, and then subjected to aggregation conditions, substrate attachment conditions, and/or spheroid-inducing culture conditions described herein.

In some embodiments, a culture composition, cellular aggregate, cell-substrate body and/or cellular spheroid comprises a heterogeneous population of epithelial cells (e.g., comprises a mixture of cell types and/or differentiation states such as epithelial stem cells, epithelial progenitors, epithelial precursor cells, lineage-committed epithelial cells, transit-amplifying epithelial cells, differentiating epithelial cells, differentiated epithelial cells, and terminally differentiated epithelial cells) derived from the same tissue or same tissue compartment. In some embodiments, a culture composition, cellular aggregate, cell-substrate body and/or cellular spheroid comprises a homogenous population of epithelial cells (e.g., does not include a mixture of cell types and/or differentiation states) derived from the same tissue or same tissue compartment. In some embodiments, a homogeneous population of epithelial cells comprises at least about 90% epithelial cells that are of the same cell type and/or are present at the same differentiation state. For example, a homogeneous population of epithelial cells may comprise at least about 90%, 91%, 92%, 93%, 94%, 95%, 96%, 97%, 98%, 99% or 100% epithelial cells that are of the same cell type and/or are present at the same differentiation state. In some embodiments, a homogeneous population of epithelial cells comprises about 100% epithelial cells that are of the same cell type and/or are present at the same differentiation state. In some embodiments, epithelial cells are a homogenous population of basal epithelial cells. In some embodiments, an originating epithelial cell population may be heterogeneous or may be homogeneous. In some embodiments, an expanded epithelial cell population may be heterogeneous or may be homogeneous. In some embodiments, an epithelial cell aggregate may be heterogeneous or may be homogeneous. In some embodiments, a cellular aggregate may comprise a heterogeneous epithelial cell population or may comprise homogeneous epithelial cell population. In some embodiments, a cell-substrate body may comprise a heterogeneous epithelial cell population or may comprise homogeneous epithelial cell population. In some embodiments, a cellular spheroid may comprise a heterogeneous epithelial cell population or may comprise homogeneous epithelial cell population. In some embodiments, epithelial cells are characterized by the cell types and/or differentiation states that are included in, or absent from, a population of epithelial cells. In some embodiments, such cell characterization may be applicable to an originating epithelial cell population. In some embodiments, such cell characterization may be applicable to an expanded epithelial cell population. In some embodiments, such cell characterization may be applicable to an originating epithelial cell population and an expanded epithelial cell population. In some embodiments, such cell characterization may be applicable to epithelial cells in a cellular aggregate. In some embodiments, such cell characterization may be applicable to epithelial cells in a cell-substrate body. In some embodiments, such cell characterization may be applicable to epithelial cells in a cellular spheroid. In some embodiments, epithelial cells that include a particular cell type and/or differentiation state comprise at least about 50% epithelial cells that are of the particular cell type and/or differentiation state. In some embodiments, epithelial cells that include a particular cell type and/or differentiation state comprise at least about 90% epithelial cells that are of the particular cell type and/or differentiation state. For example, epithelial cells that include a particular cell type and/or differentiation state may comprise at least about 90%, 91%, 92%, 93%, 94%, 95%, 96%, 97%, 98%, 99% or 100% epithelial cells that are of the particular type and/or differentiation state. Generally, epithelial cells that do not include a particular cell type and/or differentiation state comprise less than about 10% cells that are of the particular cell type and/or differentiation state. For example, epithelial cells that do not include a particular cell type and/or differentiation state may comprise less than about 10%, 9%, 8%, 7%, 6%, 5%, 4%, 3%, 2%, or 1% cells that are of the particular cell type and/or differentiation state.

In certain embodiments, a culture composition, cellular aggregate, cell-substrate body and/or cellular spheroid consists essentially of a population of a particular type of epithelial cell, referred to hereafter as “the majority cells.” Such populations can include a minor amount of one or more other types of epithelial cells, referred to hereafter as “the minority cells.” The minority cells typically are from, or are derived from, the same tissue as the majority cells, and often are from, or are derived from, the same tissue compartment, as the majority cells. The majority cells can be greater than 50%, greater than 60%, greater than 70%, or greater than 80% of the total cells in the composition and often are about 90% or more of the total cells in the composition, and sometimes are about 91%, 92%, 93%, 94%, 95%, 96%, 97%, 98% or 99% or more of the total cells in the composition or population.

In some embodiments, a culture composition, cellular aggregate, cell-substrate body and/or cellular spheroid comprises a heterogeneous population of epithelial cells at different cell cycle phases, such as the M phase, the G1 phase, the S phase, the G2 phase, and the G0 phase which includes senescence and quiescence. In some embodiments, an originating epithelial cell population comprises a heterogeneous population of epithelial cells at different cell cycle phases, such as the M phase, the G1 phase, the S phase, the G2 phase, and the G0 phase which includes senescence and quiescence. In some embodiments, an expanded epithelial cell population comprises a heterogeneous population of epithelial cells at different cell cycle phases, such as the M phase, the G1 phase, the S phase, the G2 phase, and the G0 phase which includes senescence and quiescence. In some embodiments, a cellular aggregate comprises a heterogeneous population of epithelial cells at different cell cycle phases, such as the M phase, the G1 phase, the S phase, the G2 phase, and the G0 phase which includes senescence and quiescence. In some embodiments, a cell-substrate body comprises a heterogeneous population of epithelial cells at different cell cycle phases, such as the M phase, the G1 phase, the S phase, the G2 phase, and the G0 phase which includes senescence and quiescence. In some embodiments, a cellular spheroid comprises a heterogeneous population of epithelial cells at different cell cycle phases, such as the M phase, the G1 phase, the S phase, the G2 phase, and the G0 phase which includes senescence and quiescence. Epithelial cells at a particular cell cycle phase can make up 1% to 100% of the population.

In some embodiments, epithelial cells comprise cells at one or more stages of differentiation. In some embodiments, such stages of differentiation may be described for an originating epithelial cell population. In some embodiments, such stages of differentiation may be described for an expanded epithelial cell population. In some embodiments, such stages of differentiation may be described for an originating epithelial cell population and an expanded epithelial cell population. In some embodiments, such stages of differentiation may be described for epithelial cells in a cellular aggregate. In some embodiments, such stages of differentiation may be described for epithelial cells in a cell-substrate body. In some embodiments, such stages of differentiation may be described for epithelial cells in a cellular spheroid. For example, epithelial cells (or a population of epithelial cells) may comprise epithelial stem cells, epithelial progenitor cells, lineage-restricted epithelial progenitor cells, epithelial precursor cells, lineage-committed epithelial cells, transit-amplifying epithelial cells, proliferating epithelial cells, differentiating epithelial cells, differentiated epithelial cells, quiescent epithelial cells, formerly quiescent epithelial cells, non-proliferating epithelial cells, and terminally differentiated epithelial cells (e.g., cells that are found in tissues and organs). Epithelial cells also may comprise lineage-committed epithelial cells differentiated and/or derived from pluripotent stem cells (embryonic stem (ES) cells or induced pluripotent stem cells (iPSCs)).

In some embodiments, epithelial cells comprise differentiated epithelial cells. Differentiated epithelial cells may divide, but typically do not have the capacity for indefinite self-renewal. In some embodiments, differentiated epithelial cells do not acquire the ability to differentiate into multiple tissue types. Differentiated epithelial cells cultured in conditions described herein generally are more differentiated than undifferentiated cells (e.g., stem cells (embryonic or adult), progenitor cells, precursor cells) and are less differentiated than terminally differentiated cells. Differentiated epithelial cells generally do not include stem cells (embryonic or adult), progenitor cells or precursor cells. In certain instances, differentiated epithelial cells may be referred to as “tissue-specific” and/or “lineage-committed” epithelial cells. In certain instances, differentiated epithelial cells may comprise tissue-specific and/or lineage-committed epithelial cells. In some embodiments, differentiated epithelial cells comprise quiescent epithelial cells. In some embodiments, differentiated epithelial cells comprise basal epithelial cells.

In some embodiments, epithelial cells comprise quiescent or formerly quiescent cells. Quiescent cells generally are non-proliferating cells (i.e., non-cycling cells, cells that have withdrawn from the cell cycle, resting cells), and may be characterized as reversibly growth arrested. Under certain conditions, quiescent cells can be induced to proliferate. Quiescent cells may be characterized as existing in the G0 phase of the cell cycle. Quiescent cells that have been induced to proliferate may be referred to as formerly quiescent cells.

In some embodiments, epithelial cells comprise organ-specific epithelial cells. Organ-specific epithelial cells sometimes are referred to as tissue-specific epithelial cells. In some embodiments, organ-specific epithelial cells may differentiate into more specific cell types within a given organ, but generally do not possess or acquire the ability to differentiate into cells of other types of organs. Organ-specific epithelial cells generally are more differentiated than undifferentiated cells (e.g., stem cells (embryonic or adult)) and are less differentiated than terminally differentiated cells. Organ-specific epithelial cells generally do not include embryonic stem cells. Organ-specific epithelial cells may or may not include adult stem cells (e.g., adult epithelial stem cells), and organ-specific epithelial cells may or may not include progenitor cells or precursor cells.

In some embodiments, epithelial cells comprise lineage-committed epithelial cells. In some embodiments, epithelial cells can comprise lineage-committed epithelial cells differentiated from pluripotent stem cells such as embryonic stem (ES) cells and induced pluripotent stem cells (iPSCs). Lineage-committed epithelial cells may divide, but typically do not have the capacity for indefinite self-renewal. In some embodiments, lineage-committed epithelial cells may differentiate into various cell types within a given cell lineage (e.g., respiratory, digestive or integumentary lineages), but generally do not possess or acquire the ability to differentiate into cells of different cell lineages (e.g., integumentary lineage-committed epithelial cells generally do not differentiate into blood cells). Lineage-committed epithelial cells generally are more differentiated than undifferentiated pluripotent stem cells and are less differentiated than terminally differentiated cells. Lineage-committed epithelial cells generally do not include pluripotent stem cells (embryonic or induced pluripotent). In some embodiments, lineage-committed epithelial cells include progenitor cells or precursor cells. In some embodiments, lineage-committed epithelial cells comprise basal epithelial cells.

In some embodiments, epithelial cells include terminally differentiated epithelial cells. In some embodiments, epithelial cells do not include terminally differentiated epithelial cells. Terminally differentiated epithelial cells generally do not divide and are committed to a particular function. Terminally differentiated epithelial cells generally are characterized by definitive withdrawal from the cell cycle and typically cannot be induced to proliferate. In some embodiments, epithelial cells do not include post-mitotic cells. Post-mitotic cells generally are incapable of or no longer capable of cell division. In some embodiments, epithelial cells do not include senescent cells.

In some embodiments, epithelial cells include embryonic stem cells. In some embodiments, epithelial cells do not include embryonic stem cells. In some embodiments, epithelial cells are differentiated and/or derived from embryonic stem cells. In some embodiments, epithelial cells are not derived from embryonic stem cells. Generally, embryonic stem cells are undifferentiated cells that have the capacity to regenerate or self-renew indefinitely. Embryonic stem cells sometimes are considered pluripotent (i.e., can differentiate into many or all cell types of an adult organism) and sometimes are considered totipotent (i.e., can differentiate into all cell types, including the placental tissue).

In some embodiments, epithelial cells include induced pluripotent stem cells (iPSCs). In some embodiments, epithelial cells do not include induced pluripotent stem cells (iPSCs). In some embodiments, epithelial cells are differentiated and/or derived from induced pluripotent stem cells (iPSCs). In some embodiments, epithelial cells are not derived from induced pluripotent stem cells (iPSCs). Generally, induced pluripotent stem cells (iPSCs) are a type of pluripotent stem cell that can be generated directly from adult cells. In some embodiments, epithelial cells include pluripotent cells. In some embodiments, epithelial cells do not include pluripotent cells. In some embodiments, epithelial cells include totipotent cells. In some embodiments, epithelial cells do not include totipotent cells.

In some embodiments, epithelial cells include adult stem cells. Adult stem cells typically are less differentiated than differentiated cells, organ-specific cells or lineage-committed cells and are more differentiated than embryonic stem cells. Adult stem cells may be referred to as stem cells, undifferentiated stem cells, precursor cells and/or progenitor cells, and are not considered embryonic stem cells as adult stem cells are not isolated from an embryo. Adult epithelial stem cells may be referred to as epithelial stem cells, undifferentiated epithelial stem cells, epithelial precursor cells and/or epithelial progenitor cells. In some embodiments, epithelial cells do not include adult stem cells or cells derived from adult stem cells. In some embodiments, epithelial cells do not include epithelial stem cells or cells derived from epithelial stem cells. In some embodiments, epithelial cells do not include pluripotent epithelial stem cells or cells derived from pluripotent epithelial stem cells. In some embodiments, epithelial cells do not include progenitor cells or cells derived from progenitor cells. In some embodiments, epithelial cells do not include precursor cells or cells derived from precursor cells. In some embodiments, epithelial cells do not include continuously proliferating (e.g., continuously proliferating in vivo) epithelial stem cells (e.g., intestinal crypt cells; Lgr5+ cells) or cells derived from continuously proliferating epithelial stem cells.

Cellular spheroids, cellular aggregates, and/or cell-substrate bodies described herein may comprise stem cells. Cellular spheroids, cellular aggregates, and/or cell-substrate bodies described herein may be derived from stem cells. Cellular spheroids, cellular aggregates, and/or cell-substrate bodies described herein may comprise adult stem cells. Cellular spheroids, cellular aggregates, and/or cell-substrate bodies described herein may be derived from adult stem cells. Cellular spheroids, cellular aggregates, and/or cell-substrate bodies described herein may comprise progenitor cells. Cellular spheroids, cellular aggregates, and/or cell-substrate bodies described herein may be derived from progenitor cells. In some embodiments, cellular spheroids, cellular aggregates, and/or cell-substrate bodies described herein are derived from a homogenous population of cultured stem cells. In some embodiments, cellular spheroids, cellular aggregates, and/or cell-substrate bodies described herein are derived from a homogenous population of cultured adult stem cells. In some embodiments, cellular spheroids, cellular aggregates, and/or cell-substrate bodies described herein are derived from a homogenous population of cultured progenitor cells. In some embodiments, cellular spheroids, cellular aggregates, and/or cell-substrate bodies described herein are derived from a population of epithelial cells comprising no terminally differentiated cells. In some embodiments, cellular spheroids, cellular aggregates, and/or cell-substrate bodies described herein are derived from a homogenous population of cultured airway stem cells and/or airway progenitor cells. In some embodiments, cellular spheroids, cellular aggregates, and/or cell-substrate bodies described herein are derived from a population of epithelial cells comprising no terminally differentiated airway cells. In some embodiments, epithelial cells may be characterized by whether the cells possess one or more markers (e.g., cell surface markers, mRNAs, proteins, epigenetic signatures) and/or do not possess measurable levels of, or possess low levels of, certain markers. In some embodiments, such marker characterization may be applicable to an originating epithelial cell population. In some embodiments, such marker characterization may be applicable to an expanded epithelial cell population. In some embodiments, such marker characterization may be applicable to an originating epithelial cell population and an expanded epithelial cell population. In some embodiments, such marker characterization may be applicable to a cellular aggregate. In some embodiments, such marker characterization may be applicable to a cell-substrate body. In some embodiments, such marker characterization may be applicable to a cellular spheroid.

Cellular Aggregates

Provided herein are methods for producing cellular spheroids. In some embodiments, a method includes forming cellular aggregates. Generally, cellular aggregates are formed prior to producing cellular spheroids. Cellular aggregates may be formed by aggregating a plurality of cells (e.g., epithelial cells) under aggregation conditions. A plurality of cells may comprise one cell capable of dividing, or in the process of dividing, into two cells. A plurality of cells may comprise two or more cells. In some embodiments, a plurality of cells comprises between about 10 cells to about 10,000 cells. For example, a plurality of cells may comprise about 10 cells, about 20 cells, about 30 cells, about 40 cells, about 50 cells, about 60 cells, about 70 cells, about 80 cells, about 90 cells, about 100 cells, about 110 cells, about 120 cells, about 130 cells, about 140 cells, about 150 cells, about 160 cells, about 170 cells, about 180 cells, about 190 cells, about 200 cells, about 300 cells, about 400 cells, about 500 cells, about 600 cells, about 700 cells, about 800 cells, about 900 cells, about 1000 cells, about 2000 cells, about 3000 cells, about 4000 cells, about 5000 cells, about 6000 cells, about 7000 cells, about 8000 cells, about 9000 cells, or about 10,000 cells. In some embodiments, a plurality of cells comprises about 200 cells. In some embodiments, a plurality of cells comprises about 150 cells. In some embodiments, a plurality of cells comprises about 100 cells. In some embodiments, a plurality of cells comprises about 50 cells. A plurality of cells may comprise fewer than 1 million cells. For example, a plurality of cells may comprise fewer than 500,000 cells, fewer than 400,000 cells, fewer than 300,000 cells, fewer than 200,000 cells, fewer than 100,000 cells, fewer than 50,000 cells, fewer than 20,000 cells, fewer than 10,000 cells, or fewer than 1,000 cells.

In some embodiments, aggregates are formed by aggregating between about 50 to 200 cells (e.g., epithelial cells) under aggregation conditions. In some embodiments, aggregates are formed by aggregating more than 200 cells (e.g., epithelial cells) under aggregation conditions. Cells may expand (i.e., divide) under aggregation conditions, and cells may expand after being removed from aggregation conditions (e.g., when placed under expansion conditions and/or when placed under spheroid-inducing conditions, as described herein). In some embodiments, smaller aggregates (e.g., 50-200 cells) may require culture under expansion/spheroid inducing conditions for a period of time before spheroid formation. For example, smaller aggregates (e.g., 50-200 cells) may require culture under expansion/spheroid inducing conditions for about 10-25 days before spheroids begin to form. In some embodiments, larger aggregates (e.g., greater than 200 cells) may require culture under expansion/spheroid inducing conditions for a shorter period of time (e.g., fewer than 10-25 days) before spheroids begin to form, or may require little or no time under expansion/spheroid inducing conditions before spheroids begin to form.

In some embodiments, aggregation conditions comprise culturing cells (e.g., epithelial cells) in an aggregation well or container (e.g., AggreWell™, STEMCELL Technologies). Such wells and containers may be designed to bring cells into direct contact with each other (e.g., through gravity or centrifugation), thereby inducing the formation of aggregates. Designs may include, for example, conical shaped wells/tubes, round bottom wells/tubes, inverse pyramid-shaped wells/tubes, and the like.

In some embodiments, aggregation conditions comprise culturing cells (e.g., epithelial cells) in a hanging drop. A hanging drop culture generally involves culturing cells in a small drop of liquid, such as cell culture medium, suspended from a surface (e.g., glass surface, lid of a tissue culture plate, and the like). An example of the hanging drop system is the InSphero GravityPLUS™ Hanging Drop System (PerkinElmer; cat #ISP-06-010). A hanging drop may be suspended by gravity and surface tension, for example. Cells in a hanging drop generally are in direct contact with each other.

In some embodiment, aggregation conditions comprise culturing cells by agitating a single cell suspension culture (e.g., in a roller bottle) for a period of time until the single cell suspension culture forms a cell aggregate in suspension. Cells in a single cell suspension culture under agitation (e.g., in a roller bottle) may undergo rotational collisions, thereby forming aggregates. The process is similar to what is described, for example, in U.S. Pat. No. 8,895,300, which is incorporated by reference herein.

In some embodiments, cells (e.g., epithelial cells) are cultured under aggregation conditions for a period of time. For example, cells may be cultured under aggregation conditions for about 6 hours, about 12 hours, about 18 hours, about 24 hours, about 36 hours, about 48 hours, about 72 hours, or more. Generally, cells are cultured under aggregation conditions until cells have substantially aggregated. Cells are considered substantially aggregated when a certain fraction of cells (e.g., cells in a container or hanging drop) are aggregated. In some embodiments, cells are considered substantially aggregated when at least about 50% of cells are aggregated. For example, cells may considered substantially aggregated when at least about 50%, at least about 60%, at least about 70%, at least about 80%, at least about 90%, or about 100% of cells are aggregated. Cell aggregation can be assessed, for example, by detecting the expression and location of proteins involved in tight junctions such as ZO-1, or proteins involved in adherens junctions such as E-Cadherin.

Epithelial cells may produce one or more basement membrane components. In some embodiments, epithelial cells produce one or more basement membrane components before the cells are cultured under aggregate conditions. Epithelial cells in a cellular aggregate may continue to produce one or more basement membrane components. Basement membrane components in a cellular aggregate may be referred to as a basement membrane core. Basement membrane components and/or a basement membrane core may comprise one or more basement membrane proteins or fragments thereof. In some embodiments, basement membrane proteins comprise one or more of laminin, collagen (e.g., collagen IV), fibronectin, and nidogen.

In some embodiments, aggregation conditions are serum-free conditions. In some embodiments, aggregation conditions are feeder cell-free conditions. In some embodiments, aggregation conditions are defined conditions. In some embodiments, aggregation conditions are xeno-free conditions. In some embodiments, aggregation conditions are serum-free and feeder cell-free conditions. In some embodiments, aggregation conditions are defined, serum-free and feeder cell-free conditions. In some embodiments, aggregation conditions are xeno-free, serum-free and feeder cell-free conditions. In some embodiments, aggregation conditions are defined, xeno-free, serum-free and feeder cell-free conditions. Defined conditions, xeno-free conditions, serum-free conditions, and feeder cell-free conditions are described in further detail herein.

In some embodiments, aggregation conditions comprise one or more transforming growth factor beta (TGF-beta) inhibitors (e.g., one or more TGF-beta inhibitors described herein). In some embodiments, aggregation conditions comprise one or more cytoskeletal structure modulators (e.g., one or more cytoskeletal structure modulators described herein). In some embodiments, aggregation conditions comprise one or more transforming growth factor beta (TGF-beta) inhibitors and one or more cytoskeletal structure modulators. TGF-beta inhibitors may comprise one or more ALK5 inhibitors (e.g., A83-01, GW788388, RepSox, and SB 431542). Cytoskeletal structure modulators may comprise one or more agents that disrupt cytoskeletal structure. Cytoskeletal structure modulators may be chosen from one or more of a Rho-associated protein kinase inhibitor, a p21-activated kinase (PAK) inhibitor, and a myosin II inhibitor. In some embodiments, one or more cytoskeletal structure modulators are chosen from one or more Rho-associated protein kinase inhibitors. Rho-associated protein kinase inhibitors may be chosen from Y-27632, SR 3677, thiazovivin, HA1100 hydrochloride, HA1077 and GSK-429286. In some embodiments, one or more cytoskeletal structure modulators are chosen from one or more PAK inhibitors. PAK inhibitors may comprise IPA3. In some embodiments, one or more cytoskeletal structure modulators are chosen from one or more myosin II inhibitors. Myosin II inhibitors may comprise blebbistatin.

In some embodiments, aggregation conditions comprise calcium. In some embodiments, aggregation conditions comprise calcium at a concentration of at least about 0.5 mM. In some embodiments, aggregation conditions comprise calcium at a concentration of about 0.5 mM. In some embodiments, aggregation conditions comprise calcium at a concentration of at least about 1 mM. In some embodiments, aggregation conditions comprise calcium at a concentration of about 1 mM. In some embodiments, aggregation conditions comprise calcium at a concentration of at least about 1.5 mM. In some embodiments, aggregation conditions comprise calcium at a concentration of about 1.5 mM.

Cell-Substrate Bodies

Provided herein are methods for producing cellular spheroids. In some embodiments, a method includes generating cell-substrate bodies. Generally, cell-substrate bodies are generated prior to producing cellular spheroids. Cell-substrate bodies may be generated by attaching one or more cells (e.g., epithelial cells) to a substrate under substrate attachment conditions. One or more cells may comprise one cell that is capable of dividing. For example, if a single cell which is capable of dividing attaches to a substrate, the cell may divide and grow into multiple cells on the substrate. In some embodiments, one or more cells comprise more than one cell that is capable of dividing. One or more cells may comprise two or more cells. In some embodiments, one or more cells comprises between about 10 cells to about 200 cells. For example, one or more cells may comprise about 10 cells, about 20 cells, about 30 cells, about 40 cells, about 50 cells, about 60 cells, about 70 cells, about 80 cells, about 90 cells, about 100 cells, about 110 cells, about 120 cells, about 130 cells, about 140 cells, about 150 cells, about 160 cells, about 170 cells, about 180 cells, about 190 cells, or about 200 cells. In some embodiments, one or more cells comprises more than 200 cells. In some instances, cells are provided to a substrate at an appropriate density so that the cells substantially cover the surface of the substrate. In some embodiments, cells substantially cover the surface of the substrate when about 90% or more of the substrate surface is covered. For example, cells may substantially cover the surface of the substrate when about 90% or more, about 91% or more, about 92% or more, about 93% or more, about 94% or more, about 95% or more, about 96% or more, about 97% or more, about 98% or more, about 99% or more, or about 100% of the substrate surface is covered. For example, in the instance of microcarriers, cells may be seeded at an appropriate density so that the cells substantially cover the surface of the microcarrier. An approximate number of cells can be calculated based on the surface area of the microcarrier and the average size of the cells.

A cell-substrate body generally refers to one or more cells attached to a substrate. A substrate can be any physically separable solid to which a cell (e.g., epithelial cell) can be directly or indirectly attached including, but not limited to, particles such as microspheres, microcarriers, microparticles, and beads (e.g., paramagnetic beads, magnetic beads, microbeads, nanobeads). Solid supports also can include, for example, coated microspheres, coated microparticles, coated beads, other coated particles, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, a substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, a substrate can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of $Fe^{2+}$ and $Fe^{3+}$). In some embodiments, a substrate is a microsphere. In some embodiments, a substrate is a microcarrier.

In some embodiments, a substrate comprises a coating. In some embodiments, a substrate is a coated microsphere. In some embodiments, a substrate is a coated microcarrier. In some embodiments, a coating comprises one or more extracellular matrix components. In some embodiments, a coating comprises one or more basement membrane components. Basement membrane components may comprise one or more basement membrane proteins or fragments thereof. Basement membrane proteins may comprise one or more of laminin (e.g., LN-511), collagen, collagen IV, fibronectin, and nidogen. In some embodiments, basement membrane components comprise mimetic peptides. For example, basement membrane components comprise fibronectin-mimetic peptides, laminin-mimetic peptides, collagen-mimetic peptides, collagen IV-mimetic peptides, and/or nidogen-mimetic peptides. In some embodiments a substrate is coated with Matrigel™ (BD Biosciences).

A substrate may be a dissolvable substrate. In some embodiments, a substrate is a dissolvable microsphere. In some embodiments, a substrate is a dissolvable microcarrier. Thus, in some embodiments, a method herein comprises dissolving a substrate (e.g., dissolving a substrate after generating a cellular microsphere). Dissolving a substrate generally allows recovery of spheroids without the need for substrate separation. Any suitable dissolvable substrate may be used such as, for example, dissolvable microspheres made from gelatin, dissolvable microspheres made from starch, dissolvable microspheres made from water-soluble polyvinyl alcohol (PVA), dissolvable microcarriers made from denatured collagen, and dissolvable microcarriers made of polygalacturonic acid (PGA) polymer chains cross-linked via calcium ions (e.g., Corning® Dissolvable Microcarriers, Corning 4979 or 4987). Substrates may be dissolved according to manufacturer's instructions (e.g., dissolved using a solution of EDTA and pectinase). An example method for dissolving a substrate (e.g., Corning® Dissolvable Microcarriers) comprises the steps of: 1) a wash step with DPBS to rinse away culture media—this may be performed by settle-aspirate operation; and 2) dissolution with the addition of EDTA (which chelates calcium ions and destabilizes the polymer crosslinking), pectinase (which targets degradation of the PGA polymer), and a standard cell culture protease (which breaks down cell and extracellular matrices). Substrates may be dissolved within about 10 to 20 minutes.

A cell attached to a substrate may be referred to as a cell adhered to a substrate, a cell tethered to a substrate, and/or a cell anchored to a substrate. A cell may be attached to a substrate by way of interactions between a basal membrane of a cell (e.g., basal membrane of an epithelial cell) and one or more basement membrane components on the substrate (e.g., one or more basement membrane components in a coating on the substrate). For example, a cell may be attached to a substrate through interactions between one or more cell-matrix anchoring junctions (e.g., actin-linked cell-matric junctions, hemidesmosomes) and one or more basement membrane proteins (e.g., laminin, collagen, collagen IV, fibronectin, nidogen). In certain instances, single cells are mixed with coated substrate, and the cells can adhere to the substrate through interactions between integrin receptors and ECM proteins such as collagens, laminins, and the like.

In some embodiments, substrate attachment conditions are serum-free conditions. In some embodiments, substrate attachment conditions are feeder cell-free conditions. In some embodiments, substrate attachment conditions are defined conditions. In some embodiments, substrate attachment conditions are xeno-free conditions. In some embodiments, substrate attachment conditions are serum-free and feeder cell-free conditions. In some embodiments, substrate attachment conditions are defined, serum-free and feeder cell-free conditions. In some embodiments substrate attachment conditions are xeno-free, serum-free and feeder cell-free conditions. In some embodiments, substrate attachment conditions are defined, xeno-free, serum-free and feeder cell-free conditions. Defined conditions, xeno-free conditions, serum-free conditions, and feeder cell-free conditions are described in further detail herein.

In some embodiments, substrate attachment conditions comprise one or more transforming growth factor beta (TGF-beta) inhibitors (e.g., one or more TGF-beta inhibitors described herein). In some embodiments, substrate attachment conditions comprise one or more cytoskeletal structure modulators (e.g., one or more cytoskeletal structure modulators described herein). In some embodiments, substrate attachment conditions comprise one or more transforming growth factor beta (TGF-beta) inhibitors and one or more cytoskeletal structure modulators. TGF-beta inhibitors may comprise one or more ALK5 inhibitors (e.g., A83-01, GW788388, RepSox, and SB 431542). Cytoskeletal structure modulators may comprise one or more agents that disrupt cytoskeletal structure. Cytoskeletal structure modulators may be chosen from one or more of a Rho-associated protein kinase inhibitor, a p21-activated kinase (PAK) inhibitor, and a myosin II inhibitor. In some embodiments, one or more cytoskeletal structure modulators are chosen from one or more Rho-associated protein kinase inhibitors. Rho-associated protein kinase inhibitors may be chosen from Y-27632, SR 3677, thiazovivin, HA1100 hydrochloride, HA1077 and GSK-429286. In some embodiments, one or more cytoskeletal structure modulators are chosen from one or more PAK inhibitors. PAK inhibitors may comprise IPA3. In some embodiments, one or more cytoskeletal structure modulators are chosen from one or more myosin II inhibitors. Myosin II inhibitors may comprise blebbistatin.

In some embodiments, substrate attachment conditions comprise calcium. In some embodiments, substrate attachment conditions comprise calcium at a concentration of at least about 0.5 mM. In some embodiments, substrate attachment conditions comprise calcium at a concentration of about 0.5 mM. In some embodiments, substrate attachment conditions comprise calcium at a concentration of at least about 1 mM. In some embodiments, substrate attachment conditions comprise calcium at a concentration of about 1 mM. In some embodiments, substrate attachment conditions comprise calcium at a concentration of at least about 1.5 mM. In some embodiments, substrate attachment conditions comprise calcium at a concentration of about 1.5 mM.

Cellular Spheroids

Provided herein are methods for producing cellular spheroids. Generally, a cellular spheroid is generated after forming a cellular aggregate described herein or after forming a cell-substrate body described herein. A cellular spheroid may be produced by culturing a cellular aggregate or a cell-substrate body under spheroid-inducing conditions.

A cellular spheroid produced herein generally has a three dimensional structure. Cellular spheroids herein may be spherical in shape, substantially spherical in shape, or amorphous (e.g., generally lacking a definable shape). Cellular spheroids herein generally comprise an interior and an exterior; and may be solid, substantially solid, or hollow. Hollow spheroids may comprise a lumen (e.g., an interior lumen). Cellular spheroids herein may comprise a continuous monolayer (e.g. sheet) of cells (e.g., epithelial cells).

Provided herein are cellular spheroids comprising epithelial cells. As noted above, epithelial cells may have a basal membrane and an apical membrane. Generally, for some or all of the epithelial cells in the spheroid, the basal membrane is in the spheroid interior and the apical membrane is on the spheroid exterior. Such spheroids may be referred to as apical side outward-oriented (ASO) spheroids or apical side outward-oriented (ASO) epithelial spheroids. In some embodiments, more than 50% of the epithelial cells in a cellular spheroid have an apical-basal polarity where the basal membrane is in the spheroid interior and the apical membrane is on the spheroid exterior. For example, more than 50%, more than 60%, more than 70%, more than 80%, more than 90%, or more than 95% of the epithelial cells in a cellular spheroid may have an apical-basal polarity where the basal membrane is in the spheroid interior and the apical membrane is on the spheroid exterior. In some embodiments, about 100% of the epithelial cells in a cellular spheroid have an apical-basal polarity where the basal membrane is in the spheroid interior and the apical membrane is on the spheroid exterior.

In some embodiments, the exterior of a cellular spheroid provided herein comprises one or more features of epithelial apical membrane. For example, the exterior of a cellular spheroid provided herein may comprise cilia. In certain instances, the exterior of a cellular spheroid provided herein comprises microvilli. In some embodiments, the exterior of a cellular spheroid provided herein comprises one or more markers of epithelial apical membrane. For example, the exterior of a cellular spheroid provided herein may comprise one or more apical membrane protein markers (e.g., Cdc42, atypical protein kinase C (aPKC), Par6, Par3/Bazooka/ASIP, Crumbs, Stardust, and protein at tight junctions (PATJ)).

In some embodiments, the interior of a cellular spheroid provided herein comprises one or more features of epithelial basal membrane and/or basal lamina (basement membrane). For example, the interior of a cellular spheroid provided herein may comprise cell-matrix anchoring junctions (e.g., hemidesmosomes; actin-linked cell-matrix junctions) or components thereof (e.g., actin filaments). In some embodiments, the interior of a cellular spheroid provided herein comprises one or more basement membrane components (e.g., one or more basement membrane components described herein). In some embodiments, the interior of a cellular spheroid provided herein comprises one or more markers of epithelial basal membrane. For example, the interior of a cellular spheroid provided herein may comprise one or more basal membrane protein markers (e.g., Lethal Giant Larvae (Lgl), Discs Large (Dig), Scribble (Scrib), and Integrins which connect the cytoskeleton to extracellular matrix proteins within the basement membrane).

In some embodiments, epithelial cells in the spheroid comprise a lateral membrane. In some embodiments, the epithelial cells in the spheroid comprise intercellular junctions at the lateral membrane. In some embodiments, the epithelial cells in the spheroid comprise intercellular tight junctions at the lateral membrane. Intercellular adherens junctions, and intercellular gap junctions also may be located on the lateral membrane.

Cellular spheroids may be produced ex vivo (i.e., outside the body of a subject). Cellular spheroids may exist as isolated cellular spheroids. For example, cellular spheroids may be isolated from a physiological context (e.g., not part of a subject; not part of a human). Generally a cellular spheroid is an artificial cellular assembly (i.e., not existing in nature, and produced “by the hand of man”).

A cellular spheroid may be produced by culturing a cellular aggregate or a cell-substrate body under spheroid-inducing conditions. In some embodiments, spheroid-inducing culture conditions comprise culturing a cellular aggregate in liquid suspension. In some embodiments, spheroid-inducing culture conditions comprise culturing a cellular aggregate in liquid suspension in a low-attachment container (e.g., ultra-low attachment plate). In some embodiments, spheroid-inducing culture conditions comprise encapsulating a cellular aggregate in a hydrogel (i.e., water-infused network of polymers). Examples of hydrogels include alginate, HyStem®-C hydrogel, natural hydrogels, synthetic hydrogels, collagen-based hydrogels (e.g., PURECOL, FIBRICOL (Advanced BioMatrix); THERMACOL, COLLAGEL (Vitrogen, Flexcell)), fibrin-based hydrogels (e.g., TISSEEL, ARTISS (Baxter); EVICEL (Johnson & Johnson)), polyacrylamide, polyethylene glycol (PEG), hyaluronic acid (HA), and polypeptide-based hydrogels. In some embodiments, spheroid-inducing culture conditions comprise encapsulating a cellular aggregate in an extracellular matrix (e.g., Matrigel™ (BD Biosciences)).

In some embodiments, spheroid-inducing culture conditions comprise culturing a cell-substrate body in liquid suspension. In some embodiments, spheroid-inducing culture conditions comprise encapsulating a cell-substrate body in a hydrogel (e.g., alginate, HyStem®-C hydrogel, or any hydrogel described above). In some embodiments, spheroid-inducing culture conditions comprise encapsulating a cell-substrate body in an extracellular matrix (e.g., Matrigel™ (BD Biosciences)).

In some embodiments, spheroid-inducing conditions are serum-free conditions. In some embodiments, spheroid-inducing conditions are feeder cell-free conditions. In some embodiments, spheroid-inducing conditions are defined conditions. In some embodiments, spheroid-inducing conditions are xeno-free conditions. In some embodiments, spheroid-inducing conditions are serum-free and feeder cell-free conditions. In some embodiments, spheroid-inducing conditions are defined, serum-free and feeder cell-free conditions. In some embodiments spheroid-inducing conditions are xeno-free, serum-free and feeder cell-free conditions. In some embodiments, spheroid-inducing conditions are defined, xeno-free, serum-free and feeder cell-free conditions. Defined conditions, xeno-free conditions, serum-free conditions, and feeder cell-free conditions are described in further detail herein.

In some embodiments, spheroid-inducing conditions comprise one or more transforming growth factor beta (TGF-beta) inhibitors (e.g., one or more TGF-beta inhibitors described herein). In some embodiments, spheroid-inducing conditions comprise one or more cytoskeletal structure modulators (e.g., one or more cytoskeletal structure modulators described herein). In some embodiments, spheroid-inducing conditions comprise one or more transforming growth factor beta (TGF-beta) inhibitors and one or more cytoskeletal structure modulators. TGF-beta inhibitors may comprise one or more ALK5 inhibitors (e.g., A83-01, GW788388, RepSox, and SB 431542). Cytoskeletal structure modulators may comprise one or more agents that disrupt cytoskeletal structure. Cytoskeletal structure modulators may be chosen from one or more of a Rho-associated protein kinase inhibitor, a p21-activated kinase (PAK) inhibitor, and a myosin II inhibitor. In some embodiments, one or more cytoskeletal structure modulators are chosen from one or more Rho-associated protein kinase inhibitors. Rho-associated protein kinase inhibitors may be chosen from Y-27632, SR 3677, thiazovivin, HA1100 hydrochloride, HA1077 and GSK-429286. In some embodiments, one or more cytoskeletal structure modulators are chosen from one or more PAK inhibitors. PAK inhibitors may comprise IPA3. In some embodiments, one or more cytoskeletal structure modulators are chosen from one or more myosin II inhibitors. Myosin II inhibitors may comprise blebbistatin.

In some embodiments, spheroid-inducing conditions comprise calcium. In some embodiments, spheroid-inducing conditions comprise calcium at a concentration of at least about 0.5 mM. In some embodiments, spheroid-inducing conditions comprise calcium at a concentration of about 0.5 mM. In some embodiments, spheroid-inducing conditions comprise calcium at a concentration of at least about 1 mM. In some embodiments, spheroid-inducing conditions comprise calcium at a concentration of about 1 mM. In some embodiments, spheroid-inducing conditions comprise calcium at a concentration of at least about 1.5 mM. In some embodiments, spheroid-inducing conditions comprise calcium at a concentration of about 1.5 mM.

In some embodiments, a population of cellular spheroids described herein is provided. A population of cellular spheroids may be a homogeneous population. A homogeneous population of cellular spheroids refers to a population where all spheroids comprise epithelial cells having a polarity where the basal membrane is in the spheroid interior and the apical membrane is on the spheroid exterior. Accordingly, a homogeneous population of cellular spheroids refers a homogeneous population of apical side outward-oriented (ASO) spheroids. Generally, a homogeneous population of ASO cellular spheroids comprises no spheroids having an opposite orientation (i.e., apical side inward-oriented). A population of cellular spheroids may be a substantially homogeneous population. A substantially homogeneous population of cellular spheroids refers to a population where substantially all spheroids comprise epithelial cells having a polarity where the basal membrane is in the spheroid interior and the apical membrane is on the spheroid exterior. Accordingly, a substantially homogeneous population of cellular spheroids refers a substantially homogeneous population of apical side outward-oriented (ASO) spheroids. Generally, a substantially homogeneous population of ASO cellular spheroids comprises a small percentage (e.g., less than about 10%) of spheroids having an opposite orientation (i.e., apical side inward-oriented). For example, a substantially homogeneous population of ASO cellular spheroids may comprise less than about 10%, less than about 9%, less than about 8%, less than about 7%, less than about 6%, less than about 5%, less than about 4%, less than about 3%, less than about 2%, or less than about 1% of spheroids having an opposite orientation (i.e., apical side inward-oriented). In some embodiments, a substantially homogeneous population of ASO cellular spheroids comprises less than about 1% of spheroids having an opposite orientation (i.e., apical side inward-oriented).

In some embodiments, a population of uniformly sized cellular spheroids is provided. A population of uniformly sized cellular spheroids generally refers to a population of spheroids with diameters ranging within about ±100 microns relative to a median diameter for the population. In some embodiments, a median diameter is between about 50 to 100 microns. For example, a median diameter may be about 50 microns, 51 microns, 52 microns, 53 microns, 54 microns, 55 microns, 56 microns, 57 microns, 58 microns, 59 microns, 60 microns, 61 microns, 62 microns, 63 microns, 64 microns, 65 microns, 66 microns, 67 microns, 68 microns, 69 microns, 70 microns, 71 microns, 72 microns, 73 microns, 74 microns, 75 microns, 76 microns, 77 microns, 78 microns, 79 microns, 80 microns, 81 microns, 82 microns, 83 microns, 84 microns, 85 microns, 86 microns, 87 microns, 88 microns, 89 microns, 90 microns, 91 microns, 92 microns, 93 microns, 94 microns, 95 microns, 96 microns, 97 microns, 98 microns, 99 microns, or 100 microns. In some embodiments, a median diameter is about 60 microns. In some embodiments, a median diameter is about 75 microns. In some embodiments, a population of uniformly sized cellular spheroids comprises spheroids with diameters between about 30 microns to about 150 microns. In some embodiments, a population of uniformly sized cellular spheroids comprises spheroids with diameters between about 40 microns to about 150 microns. In some embodiments, a population of uniformly sized cellular spheroids comprises spheroids with diameters between about 30 microns to about 125 microns. In some embodiments, a population of uniformly sized cellular spheroids comprises spheroids with diameters between about 40 microns to about 125 microns. In some embodiments, a population of uniformly sized cellular spheroids comprises spheroids with diameters between about 40 microns to about 110 microns. In some embodiments, a population of uniformly sized cellular spheroids comprises less than 10% spheroids with diameters larger than 150 microns. In some embodiments, a population of uniformly sized cellular spheroids comprises less than 5% spheroids with diameters larger than 150 microns. In some embodiments, a population of uniformly sized cellular spheroids comprises less than 1% spheroids with diameters larger than 150 microns. In some embodiments, a population of uniformly sized cellular spheroids comprises no spheroids with diameters larger than 150 microns.

Uses of Cellular Spheroids

In certain embodiments, cellular spheroids provided herein may be used for certain biomedical and laboratory uses such as, for example, biological function studies (e.g., interactions between infectious agents (e.g., viruses, bacteria) and epithelial cells; interactions between inflammatory agents (e.g., gluten) and epithelial cells (e.g., intestinal epithelial cells); cellular functions of the apical-basal polarized epithelium), drug/chemical delivery and safety analyses, toxicology analysis, mutational screening, biomolecule production (e.g., expression of proteins (e.g., therapeutic proteins, secreted proteins)), diagnostics (e.g., identifying abnormal epithelial cells), and/or therapeutics (e.g., screening candidate therapeutic agents; cell therapy (e.g., genetically modified cells for cell therapy)). In some instances, cellular spheroids may be used for autologous applications (e.g., autologous implant), and in certain instances, cellular spheroids may be used for non-autologous applications (e.g., non-autologous implant or drug screening). In some instances, cellular spheroids may be collected and/or isolated and/or stored (e.g., for a cell bank). In some instances, cellular spheroids may be frozen and thawed for later use. In some instances, cellular spheroids may undergo more than one freeze/thaw round.

In one example, cellular spheroids may be used for protein expression, virus/vaccine production, and the like. In some instances, cellular spheroids may be used for protein expression (e.g., proteins secreted from the apical side of epithelial cells). In some instances, epithelial cells in a cellular spheroid can be genetically modified to express a protein of interest (e.g., a therapeutic protein; a secreted protein). In some instances, an epithelial cell or group of cells can be genetically modified and then induced to form a cellular spheroid under spheroid-inducing culture conditions described herein. Such genetic modification of the cells would be designed to, for example, insert a transgene (e.g., a disease-modifying transgene) that codes for a particular protein. A protein expressed by a transgene may act as a functional version of a missing or a defective protein, or may act as a suppressor or inhibitor of genes or other proteins. Cellular spheroids comprising cells expressing a particular protein can then be placed in a subsequent environment, for example, such as an autologous implant or a non-autologous implant into a subject, such that the cells will produce the protein in vivo. For example, cellular spheroids comprising cells expressing a protein can be placed in a subsequent environment, such as alginate encapsulation, which can protect the spheroids from being attacked by immune cells and used as a non-autologous implant into a subject, such that the cells will produce the protein in vivo.

In another example, cellular spheroids may be useful for identifying one or more candidate treatments for a subject. For example, cellular spheroids may be assayed for generating a response profile. A response profile typically is a collection of one or more data points that can indicate the likelihood that a particular treatment will produce a desired response, for example in normal or abnormal epithelial cells. A response to a therapeutic agent may include, for example, cell death (e.g., by necrosis, toxicity, apoptosis, and the like), and/or a reduction of growth rate for the cells. Methods to assess a response to a therapeutic agent include, for example, determining a dose response curve, a cell survival curve, a therapeutic index and the like. For example, nasal or trachea epithelial cells may be isolated from a subject carrying mutation(s) in the CFTR gene, and the spheroid-inducing culture conditions herein may be utilized to obtain cellular spheroids for further analysis, such as, for example, assays for generating a response profile to therapeutic agents such as drugs, antibodies, RNAi and antisense nucleic acids, and/or gene therapy regimes.

In another example, cellular spheroids can be useful for identifying candidate treatments for a subject having a condition marked by the presence of abnormal or diseased epithelial cells. Such conditions may include for example neoplasias, hyperplasias, and malignant tumors or benign tumors. In some instances, abnormal epithelial cells obtained from a subject may be induced to form a cellular spheroid under spheroid-inducing culture conditions described herein to produce an in vitro population of abnormal epithelial cell spheroids. For example, tumor cells may be isolated from a subject's primary or metastatic tumor, and the spheroid-inducing culture conditions herein may be utilized to obtain cellular spheroids for further analysis, such as, for example, functional, phenotypic and/or genetic characterization of the tumor cells.

In another example, cellular spheroids can be useful for studying the interactions between infectious or inflammatory agents and epithelial cells. For example, intestinal epithelial cells obtained from a subject having Celiac disease may be induced to form cellular spheroids under spheroid-inducing culture conditions described herein. Such spheroids, having the apical side facing outwards, would allow accessibility to the microvilli of the intestinal epithelial cells. This configuration would be useful for studying the interactions between gluten and intestinal epithelial cells, and the inflammatory effects in Celiac patients.

In another example, cellular spheroids can be useful for the vaccine production. For example, human rhinovirus-C (HRV-C) strains generally only infect multiciliated cells in the respiratory tract through the apical side, and generally cannot be propagated in conventional 2D airway epithelial cell culture. Airway epithelial cells may be induced to form cellular spheroids under spheroid-inducing culture conditions described herein. Such spheroids, having the apical side facing outwards, would allow HRV-C to infect and propagate in the multiciliated cells. Viral particles produced from the infected cells could be attenuated and used as vaccines to prevent future infections by the HRV-C viruses.

In another example, cellular spheroids can be useful for studying the toxicity of a drug or chemical. For example, cigarette smoke generally is associated with airway epithelial mucus cell hyperplasia and a decrease in ciliated cells. Airway epithelial cells may be induced to form cellular spheroids under spheroid-inducing culture conditions described herein. Such spheroids, having the apical side facing outwards, would allow studying the effect of cigarette smoke extract by adding it to the culture medium to study the effect on cilia beating, mucus production and toxicity towards the cells within the spheroids.

In another example, cellular spheroids can be useful for testing various drug delivery systems. For example, orally ingested drugs may be formulated for optimal absorption at a particular location in the digestive tract (e.g., small intestine, large intestine). Intestinal epithelial cells may be induced to form cellular spheroids under spheroid-inducing culture conditions described herein. Such spheroids, having the apical side facing outwards, would allow studying the absorption properties of various drug formulations.

Cell Culture

Provided herein are methods and compositions for cell culture. In particular, provided herein are culture conditions for generating cellular spheroids. Cell culture, or culture, typically refers to the maintenance of cells in an artificial, in vitro environment, or the maintenance of cells in an external, ex vivo environment (i.e., outside of an organism), and can include the cultivation of individual cells and tissues. Certain cell culture systems described herein may be an ex vivo environment and/or an in vitro environment.

In some embodiments, primary cells are isolated and cultured. Primary cells may be isolated, for example, from a single needle biopsy, from a tissue biopsy, from a plucked hair, from body fluids like urine or body-cavity fluids, from the circulation of a subject, and the like. After isolation, cellular material may be washed (e.g., with saline and/or a PBS solution). Cellular material may be treated with an enzymatic solution such as, for example, collagenase, dispase and/or trypsin, to promote dissociation of cells from the tissue matrix. Dispase, for example, may be used to dissociate epithelium from underlying tissue. An intact epithelium may then be treated with trypsin or collagenase, for example. Such digestion steps often result in a slurry containing dissociated cells and tissue matrix. The slurry can then be centrifuged with sufficient force to separate the cells from the remainder of the slurry. A cell pellet may then be removed and washed with buffer and/or saline and/or cell culture medium. The centrifuging and washing can be repeated any number of times. After a final washing, cells can then be washed with any suitable cell culture medium. In certain instances, digestion and washing steps may not be performed if the cells are sufficiently separated from the underlying tissue upon isolation (e.g., for cells isolated from circulation or using needle biopsy). In some embodiments, cells are dissociated from the tissue (e.g., epithelium) of origin prior to aggregation, substrate attachment, and/or spheroid formation. Thus, in certain embodiments, spheroids are not formed directly from tissue explants. In some embodiments, the starting material for a method described herein for spheroid formation is a single cell suspension. In some embodiments, cells are substantially dissociated from the tissue (e.g., epithelium) of origin. Cells that are substantially dissociated from the tissue (e.g., epithelium) of origin comprise less than 10% (e.g., less than 9%, less than 8%, less than 7%, less than 6%, less than 5%, less than 4%, less than 3%, less than 2%, less than 1%) cells that are attached to one another, are attached to other cell types (e.g., non-epithelial cells), and/or are attached to extracellular components from the tissue of origin. In some embodiments, cells are completely dissociated from the tissue (e.g., epithelium) of origin. Cells that are completely dissociated from the tissue (e.g., epithelium) of origin are not attached to one another, are not attached to other cell types (e.g., non-epithelial cells), and are not attached to any extracellular components from the tissue of origin.

In some embodiments, cells such as tumor cells may be isolated from the circulation of a subject. In certain embodiments, tumor cells may be isolated according to cell markers specifically expressed on certain types of tumor cells (see e.g., Lu. J., et al., Intl. J. Cancer, 126(3):669-683 (2010) and Yu, M., et al., J. Cell Biol., 192(3): 373-382 (2011), which are incorporated by reference). Cells may or may not be counted using an electronic cell counter, such as a Coulter Counter, or they can be counted manually using a hemocytometer.

Cell seeding densities may be adjusted according to certain desired culture conditions. For example, an initial seeding density of from about $1\times10^3$ to about $1\text{-}10\times10^5$ cells per $cm^2$ may be used. In some embodiments, an initial seeding density of from about 1-10 to about $1\text{-}10\times10^5$ cells per $cm^2$ may be used. In certain instances, $1\times10^6$ cells may be cultured in a 75 $cm^2$ culture flask. Cell density may be altered as needed at any passage.

Cells may be cultivated in a cell incubator at about 37° C. at normal atmospheric pressure. The incubator atmosphere may be humidified and may contain from about 3-10% carbon dioxide in the air. In some instances, the incubator atmosphere may contain from about 0.1-30% oxygen. Temperature, pressure and carbon dioxide and oxygen concentration may be altered as needed. Culture medium pH may be in the range of about 7.1 to about 7.6, or from about 7.1 to about 7.4, or from about 7.1 to about 7.3.

Cell culture medium may be replaced every 1-2 days or more or less frequently as needed. As the cells approach confluence in the culture vessel, they may be passaged. A cell passage is a splitting or dividing of the cells, and a transferring a portion of the cells into a new culture vessel or culture environment. Cells which are adherent to the cell culture surface may require detachment. Methods of detaching adherent cells from the surface of culture vessels are well known and can include the use of enzymes such as trypsin.

A single passage refers to a splitting or manual division of the cells one time, and a transfer of a smaller number of cells into a new container or environment. When passaging, the cells can be split into any ratio that allows the cells to attach and grow. For example, at a single passage the cells can be split in a 1:2 ratio, a 1:3 ratio, a 1:4 ratio, a 1:5 ratio, and so on. In some embodiments, cells are passaged at least about 1 time to at least about 300 times. For example, cells may be passaged at least about 2 times, 5 times, 10 times, 20 times, 30 times, 40 times, 50 times, 60 times, 70 times, 80 times, 90 times, 100 times, 200 times or 300 times. In some embodiments, cells are passaged at least about 15 times. In some embodiments, cells are passaged at least about 25 times. In some embodiments, epithelial cells (e.g., epithelial cells in cellular aggregates, epithelial cells in cell-substrate bodies, epithelial cells in cellular spheroids) have not undergone passaging. Accordingly, in some embodiments, cellular aggregates, cell-substrate bodies, and/or cellular spheroids do not comprise passaged epithelial cells.

Cell growth generally refers to cell division, such that one mother cell divides into two daughter cells. Cell growth may be referred to as cell expansion. Cell growth herein generally does not refer to an increase in the actual size (e.g., diameter, volume) of the cells. Stimulation of cell growth can be assessed by plotting cell populations (e.g., cell population doublings) over time. A cell population with a steeper growth curve generally is considered as growing faster than a cell population with a less steep curve. Growth curves can be compared for various treatments between the same cell types, or growth curves can be compared for different cell types with the same conditions, for example.

In some embodiments, a method herein comprises expanding a population of cells. For example, a method herein may comprise expanding a population of epithelial cells prior to generating cellular spheroids. Epithelial cells may be expanded under expansion culture conditions (e.g., expansion culture conditions described in U.S. Pat. Nos. 9,790,471, 9,963,680, and U.S. Patent Application Publication No. US20170073635, each of which are incorporated by reference in their entirety). For example, expansion culture conditions may be serum free and feeder cell-free conditions and may comprise a transforming growth factor beta (TGF-beta) inhibitor and a cytoskeletal structure modulator. In certain instances, expansion culture conditions are defined, xeno-free, serum-free and feeder cell-free conditions and comprise a transforming growth factor beta (TGF-beta) inhibitor and albumin. In some embodiments, expansion culture conditions comprise 1) a serum free medium (e.g., Keratinocyte-SFM (Gibco/Thermo Fisher 17005-042)

supplied with prequalified human recombinant Epidermal Growth Factor 1-53 (EGF 1-53, used at about 0.5 ng/mL) and Bovine Pituitary Extract (BPE, used at about 30 μg/mL)); 2) a transforming growth factor beta (TGF-beta) inhibitor (e.g., A 83-01, used at about 1 μM); 3) a cytoskeletal structure modulator (e.g., Y-27632, used at about 5 μM); and 4) and a beta-adrenergic agonist (e.g., isoproterenol, used at about 3 μM).

Expanding a population of cells may be referred to as proliferating a population of cells. Expanding a population of cells may be expressed as population doubling. A cell population doubling occurs when the cells in culture divide so that the number of cells is doubled. In some instances, cells are counted to determine if a population of cells has doubled, tripled or multiplied by some other factor. The number of population doublings may not be equivalent to the number of times a cell culture is passaged. For example, passaging the cells and splitting them in a 1:3 ratio for further culturing may not be equivalent to a tripled cell population. A formula that may be used for the calculation of population doublings (PD) is presented in Equation A:

$$n = 3.32*(\log Y - \log I) + X \qquad \text{Equation A}$$

where n=the final PD number of the cell culture when it is harvested or passaged, Y=the cell yield at the time of harvesting or passaging, I=the cell number used as inoculum to begin that cell culture, and X=the PD number of the originating cell culture that is used to initiate the subculture.

A population of cells may double a certain number of times over a certain period of time. In some embodiments, a population of cells is capable of doubling, or doubles, at least about 1 time to at least about 500 times over a certain period of time. For example, a population of cells may be capable of doubling, or double, at least about 2 times, 5 times, 10 times, 20 times, 30 times, 40 times, 50 times, 60 times, 70 times, 80 times, 90 times, 100 times, 110 times, 120 times, 130 times, 140 times, 150 times, 160 times, 170 times, 180 times, 190 times, 200 times, 250 times, 300 times, 350 times, 400 times, 450 times or 500 times. In some embodiments, a population of cells doubles, or is capable of doubling, a certain number of times over a period of about 1 day to about 500 days. For example, a population of cells may double, or is capable of doubling, a certain number of times over a period of about 2 days, 5 days, 10 days, 20 days, 30 days, 40 days, 50 days, 60 days, 70 days, 80 days, 90 days, 100 days, 110 days, 120 days, 130 days, 140 days, 150 days, 160 days, 170 days, 180 days, 190 days, 200 days, 250 days, 300 days, 350 days, 400 days, 450 days or 500 days.

Expanding a population of cells may be expressed as fold increase in cell numbers. A formula that may be used for the calculation of fold increase as a function of population doublings is presented in Equation B:

$$F = 2^n \qquad \text{Equation B}$$

where F=the fold increase in cell numbers after n population doublings. For example, after one (1) population doubling, the number of cells increases by 2 fold, and after two (2) population doublings, the number of cells increases by 4 ($2^2$=4) fold, and after three (3) population doublings, the number of cells increases by 8 ($2^3$=8) fold, and so on. Hence, after twenty (20) population doublings, the number of cells increases by more than one million fold ($2^{20}$=1,048,576), and after thirty (30) population doublings, the number of cells increases by more than one billion fold ($2^{3o}$=1,073, 741,824), and after forty (40) population doublings, the number of cells increases by more than one trillion fold ($2^{4o}$=1,099,511,627,776), and so on. In some embodiments, a population of cells is expanded, or is capable of being expanded, at least about 2-fold to at least about a trillion-fold. For example, a population of cells may be expanded at least about 5-fold, 10-fold, 15-fold, 20-fold, 30-fold, 40-fold, 50-fold, 100-fold, 1,000-fold, 10,000-fold, 100, 000-fold, 1 million-fold, 1 billion-fold, or 1 trillion-fold. A particular fold expansion may occur over a certain period of time in culture such as, for example, 2 days, 3 days, 4 days, 5 days, 10 days, 20 days, 30 days, 40 days, 50 days, 100 days or more.

Cells may be continuously proliferated or continuously cultured. Continuous proliferation or continuous culture refers to a continuous dividing of cells, reaching or approaching confluence in the cell culture container such that the cells require passaging and addition of fresh medium to maintain their health. Continuously proliferated cells or continuously cultured cells may possess features that are similar to, or the same as, immortalized cells. In some embodiments, cells continue to grow and divide for at least about 5 passages to at least about 300 passages. For example, cells may continue to grow and divide for at least about 10 passages, 20 passages, 30 passages, 40 passages, 50 passages, 60 passages, 70 passages, 80 passages, 90 passages, 100 passages, 200 passages or 300 passages.

In some embodiments, epithelial cells are a heterogeneous population of epithelial cells upon initial collection and plating and become a homogenous population of epithelial cells after one or more passages. For example, a heterogeneous population of epithelial cells may become a homogeneous population of epithelial cells after 2 passages, after 3 passages, after 4 passages, after 5 passages, after 10 passages, after 20 passages, after 30 passages, after 40 passages, after 50 passages, or after 100 or more passages.

In some embodiments, epithelial cells are characterized by the cell types and/or differentiation states that are included in, or absent from, a population of epithelial cells at initial collection and plating. In some embodiments, epithelial cells are characterized by the cell types and/or differentiation states that are included in, or absent from, a population of epithelial cells after one or more passages. For example, epithelial cells may be characterized by the cell types and/or differentiation states that are included in, or absent from, a population of epithelial cells after 2 passages, after 3 passages, after 4 passages, after 5 passages, after 10 passages, after 20 passages, after 30 passages, after 40 passages, after 50 passages, or after 100 or more passages. In some embodiments, epithelial cells are characterized by the cell types and/or differentiation states that are included in an originating epithelial cell population. In some embodiments, epithelial cells are characterized by the cell types and/or differentiation states that are included in an expanded epithelial cell population.

In some embodiments, cells do not undergo differentiation during expansion, continuous proliferation or continuous culture. For example, cells may not differentiate into terminally differentiated cells or other cell types during expansion, continuous proliferation or continuous culture. In some embodiments, cells of a particular organ or lineage do not differentiate into cells of a different organ or lineage. For example, airway epithelial cells may not differentiate into fibroblast cells, intestinal epithelial cells, intestinal goblet cells, gastric epithelial cells, or pancreatic epithelial cells during expansion, continuous proliferation or continuous culture. In some embodiments, cells undergo some degree of differentiation during expansion, continuous proliferation or continuous culture. For example, lineage-committed epithelial cells may differentiate into cell types within a given lineage and/or organ-specific epithelial cells may differentiate into other cell types within a given organ during expansion, continuous proliferation or continuous culture.

In some embodiments, a certain proportion of the epithelial cells may be at G0 resting phase where the cells have exited cell cycle and have stopped dividing, which includes both quiescence and senescence states. A certain proportion of the epithelial cells may be at G1 phase, in which the cells increase in size and get ready for DNA synthesis. A certain proportion of the epithelial cells may be at S phase, in which DNA replication occurs. A certain proportion of the epithelial cells may be at G2 phase, in which the cells continue to grow and get ready to enter the M (mitosis) phase and divide. A certain proportion of the epithelial cells may be at M (mitosis) phase and complete cell division.

In some embodiments, cells are characterized by telomere length. In some embodiments, cells in an originating epithelial cell population are characterized by telomere length. In some embodiments, cells in an expanded epithelial cell population are characterized by telomere length. Typically, telomere length shortens as cells divide. A cell may normally stop dividing when the average length of telomeres is reduced to a certain length, for example, 4 kb. In some embodiments, average telomere length of cells cultured in media and/or culture conditions described herein may be reduced to a length of less than about 10 kb, and the cells can continue to divide. For example, average telomere length of cells cultured in media and/or culture conditions described herein may be reduced to a length of less than about 9 kb, 8 kb, 7 kb, 6 kb, 5 kb, 4 kb, 3 kb, 2 kb, or 1 kb, and the cells can continue to divide. Average telomere length sometimes is expressed as a mean telomere length or median telomere length. Average telomere length may be determined using any suitable method for determining telomere length, and may vary according to cell type. In some embodiments, average telomere length is determined as relative abundance of telomeric repeats to that of a single copy gene.

In some embodiments, cells are expanded, continuously proliferated or continuously cultured for a certain number of passages without altering cellular karyotype. For example, an alteration in cellular karyotype may include duplication or deletion of chromosomes or portions thereof and/or translocation of a portion of one chromosome to another. Karyotype may be assayed for a population of cells after a certain number of passages which may be compared to a population of cells of the same origin prior to passaging. In some embodiments, cells have an unaltered karyotype after at least about 5 passages to at least about 300 passages. For example, cells may have an unaltered karyotype after at least about 10 passages, 20 passages, 30 passages, 40 passages, 50 passages, 60 passages, 70 passages, 80 passages, 90 passages, 100 passages, 200 passages or 300 passages. In certain instances, cells that have an unaltered karyotype after a certain number of passages may be referred to as conditionally immortalized cells or conditionally reprogrammed cells. Generally, conditionally immortalized cells or conditionally reprogrammed cells retain a normal karyotype and remain nontumorigenic. In some embodiments, epithelial cells (e.g., epithelial cells in cellular aggregates, epithelial cells in cell-substrate bodies, epithelial cells in cellular spheroids) comprise conditionally immortalized cells or conditionally reprogrammed cells. In some embodiments, epithelial cells (e.g., epithelial cells in cellular aggregates, epithelial cells in cell-substrate bodies, epithelial cells in cellular spheroids) do not comprise conditionally immortalized cells or conditionally reprogrammed cells.

In some embodiments, methods herein comprise use of an extracellular matrix (ECM) and/or ECM components. In some embodiments, methods herein do not comprise use of an extracellular matrix (e.g., liquid suspension conditions described herein). For example, methods herein may include culturing epithelial cells, generating cellular aggregates, generating cell-substrate bodies, and/or generating cellular spheroids without the use of an ECM. ECM may contain basement membrane components such as basement membrane proteins or fragments thereof. ECM may contain certain polysaccharides, water, elastin, and certain glycoproteins such as, for example, collagen (e.g., collagen IV), entactin (nidogen), fibronectin, and laminin. ECM may contain mimetic peptides (e.g., fibronectin-mimetic peptides and/or laminin-mimetic peptides). ECM may be generated by culturing ECM-producing cells, and optionally removing these cells, prior to the plating of epithelial cells. Examples of ECM-producing cells include chondrocytes, which produce collagen and proteoglycans; fibroblast cells, which produce type IV collagen, laminin, interstitial procollagens and fibronectin; and colonic myofibroblasts, which produce collagens (type I, Ill, and V), chondroitin sulfate proteoglycan, hyaluronic acid, fibronectin, and tenascin-C. ECM also may be commercially provided. Examples of commercially available extracellular matrices include extracellular matrix proteins (Invitrogen), basement membrane preparations from Engelbreth-Holm-Swarm (EHS) mouse sarcoma cells (e.g., Matrigel™ (BD Biosciences)), coagulated fibrin matrices, and synthetic extracellular matrix materials, such as ProNectin (Sigma Z378666). Mixtures of extracellular matrix materials may be used in certain instances. Extracellular matrices may be homogeneous (comprise essentially a single component) or heterogeneous (comprise a plurality of components). Heterogeneous extracellular matrices generally comprise a mixture of ECM components including, for example, a plurality of glycoproteins and growth factors. Example heterogeneous extracellular matrices include basement membrane preparations from Engelbreth-Holm-Swarm (EHS) mouse sarcoma cells (e.g., Matrigel™). In some embodiments, methods herein do not comprise use of a heterogeneous extracellular matrix. For example, methods herein may include culturing epithelial cells, generating cellular aggregates, generating cell-substrate bodies, and/or generating cellular spheroids without the use of a heterogeneous extracellular matrix. Extracellular matrices may be defined (all or substantially all components and amounts thereof are known) or undefined (all or substantially all components and amounts thereof are not known). Example undefined extracellular matrices include basement membrane preparations from Engelbreth-Holm-Swarm (EHS) mouse sarcoma cells (e.g., Matrigel™). In some embodiments, methods herein do not comprise use of an undefined extracellular matrix. For example, methods herein may include culturing epithelial cells, generating cellular aggregates, generating cell-substrate bodies, and/or generating cellular spheroids without the use of an undefined extracellular matrix.

In some embodiments, cells are cultured in a container. A container for culturing cells may be referred to as a culture vessel, and may include plates, dishes, flasks, stacking vessels, wells (e.g., in a 6-well, 24-well, 96-well plate; in a 384-well plate), roller bottle, WAVE bag, bioreactor, and the like. In some embodiments, cells are cultured in a container comprising a coating. For example, cells may be plated onto the surface of culture vessels containing one or more attachment factors. In some embodiments, cells are plated onto the surface of culture vessels without attachment factors. In embodiments where attachment factors are used, a culture container can be precoated with a natural, recombinant or synthetic attachment factor or factors or peptide fragments thereof, such as but not limited to collagen, fibronectin, laminin, and natural or synthetic fragments thereof. In some embodiments, a culture vessel is precoated with collagen. In some embodiments, a culture vessel is precoated with a basement membrane matrix. In some embodiments, a culture vessel is precoated with a homogeneous and/or defined extracellular matrix. In some embodiments, cells are cultured in a container having a low attachment surface (e.g., Corning Ultra-low attachment surface). Cells cultured in containers having a low attachment surface are generally inhibited from adhering or attaching to the surface of the container, and therefore are forced into a suspended state. A low attachment surface may contain a coating that is hydrophilic, non-ionic, and/or neutrally charged. The coating may be a hydrogel. The coating may be covalently bound to the surface of a container. In some embodiments, cells are cultured in a container comprising no coating.

Cells may maintain one or more functional characteristics throughout the culturing process. In some embodiments, a functional characteristic may be a native functional characteristic. Native functional characteristics generally include traits possessed by a given cell type while in its natural environment (e.g., a cell within the body of a subject before being extracted for cell culture). Examples of native functional characteristics include gas exchange capabilities in pulmonary epithelial cells, detoxification capabilities in liver epithelial cells, filtration capabilities in kidney epithelial cells, and endocrine production and/or metabolite responsiveness in pancreatic islet cells. In some embodiments, cells do not maintain one or more functional characteristics throughout the culturing process.

A characteristic of cells in culture sometimes is determined for an entire population of cells in culture. For example, a characteristic such as average telomere length, doubling time, growth rate, division rate, gene level or marker level, for example, is determined for the population of cells in culture. A characteristic often is representative of cells in the population, and the characteristic may vary for particular cells in the culture. For example, where a population of cells in a culture exhibits an average telomere length of 4 kb, a portion of cells in the population can have a telomere length of 4 kb, a portion of cells can have a telomere length greater than 4 kb and a portion of cells can have a telomere length less than 4 kb. In another example, where a population of cells is characterized as expressing a high level of a particular gene or marker, all cells in the population express the particular gene or marker at a high level in some embodiments, and in certain embodiments, a portion of cells in the population (e.g., at least 75% of cells) express the particular gene or marker at a high level and a smaller portion of the cells express the particular gene at a moderate level, low level or undetectable level. In another example, where a population of cells is characterized as not expressing, or expressing a low level of a particular gene or marker, no cells in the population express the particular gene or marker at a detectable level in some embodiments, and in certain embodiments, a portion of cells in the population (e.g., less than 10% of cells) express the particular gene or marker at a detectable level.

A characteristic of cells in culture (e.g., ability to form a spheroid, viability, growth, population doublings, marker expression) sometimes is compared to the same characteristic observed for cells cultured in control culture conditions. Often, when comparing a characteristic observed for cells cultured in control culture conditions, an equal or substantially equal amount of cells from the same source is added to certain culture conditions and to control culture conditions. Control culture conditions may include the same base medium (e.g., a serum-free base medium) and additional components minus one or more agents (e.g., one or more of a TGF-beta inhibitor (e.g., one or more TGF-beta signaling inhibitors), a ROCK inhibitor, a myosin II inhibitor, a PAK inhibitor). In some embodiments, cell culture conditions consist essentially of certain components necessary to achieve one or more characteristics of cells in culture (e.g., ability to form a spheroid, viability, growth, population doublings, marker expression) compared to the same characteristic(s) observed for cells cultured in control culture conditions. When a cell culture condition consists essentially of certain components, additional components or features may be included that do not have a significant effect on the one or more characteristics of cells in culture (e.g., ability to form a spheroid, viability, growth, population doublings, marker expression) when compared to control culture conditions. Such additional components or features may be referred to as non-essential components and may include typical cell culture components such as salts, vitamins, amino acids, certain growth factors, fatty acids, and the like.

Feeder Cells

Cells may be cultured with or without feeder cells. Generally, feeder cells are cells co-cultured with other cell types for certain cell culture systems. Feeder cells typically are nonproliferating cells and sometimes are treated to inhibit proliferation, and often are maintained in a live, metabolically active state. For example, feeder cells can be irradiated with gamma irradiation and/or treated with mitomycin C, which can arrest cell division while maintaining the feeder cells in a metabolically active state.

Feeder cells can be from any mammal and the animal source of the feeder cells need not be the same animal source as the cells being cultured. For example, feeder cells may be, but are not limited to mouse, rat, canine, feline, bovine, equine, porcine, non-human primate and human feeder cells. Types of feeder cells may include splenocytes, macrophages, thymocytes, amniotic cells, and/or fibroblasts. Types of feeder cells may be the same cell type which they support. Types of feeder cells may not be the same cell type which they support. J2 cells are used as feeder cells for certain cell culture systems, and are a subclone of mouse fibroblasts derived from the established Swiss 3T3 cell line.

In some embodiments, cells are cultured in the absence of feeder cells. In some embodiments, cells are not cultured in media conditioned by feeder cells (i.e., not cultured in a conditioned medium). In some embodiments, cells are not cultured in the presence of fractionated feeder cells, or particulate and/or soluble fractions of feeder cells. Any one or all of the above culture conditions (i.e., cultured in the absence of feeder cells; not cultured in a conditioned medium; not cultured in the presence of fractionated feeder cells, or particulate and/or soluble fractions of feeder cells) may be referred to as feeder-cell free conditions or feeder-free conditions. Culture conditions provided herein typically are feeder-cell free culture conditions.

Media and Cell Culture Compositions

Cells typically are cultured in the presence of a cell culture medium. Spheroid-inducing culture conditions provided herein typically comprise a cell culture medium. Aggregation conditions provided herein typically comprise a cell culture medium. Substrate attachment conditions provided herein typically comprise a cell culture medium. Expansion culture conditions provided herein typically comprise a cell culture medium. A cell culture medium may include any type of medium such as, for example, a serum-free medium; a serum-containing medium; a reduced-serum medium; a protein-free medium; a chemically defined medium; a protein-free, chemically defined medium; a peptide-free, protein-free, chemically defined medium; an animal protein-free medium; a xeno-free medium; a defined, xeno-free medium; a BPE-free medium, and the like and combinations thereof. A cell culture medium typically is an aqueous-based medium and can include any of the commercially available and/or classical media such as, for example, Dulbecco's Modified Essential Medium (DMEM), Knockout-DMEM (KODMEM), Ham's F12 medium, DMEM/Ham's F12, Advanced DMEM/Ham's F12, Ham's F-10 medium, RPMI 1640, Eagle's Basal Medium (EBM), Eagle's Minimum Essential Medium (MEM), Glasgow Minimal Essential Medium (G-MEM), Medium 199, Keratinocyte-SFM (KSFM; Gibco/Thermo-Fisher) complete medium or base medium, prostate epithelial growth medium (PrEGM; Lonza), CHO cell culture media, PER.C6 media, 293 media, hybridoma media, PneumaCult™-ALI medium (STEMCELL Technologies), and the like and combinations thereof.

In some embodiments, a cell culture medium is a serum-containing medium. Serum may include, for example, fetal bovine serum (FBS), fetal calf serum, goat serum or human serum. Generally, serum is present at between about 1% to about 30% by volume of the medium. In some instances, serum is present at between about 0.1% to about 30% by volume of the medium. In some embodiments, a medium contains a serum replacement.

In some embodiments, a cell culture medium is a serum-free medium. A serum-free medium generally does not contain any animal serum (e.g. fetal bovine serum (FBS), fetal calf serum, goat serum or human serum), but may contain certain animal-derived products such as serum albumin (e.g., purified from blood), growth factors, hormones, carrier proteins, hydrolysates, and/or attachment factors. In some embodiments, a serum-free cell culture medium comprises Keratinocyte-SFM (KSFM; Gibco/Thermo-Fisher; e.g., cat #17005-042). Keratinocyte-SFM generally is supplied with prequalified human recombinant Epidermal Growth Factor 1-53 (EGF 1-53; may be used at about 0.5 ng/mL) and Bovine Pituitary Extract (BPE; may be used at about 30 μg/mL). KSFM may include insulin, transferrin, hydrocortisone, Triiodothyronine (T3). Complete KSFM generally includes a KSFM base medium, EGF 1-53 and BPE. In some embodiments, a serum-free cell culture medium comprises Keratinocyte-SFM base medium (KSFM base medium; Gibco/Thermo-Fisher). KSFM base medium generally refers to a KSFM medium without EGF 1-53 and BPE. A representative formulation of KSFM base medium is described, for example, in U.S. Pat. No. 6,692,961. In some embodiments, a cell culture medium is a serum-free and BPE-free medium (e.g., PneumaCult™-ALI Medium; STEMCELL Technologies).

In some embodiments, a cell culture medium is a defined serum-free medium. Defined serum-free media, sometimes referred to as chemically-defined serum-free media, generally include identified components present in known concentrations, and generally do not include undefined components such as animal organ extracts (e.g., pituitary extract, BPE) or other undefined animal-derived products (e.g., unquantified amount of serum albumin (e.g., purified from blood), growth factors, hormones, carrier proteins, hydrolysates, and/or attachment factors). Defined media may include a basal media such as, for example, DMEM, F12, or RPMI 1640, containing one or more of amino acids, vitamins, inorganic acids, inorganic salts, alkali silicates, purines, pyrimidines, polyamines, alpha-keto acids, organosulphur compounds, buffers (e.g., HEPES), antioxidants and energy sources (e.g., glucose); and may be supplemented with one or more of recombinant albumin, recombinant growth factors, chemically defined lipids, recombinant insulin and/or zinc, recombinant transferrin or iron, selenium and an antioxidant thiol (e.g., 2-mercaptoethanol or 1-thioglycerol). Recombinant albumin and/or growth factors may be derived, for example, from non-animal sources such as rice or *E. coli*, and in certain instances synthetic chemicals are added to defined media such as a polymer polyvinyl alcohol which can reproduce some of the functions of bovine serum albumin (BSA)/human serum albumin (HSA). In some embodiments, a defined serum-free media may be selected from MCDB 153 medium (Sigma-Aldrich M7403), Modified MCDB 153 medium (Biological Industries, Cat. No. 01-059-1), MCDB 105 medium (Sigma-Aldrich M6395), MCDB 110 medium (Sigma-Aldrich M6520), MCDB 131 medium (Sigma-Aldrich M8537), MCDB 201 medium (Sigma-Aldrich M6670), and modified versions thereof. In some embodiments, a defined serum-free media is MCDB 153 medium (Sigma-Aldrich M7403). In some embodiments, a defined serum-free media is Modified MCDB 153 medium (Biological Industries, Cat. No. 01-059-1). In some embodiments, a defined serum-free cell culture medium comprises Keratinocyte-SFM medium without BPE (e.g., KSFM base medium; Gibco/Thermo-Fisher).

In some embodiments, a cell culture medium is a xeno-free serum-free medium. Xeno-free generally means having no components originating from animals other than the animal from which cells being cultured originate. For example, a xeno-free culture has no components of non-human animal origin when human cells are cultured. In some embodiments, a cell culture medium is a defined xeno-free serum-free medium. Defined xeno-free serum-free media, sometimes referred to as chemically-defined xeno-free serum-free media, generally include identified components present in known concentrations, and generally do not include undefined components such as animal organ extracts (e.g., pituitary extract) or other undefined animal-derived products (e.g., serum albumin (e.g., purified from blood), growth factors, hormones, carrier proteins, hydrolysates, and/or attachment factors). Defined xeno-free serum-free media may or may not include lipids and/or recombinant proteins from animal sources (e.g., non-human sources) such as, for example, recombinant albumin, recombinant growth factors, recombinant insulin and/or recombinant transferrin. Recombinant proteins may be derived, for example, from non-animal sources such as a plant (e.g., rice) or bacterium (e.g., *E. coli*), and in certain instances synthetic chemicals are added to defined media (e.g., a polymer (e.g., polyvinyl alcohol)), which can reproduce some of the functions of bovine serum albumin (BSA)/human serum albumin (HSA). In some embodiments, a defined serum-free medium may comprise a commercially available xeno-free serum substitute, such as, for example, XF-KOSR™ (Invitrogen). In some embodiments, a defined serum-free medium may comprise a commercially available xeno-free base medium such as, for example, mTeSR2™ (Stem Cell Technologies), NutriStem™ (StemGent), X-Vivo 10™ or X-Vivo 15™ (Lonza Biosciences), or HEScGRO™ (Millipore). In some embodiments, a defined xeno-free serum-free cell culture medium comprises Keratinocyte-SFM base medium (KSFM base medium; Gibco/Thermo-Fisher).

Additional ingredients may be added to a cell culture medium herein. For example, such additional ingredients may include amino acids, vitamins, inorganic salts, inorganic acids, adenine, ethanolamine, D-glucose, heparin, N-[2-hydroxyethyl]piperazine-N'-[2-ethanesulfonic acid] (HEPES), hydrocortisone, insulin, lipoic acid, phenol red, phosphoethanolamine, putrescine, sodium pyruvate, pyruvic acid, ammonium metavanadate, molybdic acid, silicates, alkali silicates (e.g., sodium metasilicate), purines, pyrimidines, polyamines, alpha-keto acids, organosulphur compounds, buffers (e.g., HEPES), antioxidants, thioctic acid, triiodothyronine (T3), thymidine and transferrin. In certain instances, insulin and/or transferrin may be replaced by ferric citrate or ferrous sulfate chelates. Amino acid may include, for example, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. Vitamins may include, for example, biotin, D-biotin, choline chloride, D-$Ca^{+2}$-pantothenate, D-pantothenic acid, folic acid, i-inositol, myo-inositol, niacinamide, pyridoxine, riboflavin, thiamine and vitamin B12. Inorganic salts may include, for example, calcium salt (e.g., $CaCl_2$), $CuSO_4$, $FeSO_4$, KCl, a magnesium salt (e.g., $MgCl_2$, $MgSO_4$), a manganese salt (e.g., $MnCl_2$), sodium acetate, NaCl, $NaHCO_3$, $Na_2HPO_4$, $Na_2SO_4$, and ions of certain trace elements including selenium, silicon, molybdenum, vanadium, nickel, tin and zinc. These trace elements may be provided in a variety of forms, including the form of salts such as $Na_2SeO_3$, $Na_2SiO_3$, $(NH_4)_6Mo_7O_{24}$, $NH_4VO_3$, $NiSO_4$, SnCl and ZnSO. Additional ingredients may include, for example, heparin, epidermal growth factor (EGF), at least one agent increasing intracellular cyclic adenosine monophosphate (cAMP) levels, at least one fibroblast growth factor (FGF), acidic FGF, granulocyte macrophage colony-stimulating factor (GM-CSF) (uniprot accession number P04141), granulocyte colony stimulating factor (G-CSF) (uniprot accession number P09919), hepatocyte growth factor (HGF) (uniprot accession number P14210), neuregulin 1 (NRG1) (uniprot accession number Q61CV5), neuregulin 2 (NRG2) (uniprot accession number Q3M186), neuregulin 3 (NRG3) (uniprot accession number B9EGV5), neuregulin 4 (NRG4) (uniprot accession number QOP6N6), epiregulin (ERG) (uniprot accession number 014944), betacellulin (BC) (uniprot accession number Q86UF5), Interleukin-11 (11_11) (uniprot accession number P20809), a collagen and heparin-binding EGF-like growth factor (HB-EGF) (uniprot accession number Q14487).

In some embodiments, a cell culture medium comprises calcium. In some embodiments, calcium is present at a concentration of about 2 mM or more. In some embodiments, calcium is present at a concentration below 2 mM. In some embodiments, calcium is present at a concentration between about 0.5 mM and 2 mM. For example, calcium may be present at a concentration of about 0.5 mM, 0.6 mM, 0.7 mM, 0.8 mM, 0.9 mM, 1.0 mM, 1.2 mM, 1.3 mM, 1.4 mM, 1.5 mM, 1.6 mM, 1.7 mM, 1.8 mM, 1.9 mM, or 2.0 mM. In some embodiments, calcium is present at a concentration of about 1.5 mM. In some embodiments, calcium is present at a concentration of about 1 mM. In some embodiments, calcium is present at a concentration of about 0.5 mM. In some embodiments, calcium is present at a concentration below 1 mM. For example, calcium may be present a concentration below 1 mM, below 900 μM, below 800 μM, below 700 μM, below 600 μM, below 500 μM, below 400 μM, below 300 μM, below 200 μM, below 100 μM, below 90 μM, below 80 μM, below 70 μM, below 60 μM, below 50 μM, below 40 μM, below 30 μM, below 20 μM, or below 10 μM. In some embodiments, calcium is present at a concentration below 500 μM. In some embodiments, calcium is present at a concentration below 300 μM. In some embodiments, calcium is present at a concentration below 100 μM. In some embodiments, calcium is present at a concentration below 20 μM. In some embodiments, calcium is present at a concentration of about 90 μM.

Certain components may be added to a cell culture to induce formation of tight junctions. For example, calcium or additional calcium may be added to a cell culture to induce formation of tight junctions. In some embodiments, calcium may be added such that the calcium concentration in the cell culture medium is at least about 0.5 mM to induce formation of tight junctions. For example, the calcium concentration in the cell culture medium can be at least about 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM or 2.0 mM. In some embodiments, calcium is added to a cell culture such that the calcium concentration in the cell culture medium is about 1.5 mM to induce formation of tight junctions.

Certain components may be added to a cell culture to promote differentiation. For example, calcium or additional calcium may be added to a cell culture to promote differentiation. In some embodiments, calcium may be added such that the calcium concentration in the cell culture medium is at least about 0.5 mM to promote differentiation. For example, the calcium concentration in the cell culture medium can be at least about 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM or 2.0 mM. In some embodiments, calcium is added to a cell culture such that the calcium concentration in the cell culture medium is about 1.5 mM to promote differentiation.

In some embodiments, a cell culture medium comprises albumin (e.g., serum albumin). Albumin is a protein generally abundant in vertebrate blood. In some embodiments, a cell culture medium comprises bovine serum albumin (BSA). In some embodiments, a cell culture medium comprises human serum albumin (HSA). Albumin may be purified (e.g., from human or bovine serum) or may be recombinantly produced, such as for example, in plants (e.g., rice), bacteria (e.g., *E. coli*), or yeast (e.g., *Pichia pastoris, Saccharomyces cerevisiae*). In some embodiments, a cell culture medium comprises recombinant human serum albumin (rHSA). In some embodiments, a cell culture medium comprises recombinant human serum albumin (rHSA) produced in rice.

In some embodiments, culture conditions herein comprise one or more defined xeno-free serum replacement components. Defined xeno-free serum replacement components may include, for example, albumin proteins, functional fragments of albumin proteins, proteins having amino acid sequences that are at least 90% identical to an albumin protein, proteins having one or more functional traits of albumin, allelic variants of albumin, storage albumins, albuminoids, ovalbumin, and blood transport proteins. Blood transport proteins generally function in blood (e.g., serum, plasma) as carriers for molecules and elements having low solubility such as, for example, hormones, salts, bile salts, fatty acids (e.g., free fatty acids), calcium, sodium, potassium, ions, transferrin, hematin, tryptophan, bilirubin (e.g., unconjugated bilirubin), thyroxine (T4), vitamins and certain drugs. Blood transport proteins may include, for example, serum albumin, alpha-fetoprotein, vitamin D-binding protein and afamin. Defined xeno-free serum replacement components generally exclude undefined organ extracts and other undefined mixtures.

In some embodiments, a defined xeno-free serum replacement component comprises serum albumin. Serum albumins are secreted proteins produced in the liver and generally found in abundance in blood. Serum albumins typically regulate blood volume (e.g., by maintaining the oncotic pressure (i.e., colloid osmotic pressure) of blood), and generally can serve as carriers for molecules and elements having low water solubility such as, for example, lipid-soluble hormones, bile salts, unconjugated bilirubin, free fatty acids, calcium, ions, transferrin, hematin, tryptophan, and certain drugs (e.g., warfarin, phenobutazone, clofibrate, phenytoin, and the like). In certain instances, serum albumin can act as antioxidant and/or anticoagulant and can serve as a plasma pH buffer. In some embodiments, a defined xeno-free serum replacement component comprises human serum albumin.

In some embodiments, a defined xeno-free serum replacement component comprises a recombinantly produced albumin. For example, albumin may be recombinantly produced in plants (e.g., rice), bacteria (e.g., *E. coli*), or yeast (e.g., *Pichia pastoris, Saccharomyces cerevisiae*). In some embodiments, a defined xeno-free serum replacement component comprises a recombinant human serum albumin (rHA). In some embodiments, a defined xeno-free serum replacement component comprises a recombinant human serum albumin (rHA) expressed in rice (e.g., Sigma, A9731).

In some embodiments, a defined xeno-free serum replacement component comprises a functional fragment of an albumin protein. A functional fragment generally retains one or more functions of a full-length albumin such as, for example, the ability to regulate blood volume and/or serve as a carrier protein. In some instances, a functional fragment performs a function at a level that is at least about 50% the level of function for a full length albumin. In some instances, a functional fragment performs a function at a level that is at least about 75% the level of function for a full length albumin. In some instances, a functional fragment performs a function at a level that is at least about 90% the level of function for a full length albumin. In some instances, a functional fragment performs a function at a level that is at least about 95% the level of function for a full length albumin. Levels of albumin function can be assessed, for example, using any suitable functional assay for albumin such as, for example, albumin binding assays (e.g., binding of albumin to anionic forms of colored dyes (e.g., methyl orange, HABA (2-(4'-hydroxyazobenzene)-benzoic acid), bromcresol green, and the like), binding and subsequent solubilization of hydrophobic compounds, binding of albumin to neonatal Fc receptor (FcRn), and other ligand-albumin binding assays (e.g., using a site-specific fluorescent probe as described, for example, in U.S. Pat. No. 8,476,081, the entirety of which is incorporated by reference herein).

In some embodiments, culture conditions herein comprise one or more agents that inhibit retinoic acid signaling. Retinoic acid is a metabolite of vitamin A (retinol) that mediates the functions of vitamin A required for growth and development, primarily in chordate animals. Retinoic acid signaling generally functions during early embryonic development, helping to determine position along the embryonic anterior/posterior axis by serving as an intercellular signaling molecule that guides development of the posterior portion of an embryo.

Retinoic acid generally acts by binding to the retinoic acid receptor (RAR), which is bound to DNA as a heterodimer with the retinoid X receptor (RXR) in regions called retinoic acid response elements (RAREs). Binding of the retinoic acid ligand to RAR alters the conformation of the RAR, which affects the binding of other proteins that either induce or repress transcription of a nearby gene (including Hox genes and several other target genes). Retinoic acid receptors can mediate transcription of different sets of genes controlling differentiation of a variety of cell types, thus the target genes regulated typically depend upon the target cells. In some cells, one of the target genes is the gene for the retinoic acid receptor itself (RAR-beta in mammals), which amplifies the response. Control of retinoic acid levels is maintained by a suite of proteins that control synthesis and degradation of retinoic acid.

In some embodiments, culture conditions herein comprise one or more retinoic acid receptor (RAR) antagonists. RAR antagonists may include RARa antagonists, RARβ antagonists, and/or RARγ antagonists; and RAR antagonists may include pan-RAR antagonists. Non-limiting examples of RAR antagonists include BMS-453, BMS-195614, BMS 493, AGN 193109-d7, AGN 193109, AGN 194310, AGN 194431, AGN 194301, CD 2665, ER 50891, LE 135 and MM 11253. In some embodiments, culture conditions herein comprise one or more agents that inhibit retinoic acid signaling by way of additional mechanisms (e.g., by affecting retinoic acid production and/or metabolism).

In some embodiments, retinoic acid signaling inhibitors (e.g., receptor (RAR) antagonists) are used at sub-micromolar concentrations. For example, retinoic acid signaling inhibitors may be used at concentrations below 1 micromolar, below 100 nanomolar, or below 10 nanomolar.

In some embodiments, a cell culture medium comprises one or more lipids. Lipids generally refer to oils, fats, waxes, sterols, fat-soluble vitamins (e.g., vitamins A, D, E, and K), fatty acids, monoglycerides, diglycerides, triglycerides, phospholipids, glycerolipids, glycerophospholipids, sphingolipids, saccharolipids, polyketides, prenol lipids and the like, and may include mixtures of lipids (e.g., chemically defined lipids mixtures). In some embodiments, lipids may be selected from arachidonic acid, cholesterol, DL-alpha-tocopherol acetate, linoleic acid, linolenic acid, myristic acid, oleic acid, palmitic acid, palmitoleic acid, pluronic F-68, stearic acid, polysorbate 80 (TWEEN 80), TWEEN 20, cod liver oil fatty acids (methyl esters), polyoxyethylenesorbitan monooleate, D-α-tocopherol acetate. In some embodiments, lipids may include one or more of linoleic acid, linolenic acid, oleic acid, palmitic acid, and stearic acid. In some embodiments, a lipids mix may be a commercially available lipids mix (e.g., Chemically Defined Lipid Concentrate (Gibco, 11905-031); Lipid Mixture (Sigma-Aldrich L5146); Lipid Mixture 1, Chemically Defined (Sigma-Aldrich L0288)). In some embodiments, a lipids mix may include a mixture of lipids supplied with a commercially available albumin (e.g., AlbuMAX® I Lipid-Rich BSA (Gibco, 11020-039)).

In some embodiments, a cell culture medium comprises one or more mitogenic growth factors. For example, a mitogenic growth factor may include epidermal growth factor (EGF), transforming growth factor-alpha (TGF-alpha), fibroblast growth factor (FGF), basic fibroblast growth factor (bFGF), acidic fibroblast growth factor (aFGF), brain-derived neurotrophic factor (BDNF), platelet-derived growth factor (PDGF), insulin-like growth factor I (IGF-I), insulin-like growth factor II (IGF-II), and/or keratinocyte growth factor (KGF). In some embodiments, a medium does not comprise a mitogenic growth factor.

In some embodiments, a cell culture medium comprises one or more mitogenic supplements. For example, a mitogenic supplement may include bovine pituitary extract (BPE; Gibco/Thermo-Fisher), B27 (Gibco/Thermo-Fisher), N-Acetylcysteine (Sigma), GEM21 NEUROPLEX (Gemini Bio-Products), and N2 NEUROPLEX (Gemini Bio-Products). In some embodiments, a cell culture medium does not comprise a mitogenic supplement.

In some embodiments, a cell culture medium comprises one or more agents that increase intracellular cyclic adenosine monophosphate (cAMP) levels. For example, a cell culture medium may comprise one or more beta-adrenergic agonists (e.g., one or more beta-adrenergic receptor agonists). Beta-adrenergic agonists (e.g., beta-adrenergic receptor agonists) generally are a class of sympathomimetic agents which activate beta adrenoceptors (e.g., beta-1 adrenergic receptor, beta-2 adrenergic receptor, beta-3 adrenergic receptor). The activation of beta adrenoceptors activates adenylate cyclase, which leads to the activation of cyclic adenosine monophosphate (cAMP). Beta-adrenergic agonists (e.g., beta-adrenergic receptor agonists) may include, for example, epinephrine, isoproterenol, dobutamine, xamoterol, salbutamol (ALBUTEROL), levosalbutamol (LEVALBUTEROL), fenoterol, formoterol, metaproterenol, salmeterol, terbutaline, clenbuterol, isoetarine, pirbuterol, procaterol, ritodrine, arbutamine, befunolol, bromoacetylalprenololmenthane, broxaterol, cimaterol, cirazoline, denopamine, dopexamine, etilefrine, hexoprenaline, higenamine, isoxsuprine, mabuterol, methoxyphenamine, nylidrin, oxyfedrine, prenalterol, ractopamine, reproterol, rimiterol, tretoquinol, tulobuterol, zilpaterol, and zinterol. In some embodiments, a cell culture medium comprises isoproterenol. In some embodiments, a cell culture medium comprises isoproterenol at a concentration of between about 0.5 μM to about 20 μM. For example, isoproterenol may be present at a concentration of about 0.5 μM, about 0.6 μM, about 0.7 μM, about 0.8 μM, about 0.9 μM, about 1 μM, about 1.25 μM, about 1.5 μM, about 1.75 μM, about 2 μM, about 2.5 μM, about 3 μM, about 3.5 μM, about 4 μM, about 4.5 μM, about 5 μM, about 5.5 μM, about 6 μM, about 7 μM, about 8 μM, about 9 μM, about 10 μM, about 11 μM, about 12 μM, about 13 μM, about 14 μM, or about 15 μM.

Other agents that increase intracellular cAMP level may include agents which induce a direct increase in intracellular cAMP levels (e.g., dibutyryl cAMP), agents which cause an increase in intracellular cAMP levels by an interaction with a cellular G-protein (e.g., cholera toxin and forskolin), and agents which cause an increase in intracellular cAMP levels by inhibiting the activities of cAMP phosphodiesterases (e.g., isobutylmethylxanthine (IBMX) and theophylline).

In some embodiments, a cell culture medium comprises one or more inhibitors. Inhibitors may include, for example, one or more TGF-beta inhibitors (e.g., one or more TGF-beta signaling inhibitors), one or more p21-activated kinase (PAK) inhibitors, one or more myosin II inhibitors (e.g., non-muscle myosin II (NM II) inhibitors), and one or more Rho kinase inhibitors (e.g., one or more Rho-associated protein kinase inhibitors). Such classes of inhibitors are discussed in further detail below. Inhibitors may be in the form of small molecule inhibitors (e.g., small organic molecules), antibodies, RNAi molecules, antisense oligonucleotides, recombinant proteins, natural or modified substrates, enzymes, receptors, peptidomimetics, inorganic molecules, peptides, polypeptides, aptamers, and the like and structural or functional mimetics of these. An inhibitor may act competitively, non-competitively, uncompetitively or by mixed inhibition. For example, in certain embodiments, an inhibitor may be a competitive inhibitor of the ATP binding pocket of a target kinase (e.g., protein kinase). In some embodiments, an inhibitor disrupts the activity of one or more receptors. In some embodiments, an inhibitor disrupts one or more receptor-ligand interactions. In some embodiments, an inhibitor may bind to and reduce the activity of its target. In some embodiments, an inhibitor may bind to and reduce the activity of its target by about 10% or more compared to a control. For example, an inhibitor may bind to and reduce the activity of its target by about 20% or more, 30% or more, 40% or more, 50% or more, 60% or more, 70% or more, 80% or more, 90% or more, 95% or more, or 99% or more compared to a control. Inhibition can be assessed using a cellular assay, for example.

In some embodiments, an inhibitor is a kinase inhibitor (e.g., a protein kinase inhibitor). The effectiveness of a kinase inhibitor inhibiting its target's biological or biochemical function may be expressed as an $IC_{50}$ value. The $IC_{50}$ generally indicates how much of a particular inhibitor is required to inhibit a kinase by 50%. In some embodiments, an inhibitor has an $IC_{50}$ value equal to or less than 1000 nM, equal to or less than 500 nM, equal to or less than 400 nM, equal to or less than 300 nM, equal to or less than 200 nM, equal to or less than 100 nM, equal to or less than 50 nM, equal to or less than 20 nM, or equal to or less than 10 nM.

In some embodiments, an inhibitor may directly or indirectly affect one or more cellular activities, functions or characteristics. For example, an inhibitor may induce telomerase reverse transcriptase expression in cultured cells, for example through the inhibition of the TGF-beta signaling pathway. In certain embodiments, a TGF-beta inhibitor (e.g., a TGF-beta signaling inhibitor) activates telomerase reverse transcriptase expression in cultured cells. In certain embodiments, an ALK5 inhibitor activates telomerase reverse transcriptase expression in cultured cells. In certain embodiments, A83-01 activates telomerase reverse transcriptase expression in cultured cells. In another example, an inhibitor may modulate cytoskeletal structure (e.g., disrupt cytoskeletal structure) within cultured cells, for example through the inhibition of Rho kinase (e.g., Rho-associated protein kinase), p21-activated kinase (PAK), and/or myosin II (e.g., non-muscle myosin II (NM II)). Modulation the cytoskeletal structure may include, for example, a modification of, a disruption to, or a change in any aspect of cytoskeletal structure including actin microfilaments, tubulin microtubules, and intermediate filaments; or interaction with any associated proteins, such as molecular motors, crosslinkers, capping proteins and nucleation promoting factors. In certain embodiments, a ROCK inhibitor modulates the cytoskeletal structure within cultured cells. In certain embodiments, Y-27632 modulates the cytoskeletal structure within cultured cells. In certain embodiments, a PAK1 inhibitor modulates the cytoskeletal structure within cultured cells. In certain embodiments, IPA3 modulates the cytoskeletal structure within cultured cells. In certain embodiments, a myosin II inhibitor (e.g., a non-muscle myosin II (NM II) inhibitor) modulates the cytoskeletal structure within cultured cells. In certain embodiments, blebbistatin modulates the cytoskeletal structure within cultured cells.

Cells may be cultured to stimulate differentiation of cells into the cells of the organ or tissue from which the cells were originally derived. For example, cells may be seeded onto one side of a permeable membrane. In some instances, cells cultured on one side of a permeable membrane can be exposed to air while the cells receive nutrients from the other side of the permeable membrane, and such culture may be referred to as an air-liquid-interface. In some instances, cells develop increasing transmembrane electric resistance (TEER) during air-liquid-interface differentiation. In another example, cells may be seeded into or onto a natural or synthetic three-dimensional cell culture surface. A non-limiting example of a three-dimensional surface is a Matrigel®-coated culture surface. In some instances, cells are embedded in Matrigel® or other hydrogels. Other three dimensional culture environments include surfaces comprising collagen gel and/or a synthetic biopolymeric material in any configuration, such as a hydrogel, for example.

TGF-Beta Inhibitors

In some embodiments, a method herein comprises inhibiting transforming growth factor beta (TGF-beta) signaling in cultured epithelial cells. TGF-beta signaling generally controls proliferation, cellular differentiation, and other functions in a variety of cell types, and can play a role in cell cycle control, regulation of the immune system, and development in certain cell types. Inhibition of TGF-beta signaling may include inhibition of any TGF-beta signaling pathway and/or member of the TGF-beta superfamily including ligands such as TGF-beta1, TGF-beta2, TGF-beta3, inhibins, activin, anti-müllerian hormone, bone morphogenetic protein (BMP; e.g., BMP1-7, BMP8a, BMP8b, BMP10, BMP 11, BMP15)), decapentaplegic, nodal, activin, and Vg-1; receptors such as TGF-beta superfamily type I receptors, TGF-beta superfamily type II receptors, type I serine/threonine kinase receptors, type II serine/threonine kinase receptors, TGF-beta type I receptor, TGF-beta type II receptor, activin receptor, nodal receptor, activin/nodal receptor, activin receptor-like kinases (ALKs; e.g., ALK1, ALK2, ALK3, ALK4, ALK5, ALK6, ALK7 and ALK8); and downstream effectors such as R-SMAD and other SMAD proteins (e.g., SMAD1, SMAD2, SMAD3, SMAD4, SMAD5, SMAD6, SMAD7, SMAD 8/9).

In some embodiments, the activity of one or more activin receptor-like kinases is inhibited. In some embodiments, one or more activin receptor-like kinase receptor-ligand interactions are inhibited. In some embodiments, the activity of one or more TGF-beta receptors is inhibited. In some embodiments, one or more TGF-beta receptor-ligand interactions are inhibited. In some embodiments, the activity of one or more TGF-beta type I receptors is inhibited. In some embodiments, one or more TGF-beta type I receptor-ligand interactions are inhibited. In some embodiments, the activity of one or more type I activin/nodal receptors is inhibited. In some embodiments, one or more type I activin/nodal receptor-ligand interactions are inhibited. In some embodiments, the activity of one or more type I nodal receptors is inhibited. In some embodiments, one or more type I nodal receptor-ligand interactions are inhibited. In some embodiments, one or more of ALK1, ALK2, ALK3, ALK4, ALK5, ALK6, ALK7 and ALK8 are inhibited. In some embodiments, ALK5 is inhibited. In some embodiments, ALK4 is inhibited. In some embodiments, ALK7 is inhibited. In some embodiments, ALK5, ALK4, and/or ALK7 are inhibited. In some embodiments, ALK5, ALK4, and ALK7 are inhibited.

In some embodiments, a cell culture medium comprises one or more TGF-beta inhibitors (e.g., one or more TGF-beta signaling inhibitors). In some embodiments, a TGF-beta inhibitor (e.g., a TGF-beta signaling inhibitor) binds to one or more TGF-beta receptors. In some embodiments, a TGF-beta inhibitor (e.g., a TGF-beta signaling inhibitor) binds to one or more TGF-beta ligands. In some embodiments, a TGF-beta inhibitor (e.g., a TGF-beta signaling inhibitor) binds to one or more SMAD proteins. In some embodiments, a TGF-beta inhibitor (e.g., a TGF-beta signaling inhibitor) binds to one or more TGF-beta receptors and one or more TGF-beta ligands. In some embodiments, a TGF-beta inhibitor (e.g., a TGF-beta signaling inhibitor) binds to one or more TGF-beta receptors and one or more SMAD proteins. In some embodiments, a TGF-beta inhibitor (e.g., a TGF-beta signaling inhibitor) disrupts one or more TGF-beta receptor-ligand interactions. In some embodiments, a TGF-beta inhibitor (e.g., a TGF-beta signaling inhibitor) disrupts one or more TGF-beta receptor-SMAD interactions. In some embodiments, a TGF-beta inhibitor (e.g., a TGF-beta signaling inhibitor) blocks phosphorylation or autophosphorylation of a TGF-beta receptor. In some embodiments, a TGF-beta inhibitor (e.g., a TGF-beta signaling inhibitor) promotes the de-phosphorylation of one or more TGF-beta receptors. In some embodiments, a TGF-beta inhibitor (e.g., a TGF-beta signaling inhibitor) blocks phosphorylation of one or more SMAD proteins. In some embodiments, a TGF-beta inhibitor (e.g., a TGF-beta signaling inhibitor) promotes the de-phosphorylation of one or more SMAD proteins. In some embodiments, a TGF-beta inhibitor (e.g., a TGF-beta signaling inhibitor) promotes the ubiquitin-mediated degradation of one or more TGF-beta receptors. In some embodiments, a TGF-beta inhibitor (e.g., a TGF-beta signaling inhibitor) promotes the ubiquitin-mediated degradation of one or more SMAD proteins. In some embodiments, a TGF-beta inhibitor (e.g., a TGF-beta signaling inhibitor) affects the nuclear translocation of SMADs, nuclear shuffling of SMADs, interactions of SMAD with co-activators, and the like. In certain instances, TGF-beta signaling can be measured by SMAD reporter assays (e.g., SBE Reporter Kit (TGFβ/SMAD signaling pathway) BPS Bioscience, Catalog #60654; TGF/SMAD Signaling Pathway SBE Reporter—HEK293 Cell Line, BPS Bioscience, Catalog #60653). In some embodiments, one or more TGF-beta inhibitors (e.g., a TGF-beta signaling inhibitors) include ALK5, ALK4, and/or ALK7 inhibitors.

A TGF-beta inhibitor (e.g., a TGF-beta signaling inhibitor) may be an ALK5 inhibitor, in some embodiments. An ALK5 inhibitor may bind to ALK5 or one or more ALK5 ligands or both. An ALK5 inhibitor may bind to ALK5 or one or more downstream SMAD proteins or both. An ALK5 inhibitor may disrupt one or more ALK5-ligand interactions or may disrupt one or more ALK5-SMAD interactions. In some embodiments, an ALK5 inhibitor blocks phosphorylation of SMAD2.

ALK5 inhibitors may include one or more small molecule ALK5 inhibitors. In some embodiments, an ALK5 inhibitor is an ATP analog. In some embodiments, an ALK5 inhibitor comprises the structure of Formula A:

Formula A

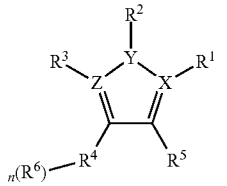

where:

X, Y and Z independently are chosen from N, C and O;

$R^1$, $R^2$ and $R^3$ independently are chosen from hydrogen, C1-C10 alkyl, substituted C1-C10 alkyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl);

n is 0 or 1;

$R^4$, $R^5$ and $R^6$ independently are chosen from hydrogen, C1-C10 alkyl, substituted C1-C10 alkyl, C1-C10 alkoxy, substituted C1-C10 alkoxy, C1-C6 alkanoyl, C1-C6 alkoxycarbonyl, substituted C1-C6 alkanoyl, substituted C1-C6 alkoxycarbonyl, C3-C9 cycloalkyl, substituted C3-C9 cycloalkyl, C5-C10 aryl, substituted C5-C10 aryl, C5-C10 cycloaryl, substituted C5-C10 cycloaryl, C5-C9 heterocyclic, substituted C5-C9 heterocyclic, C5-C9 hetercycloaryl, substituted C5-C9 heterocycloaryl, -linker-(C3-C9 cycloalkyl), -linker-(substituted C3-C9 cycloalkyl), -linker-(C5-C10 aryl), -linker-(substituted C5-C10 aryl), -linker-(C5-C10 cycloaryl), -linker-(substituted C5-C10 cycloaryl), -linker-(C5-C9 heterocyclic), -linker-(substituted C5-C9 heterocyclic), -linker-(C5-C9 hetercycloaryl), -linker-(substituted C5-C9 heterocycloaryl); and the substituents on the substituted alkyl, alkoxy, alkanoyl, alkoxycarbonyl cycloalkyl, aryl, cycloaryl, heterocyclic or heterocycloaryl groups are hydroxyl, C1-C10 alkyl, hydroxyl C1-C10 alkylene, C1-C6 alkoxy, C3-C9 cycloalkyl, C5-C9 heterocyclic, C1-6 alkoxy C1-6 alkenyl, amino, cyano, halogen or aryl.

ALK5 inhibitors may include, for example, A83-01 (3-(6-Methyl-2-pyridinyl)-N-phenyl-4-(4-quinolinyl)-1H-pyrazole-1-carbothioamide), GW788388 (4-[4-[3-(2-Pyridinyl)-1H-pyrazol-4-yl]-2-pyridinyl]-N-(tetrahydro-2H-pyran-4-yl)-benzamide), RepSox (2-(3-(6-Methylpyridine-2-yl)-1H-pyrazol-4-yl)-1,5-naphthyridine), and SB 431542 (4-[4-(1,3-benzodioxol-5-yl)-5-(2-pyridinyl)-1H-imidazol-2-yl]benzamide). In some embodiments, the ALK5 inhibitor is A83-01.

ROCK (Rho-Associated Protein Kinase) Inhibitors

In some embodiments, a method herein comprises inhibiting the activity of Rho kinase (e.g., Rho-associated protein kinase) in cultured epithelial cells. In some embodiments, a method herein does not comprise inhibiting the activity of Rho kinase (e.g., Rho-associated protein kinase) in cultured epithelial cells. Rho kinase (e.g., Rho-associated protein kinase) belongs to the Rho GTPase family of proteins, which includes Rho, Rac1 and Cdc42 kinases. An effector molecule of Rho is ROCK, which is a serine/threonine kinase that binds to the GTP-bound form of Rho. The catalytic kinase domain of ROCK, which comprises conserved motifs characteristic of serine/threonine kinases, is found at the N-terminus. ROCK proteins also have a central coiled-coil domain, which includes a Rho-binding domain (RBD). The C-terminus contains a pleckstrin-homology (PH) domain with an internal cysteine-rich domain. The coiled-coil domain is thought to interact with other alpha helical proteins. The RBD, located within the coiled-coil domain, interacts with activated Rho GTPases, including RhoA, RhoB, and RhoC. The PH domain is thought to interact with lipid mediators such as arachidonic acid and sphingosylphosphorylcholine, and may play a role in protein localization. Interaction of the PH domain and RBD with the kinase domain results in an auto-inhibitory loop. In addition, the kinase domain is involved in binding to RhoE, which is a negative regulator of ROCK activity.

The ROCK family includes ROCK1 (also known as ROK-beta or p160ROCK) and ROCK2 (also known as ROK-alpha). ROCK1 is about 1354 amino acids in length and ROCK2 is about 1388 amino acids in length. The amino acid sequences of human ROCK1 and human ROCK2 can be found at UniProt Knowledgebase (UniProtKB) Accession Number Q13464 and 075116, respectively. The nucleotide sequences of human ROCK1 and ROCK2 can be found at GenBank Accession Number NM_005406.2 and NM_004850, respectively. The nucleotide and amino acid sequences of ROCK1 and ROCK2 proteins from a variety of animals can be found in both the UniProt and GenBank databases.

Although both ROCK isoforms are ubiquitously expressed in tissues, they exhibit differing intensities in some tissues. For example, ROCK2 is more prevalent in brain and skeletal muscle, while ROCK1 is more abundant in liver, testes and kidney. Both isoforms are expressed in vascular smooth muscle and heart. In the resting state, both ROCK1 and ROCK2 are primarily cytosolic, but are translocated to the membrane upon Rho activation. Rho-dependent ROCK activation is highly cell-type dependent, and ROCK activity is regulated by several different mechanisms including changes in contractility, cell permeability, migration and proliferation to apoptosis. Several ROCK substrates have been identified (see e.g., Hu and Lee, Expert Opin. Ther. Targets 9:715-736 (2005); Loirand et al, Cir. Res. 98:322-334 (2006); and Riento and Ridley, Nat. Rev. Mol. Cell Bioi. 4:446-456 (2003) all of which are incorporated by reference). In some instances, ROCK phosphorylates LIM kinase and myosin light chain (MLC) phosphatase after being activated through binding of GTP-bound Rho.

Inhibiting the activity of Rho kinase (e.g., Rho-associated protein kinase) may include reducing the activity, reducing the function, or reducing the expression of at least one of ROCK1 or ROCK2. The activity, function or expression may be completely suppressed (i.e., no activity, function or expression); or the activity, function or expression may be lower in treated versus untreated cells. In some embodiments, inhibiting the activity of Rho kinase (e.g., Rho-associated protein kinase) involves blocking an upstream effector of a ROCK1 and/or ROCK2 pathway, for example GTP-bound Rho, such that ROCK1 and/or ROCK2 are not activated or its activity is reduced compared to untreated cells. Other upstream effectors include but are not limited to, integrins, growth factor receptors, including but not limited to, TGF-beta and EGFR, cadherins, G protein coupled receptors and the like. In some embodiments, inhibiting the activity of Rho kinase (e.g., Rho-associated protein kinase)

involves blocking the activity, function or expression of downstream effector molecules of activated ROCK1 and/or ROCK2 such that ROCK1 and/or ROCK2 cannot propagate any signal or can only propagate a reduced signal compared to untreated cells. Downstream effectors include but are not limited to, vimentin, LIMK, Myosin light chain kinase, NHEI, cofilin and the like.

In some embodiments, inhibiting the activity of Rho kinase (e.g., Rho-associated protein kinase) may comprise the use of one or more Rho kinase inhibitors (e.g., one or more Rho-associated protein kinase inhibitors). Rho kinase inhibitors (e.g., Rho-associated protein kinase inhibitors) may include one or more small molecule Rho kinase inhibitors (e.g., one or more small molecule Rho-associated protein kinase inhibitors). Examples of molecule Rho kinase inhibitors (e.g., Rho-associated protein kinase inhibitors) include, for example, Y-27632 ((R)-(+)-trans-4-(1-Aminoethyl)-N-(4-Pyridyl)cyclohexanecarboxamide dihydrochloride), SR 3677 (N-[2-[2-(Dimethylamino)ethoxy]-4-(1H-pyrazol-4-yl)phenyl-2,3-dihydro-1,4-benzodioxin-2-carboxamide di hydrochloride), thiazovivin (N-Benzyl-[2-(pyrimidin-4-yl)amino]thiazole-4-carboxamide), HA1100 hydrochloride (1-[(1,2-Dihydro-1-oxo-5-isoquinolinyl) sulfonyl]hexahydro-1H-1,4-diazepine hydrochloride), HA1077 (fasudil hydrochloride), and GSK-429286 (4-[4-(Trifluoromethyl)phenyl]-N-(6-Fluoro-1H-indazol-5-yl)-2-methyl-6-oxo-1,4,5,6-tetrahydro-3-pyridinecarboxamide), each of which is commercially available. Additional small molecule Rho kinase inhibitors (e.g., small molecule Rho-associated protein kinase inhibitors) include those described, for example, in International Patent Application Publication Nos. WO 03/059913, WO 03/064397, WO 05/003101, WO 04/112719, WO 03/062225 and WO 03/062227, and described in U.S. Pat. Nos. 7,217,722 and 7,199,147, and U.S. Patent Application Publication Nos. 2003/0220357, 2006/0241127, 2005/0182040 and 2005/0197328, the contents of all of which are incorporated by reference.

p21-Activated Kinase (PAK) Inhibitors

In some embodiments, a method herein comprises inhibiting the activity of p21-activated kinase (PAK) in cultured epithelial cells. PAK proteins, a family of serine/threonine p21-activated kinases, include PAK1, PAK2, PAK3 and PAK4, and generally function to link the Rho family of GTPases to cytoskeleton reorganization and nuclear signaling. These proteins are targets for Cdc42 and Rac and may function in various biological activities. PAK1, for example, can regulate cell motility and morphology. In some embodiments, a method herein comprises inhibiting the activity of PAK1 in cultured epithelial cells.

In some embodiments, a cell culture medium comprises one or more PAK1 inhibitors. In some embodiments, a PAK1 inhibitor binds to a PAK1 protein. In some embodiments, a PAK1 inhibitor binds to one or more PAK1 activators (e.g., Cdc42, Rac). In some embodiments, a PAK1 inhibitor binds to one or more downstream effectors of PAK1. In some embodiments, a PAK1 inhibitor binds to a PAK1 protein and one or more PAK1 activators (e.g., Cdc42, Rac). In some embodiments, a PAK1 inhibitor disrupts one or more PAK1-activator interactions. In some embodiments, a PAK1 inhibitor disrupts one or more PAK1-effector interactions. In some embodiments, a PAK1 inhibitor targets an autoregulatory mechanism and promotes the inactive conformation of PAK1.

PAK1 inhibitors may include one or more small molecule PAK1 inhibitors. PAK1 inhibitors may include, for example, IPA3 (1,1'-Dithiodi-2-naphthtol), AG-1478 (N-(3-Chlorophenyl)-6,7-dimethoxy-4-quinazolinanine), FRAX597 (6-[2-chloro-4-(1,3-thiazol-5-yl)phenyl]-8-ethyl-2-[4-(4-methylpiperazin-1-yl)anilino]pyrido[2,3-d]pyrimidin-7-one), FRAX486 (6-(2,4-Dichlorophenyl)-8-ethyl-2-[[3-fluoro-4-(1-piperazinyl)phenyl]amino]pyrido[2,3-d]pyrimidin-7(8H)-one), and PF-3758309 ((S)—N-(2-(dimethylamino)-1-phenylethyl)-6,6-dimethyl-3-((2-methylthieno[3,2-d]pyrimidin-4-yl)amino)-4,6-dihydropyrrolo[3,4-c]pyrazole-5(1H)-carboxamide). In some embodiments, the PAK1 inhibitor is IPA3.

Myosin II Inhibitors

In some embodiments, a method herein comprises inhibiting activity of myosin II (e.g., non-muscle myosin II (NM II)) in cultured epithelial cells. Myosin II (e.g., non-muscle myosin II (NM II)) is a member of a family of ATP-dependent motor proteins and plays a role in muscle contraction and other motility processes (e.g., actin-based motility). Non-muscle myosin II (NM II) is an actin-binding protein that has actin cross-linking and contractile properties and is regulated by the phosphorylation of its light and heavy chains. Owing to its position downstream of convergent signaling pathways, non-muscle myosin II (NM II) is involved in the control of cell adhesion, cell migration and tissue architecture. In higher eukaryotes, non-muscle myosin II is activated by phosphorylation of its regulatory light chain (MLC) at Ser19/Thr18. MLC phosphorylation controls both the assembly of the actomyosin contractile apparatus and its contractility. Two groups of enzymes generally control MLC phosphorylation. One group includes kinases that phosphorylate MLC (MLC kinases), promoting activity, and the other is a phosphatase that dephosphorylates MLC, inhibiting activity. Several kinases can phosphorylate MLC at Ser19/Thr18 in vitro and, in some cases, in vivo. These include, for example, MLCK, ROCK, PAK (p21-activated kinase), citron kinase, ILK (integrin-linked kinase), MRCK (myotonic dystrophyprotein kinase-related, cdc42-binding kinase) and DAPKs (death-associated protein kinases including ZIPK). The major myosin phosphatase present in smooth and non-muscle cells includes three subunits: a large subunit of w 130 kDa (referred to as the myosin phosphatase targeting subunit MYPT1 (also called M130/133, M110 or MBS)), a catalytic subunit of 38 kDa (the 6 isoform of type 1 protein phosphatase, PP1c) and a small subunit of 20 kDa. Rho-associate protein kinase (ROCK) can activate myosin II by inhibiting MYPT1 and by directly phosphorylating MLC. PAK1 can activate myosin II through the phosphorylation of atypical protein kinase C (aPKC).

In some embodiments, a cell culture medium comprises one or more myosin II inhibitors (e.g., non-muscle myosin II (NM II) inhibitors). In some embodiments, a myosin II inhibitor binds to a myosin II protein. In some embodiments, a myosin II inhibitor binds to a myosin head structure. In some embodiments, a myosin II inhibitor binds to the myosin-ADP-$P_i$ complex. In some embodiments, a myosin II inhibitor disrupts myosin II ATPase activity. In some embodiments, a myosin II inhibitor competes with ATP for binding to myosin II. In some embodiments, a myosin II inhibitor competes with nucleotide binding to myosin subfragment-1. In some embodiments, a myosin II inhibitor disrupts myosin II-actin binding. In some embodiments, a myosin II inhibitor disrupts the interaction of the myosin head with actin and/or substrate. In some embodiments, a myosin II inhibitor disrupts ATP-induced actomyosin dissociation. In some embodiments, a myosin II inhibitor interferes with a phosphate release process. In some embodiments, a myosin II inhibitor prevents rigid actomyosin cross-linking.

Myosin II inhibitors (e.g., non-muscle myosin II (NM II) inhibitors) may include one or more small molecule myosin II inhibitors (e.g., small molecule non-muscle myosin II (NM II) inhibitors). Myosin II inhibitors may include, for example, blebbistatin ((±)-1,2,3,3a-Tetrahydro-3a-hydroxy-6-methyl-1-phenyl-4H-pyrrolo[2,3-b]quinolin-4-one)and analogs thereof (e.g., para-nitroblebbistatin, (S)-nitroBlebbistatin, S-(−)-7-desmethyl-8-nitro blebbistatin, and the like), BTS (N-benzyl-p-toluene sulphonamide), and BDM (2,3-butanedione monoxime). In some embodiments, the myosin II inhibitor is blebbistatin.

Subsequent Environments

In some embodiments, the cells may be removed from the culture conditions described herein after a certain amount of time and placed into a subsequent environment. A subsequent environment may be an environment that promotes differentiation of the cells. A subsequent environment may be an in vivo environment that is similar or identical to the organ or tissue from which the cells were originally derived (e.g., an autologous implant). A subsequent environment may be an in vitro or ex vivo environment that closely resembles certain biochemical or physiological properties of the organ or tissue from which the cells were originally derived. A subsequent environment may be a synthetic environment such that factors known to promote differentiation in vitro or ex vivo are added to the cell culture. In some embodiments, cells are placed into a subsequent environment that is specific to stimulate differentiation of cells into the cells of the organ or tissue from which the cells were originally derived.

Any of the components described above may be present or absent in a subsequent environment. In some embodiments, one or more inhibitors described above is absent in a subsequent environment. For example, one or more of a TGF-beta inhibitor (e.g., a TGF-beta signaling inhibitor), a ROCK inhibitor, a PAK1 inhibitor, a myosin II inhibitor (e.g., non-muscle myosin II (NM II) inhibitor), and a retinoic acid signaling inhibitor may be absent in a subsequent environment.

In some embodiments, the cells are placed into a subsequent environment where TGF-beta signaling is not inhibited. In some embodiments, the cells are placed into a subsequent environment where ROCK is not inhibited. In some embodiments, the cells are placed into a subsequent environment where PAK1 is not inhibited. In some embodiments, the cells are placed into a subsequent environment where myosin II (e.g., non-muscle myosin II (NM II)) is not inhibited. In some embodiments, the cells are placed into a subsequent environment where retinoic acid signaling is not inhibited. In some embodiments, the cells are placed into a subsequent environment where TGF-beta signaling and ROCK are not inhibited. In some embodiments, the cells are placed into a subsequent environment where TGF-beta signaling and PAK1 are not inhibited. In some embodiments, the cells are placed into a subsequent environment where TGF-beta signaling and myosin II (e.g., non-muscle myosin II (NM II)) are not inhibited. In some embodiments, the cells are placed into a subsequent environment where TGF-beta signaling and retinoic acid signaling are not inhibited.

In some embodiments, the cells maintain or regain one or more native functional characteristics after placement into the cell culture environment where TGF-beta signaling is not inhibited. In some embodiments, the cells maintain or regain one or more native functional characteristics after placement into the cell culture environment where ROCK is not inhibited. In some embodiments, the cells maintain or regain one or more native functional characteristics after placement into the cell culture environment where PAK1 is not inhibited. In some embodiments, the cells maintain or regain one or more native functional characteristics after placement into the cell culture environment where myosin II (e.g., non-muscle myosin II (NM II)) is not inhibited. In some embodiments, the cells maintain or regain one or more native functional characteristics after placement into the cell culture environment where retinoic acid signaling is not inhibited. In some embodiments, the cells maintain or regain one or more native functional characteristics after placement into the cell culture environment where TGF-beta signaling and ROCK are not inhibited. In some embodiments, the cells maintain or regain one or more native functional characteristics after placement into the cell culture environment where TGF-beta signaling and PAK1 are not inhibited. In some embodiments, the cells maintain or regain one or more native functional characteristics after placement into the cell culture environment where TGF-beta signaling and myosin II (e.g., non-muscle myosin II (NM II)) are not inhibited. In some embodiments, the cells maintain or regain one or more native functional characteristics after placement into the cell culture environment where TGF-beta signaling and retinoic acid signaling are not inhibited.

Encapsulation of Spheroids in Hydrogel

In some embodiments, cells or spheroids are encapsulated in hydrogel and cultured in a container. A hydrogel used for encapsulation may include, for example, alginate, hyaluronic acid/collagen hydrogel such as HyStem®-C, Matrigel™, and the like. The hydrogel generally allows sufficient transport of oxygen, nutrients, metabolic wastes, and secretory products to and from the spheroids to the bulk media, without allowing the cells to leak out of the capsules. Encapsulation may offer efficient protection for the spheroids and may facilitate subsequent downstream processes. Encapsulation of spheroids could prevent aggregation of individual spheroids into a bulk mass, for example. Encapsulation also may increase spheroid density in culture containers and could increase the yield of biological factors secreted by the spheroids.

For in vivo use of encapsulated spheroids, encapsulation may prevent macromolecules (e.g., antibodies) or immune cells from attacking the spheroids. This may allow the use of allogeneic spheroids in the recipient without systemic immune suppression. Encapsulation of spheroids also may allow for easy removal of the spheroids from the subject when necessary.

Certain methods described herein may be performed in conjunction with methods and compositions described, for example, in International Patent Application Publication No. WO2016/161192; International Patent Application Publication No. WO2017/044454; U.S. Patent Application Publication No. US20170073635; U.S. Patent Application Publication No. US20170029779; U.S. Patent Application Publication No. US20170029780; U.S. Patent Application Publication No. US20180002669; U.S. Patent Application Publication No. US20180051258; U.S. Patent Application Publication No. US20180208899; U.S. Patent Application Publication No. US20180208900; U.S. Pat. Nos. 9,790,471; and 9,963,680, the entire content of each is incorporated herein by reference, including all text, tables, equations and drawings.

EXAMPLES

The examples set forth below illustrate certain embodiments and do not limit the technology.

Example 1: Preliminary Epithelial Cell Culture Analysis

In this example, preliminary epithelial cell culture analysis was performed on non-aggregated (e.g., single cell) airway epithelial cells and the results are described.

Epithelial Cells Cultured in or on Top of Matrigel™

Figure 2:
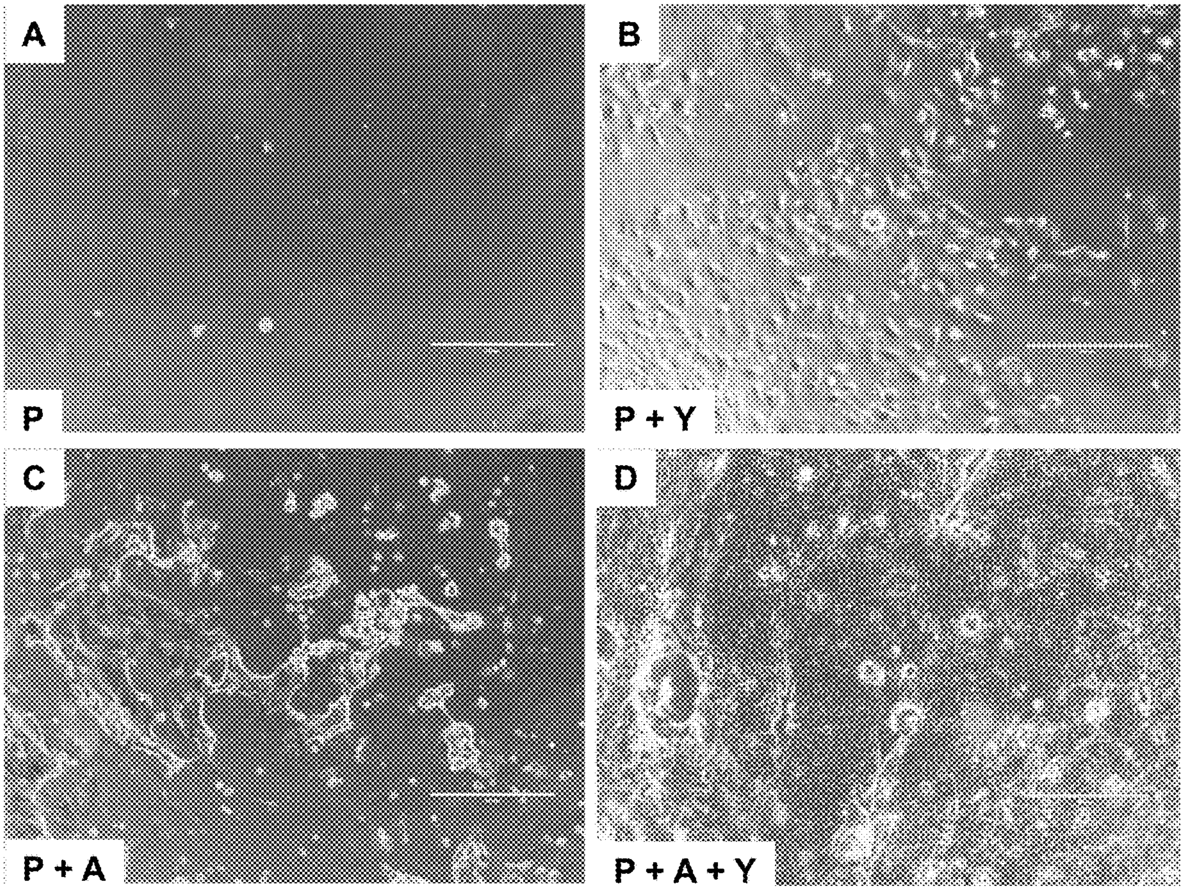
FIG. 2 shows airway epithelial cells formed a continuous epithelium sheet in submersion in the presence of both A 83-01 and Y-27632. Normal human bronchial epithelial cells (HBEC; passage 11 (P11), population doubling (PD)-30) were seeded on top of 25% Matrigel™ (BD Biosciences) in 24-well plate and cultured in submersion with different media. Panel A shows cells cultured in PneumaCult™-ALI medium (P; STEMCELL Technologies). Panel B shows cells cultured in PneumaCult™-ALI medium with 5 μM Y-27632 (P+Y). Panel C shows cells cultured in PneumaCult™-ALI medium with 1 μM A 83-01 (P+A). Panel D shows cells cultured in PneumaCult™-ALI medium with 1 μM A83-01 and 5 μM Y-27632 (P+A+Y). By day 27, only cells cultured in the presence of both A and Y compounds formed continuous epithelium in the submerged format.
Figure 3:
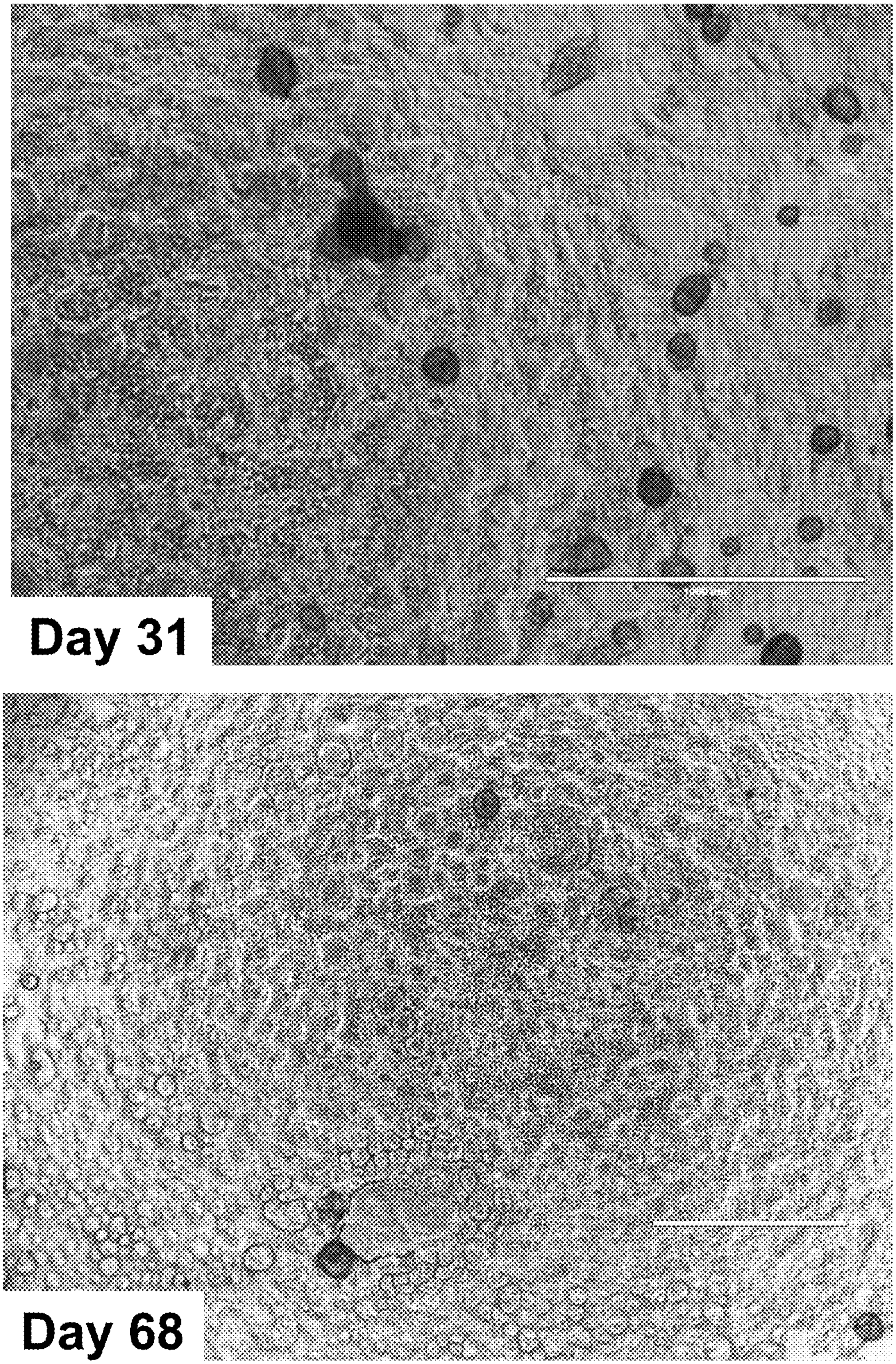
FIG. 3 shows an epithelium sheet formed by airway epithelial cells under submersion conditions continued to survive in PneumaCult™-ALI with A83-01 and Y-27632 (P+A+Y) for over 2 months.

A conventional method to induce airway basal epithelial cells to grow/differentiate into mucociliary lineages is to culture the cells under air-liquid-interface (ALI) conditions. It was reported that submersion in medium creates a hypoxic environment that represses the differentiation of multiciliated cells (see e.g., Gerovac et al., Submersion and Hypoxia Inhibit Ciliated Cell Differentiation in a Notch-Dependent Manner; Am J Respir Cell Mol Biol. (2014) 51(4):516-25). However, airway epithelial cells did grow into mucociliary lineages under submersion conditions in the presence of A 83-01 and Y-27632. Specifically, airway epithelial cells formed a continuous epithelium sheet in submersion in the presence of both A 83-01 and Y-27632 (see FIG. 2). Normal human bronchial epithelial cells (HBEC; passage 11 (P11), population doubling (PD)-30) were seeded on top of 25% Matrigel™ (BD Biosciences) in 24-well plate and cultured with different media. Panel A of FIG. 2 shows cells cultured in PneumaCult™-ALI medium (P; STEMCELL Technologies). Panel B of FIG. 2 shows cells cultured in PneumaCult™-ALI medium with 5 μM Y-27632 (P+Y). Panel C of FIG. 2 shows cells cultured in PneumaCult™-ALI medium with 1 μM A 83-01 (P+A). Panel D of FIG. 2 shows cells cultured in PneumaCult™-ALI medium with 1 μM A83-01 and 5 μM Y-27632 (P+A+Y). By day 27, only cells cultured in the presence of both A and Y compounds formed continuous epithelium in the submerged format. The epithelium sheet formed by airway epithelial cells under submersion conditions continued to survive in PneumaCult™-ALI with 1 μM A83-01 and 5 μM Y-27632 (P+A+Y) for over 2 months (see FIG. 3). Multiciliated cells could be found in the continuous airway epithelium sheet, with the apical side faced up (see FIG. 4, panel B). This indicated that the differentiation of multiciliated cells proceeded in submersion when both A 83-01 and Y-27632 (A+Y) were added to the medium.

Figure 4:
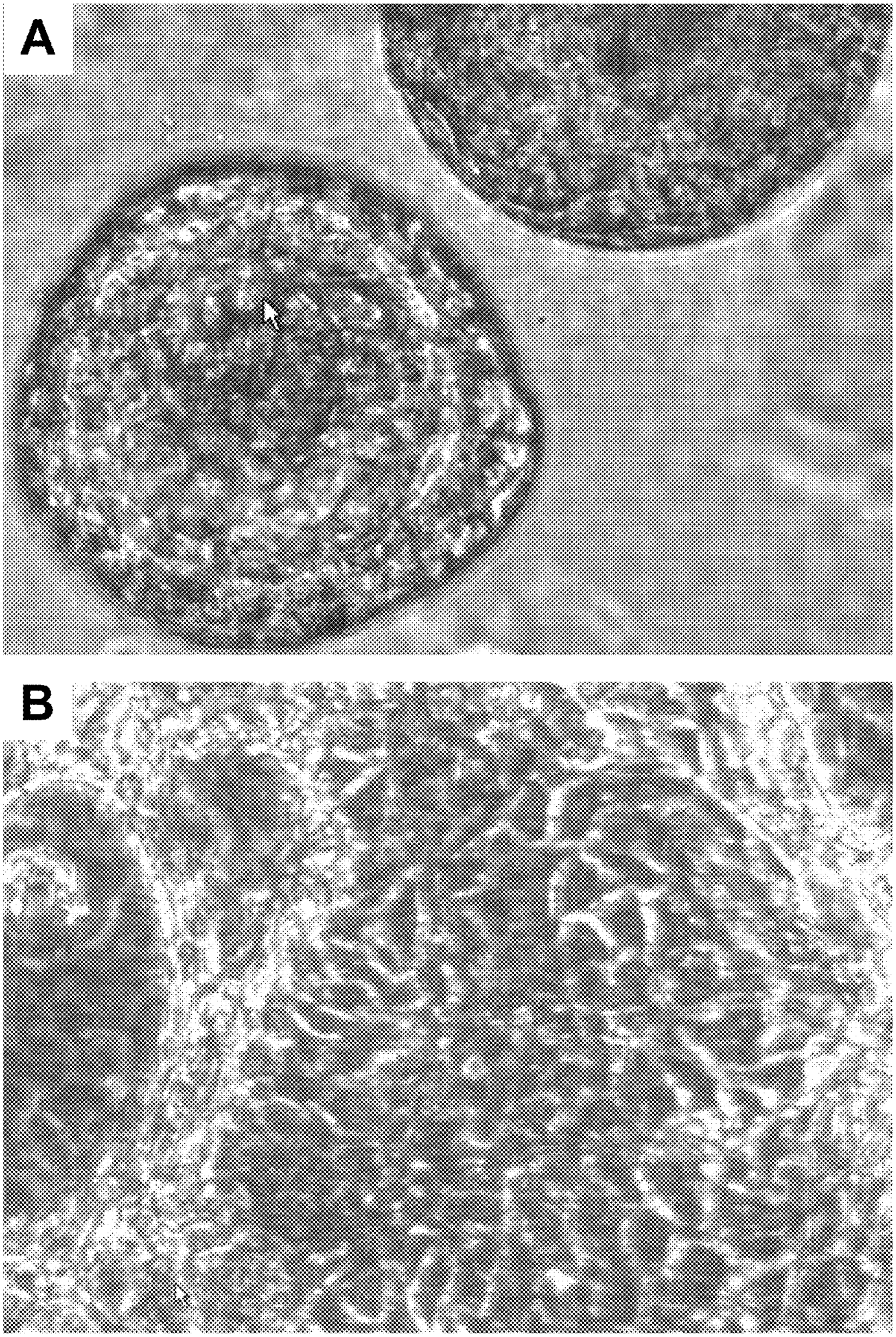
FIG. 4 shows airway epithelial cells seeded on top of Matrigel and cultured in PneumaCult™-ALI supplemented with A83-01 and Y-27632 (P+A+Y) for at least 30 days. Panel A shows spheres (also referred to as bronchospheres) formed by individual airway epithelial cells which were entrapped in Matrigel™. The apical side, where spontaneous beating of the cilia could be seen, faced inwards. Panel B shows multiciliated cells could also be found in the continuous airway epithelium sheet formed on top of Matrigel, with the apical side faced up. This indicated that the differentiation of multiciliated cells proceeded even in submersion when both A 83-01 and Y-27632 (A+Y) were added to the medium.

In another experiment, individual airway epithelial cells formed bronchospheres when they were embedded in Matrigel™ (see FIG. 4, panel A). Airway epithelial cells were cultured in PneumaCult™-ALI supplemented with 1 μM A83-01 and 5 μM Y-27632 (P+A+Y) for at least 30 days. Panel A of FIG. 4 shows spheres (also referred to as bronchospheres) formed by individual airway epithelial cells which were embedded in Matrigel™. The apical side, where spontaneous beating of the cilia could be seen, faced inwards.

Epithelial Cells Cultured in Hydrogel

Figure 5:
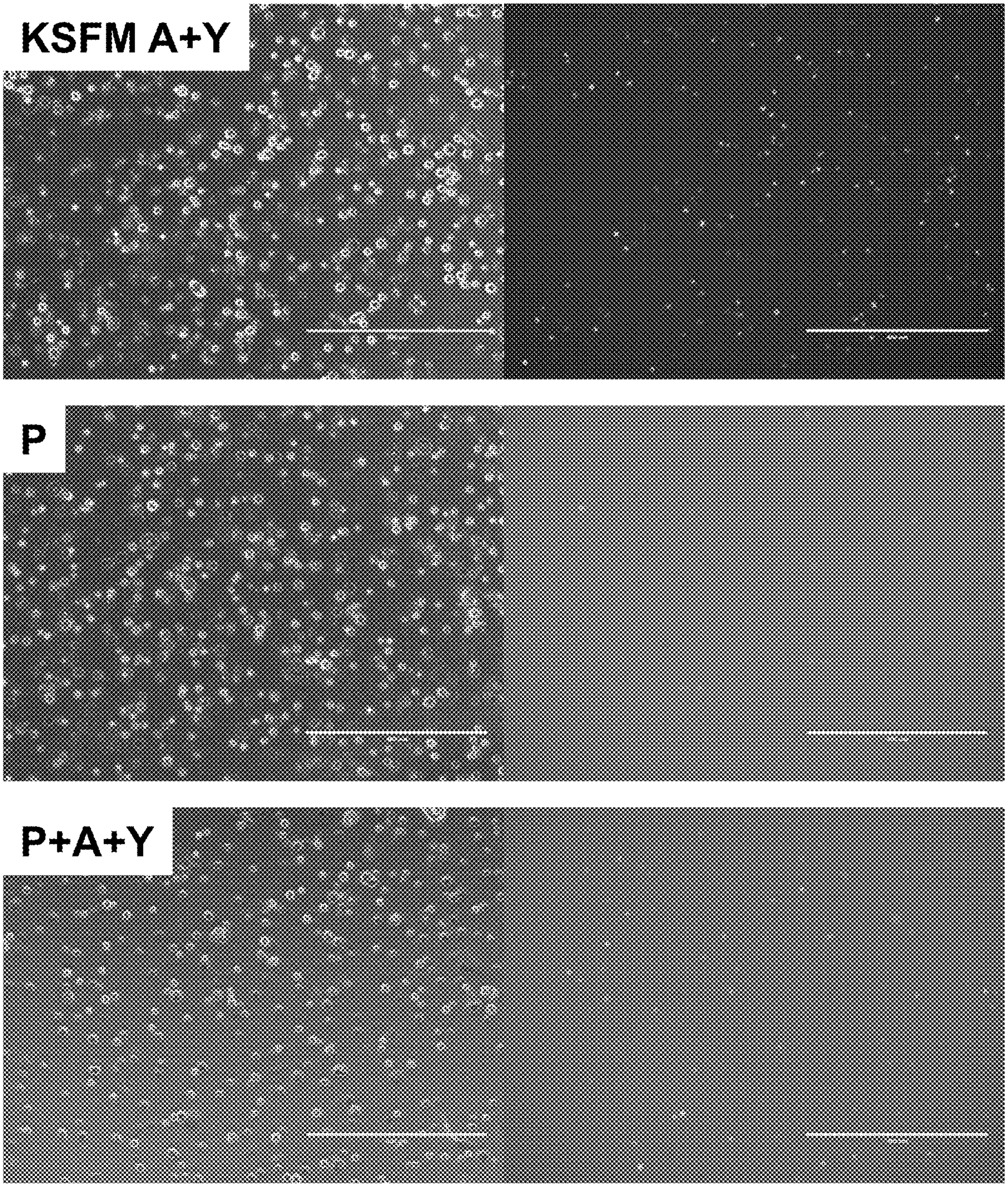
FIG. 5 shows airway epithelial cells expressing GFP encapsulated in HyStem®-C hydrogel and cultured in submersion in Keratinocyte-SFM (KSFM; Gibco/Thermo Fisher 17005-042) supplemented with A 83-01 and Y-27632 (KSFM A+Y), PneumaCult™-ALI (P), or PneumaCult™-ALI supplemented with A83-01 and Y-27632 (P+A+Y) media. By day 7, most of the cells cultured in PneumaCult™-ALI medium were dead (shown by the loss of GFP expression). Some cells survived (shown as GFP-positive) in KSFM A+Y or P+A+Y medium, but they remained as single cells, and did not grow into spheres.
Figure 6:
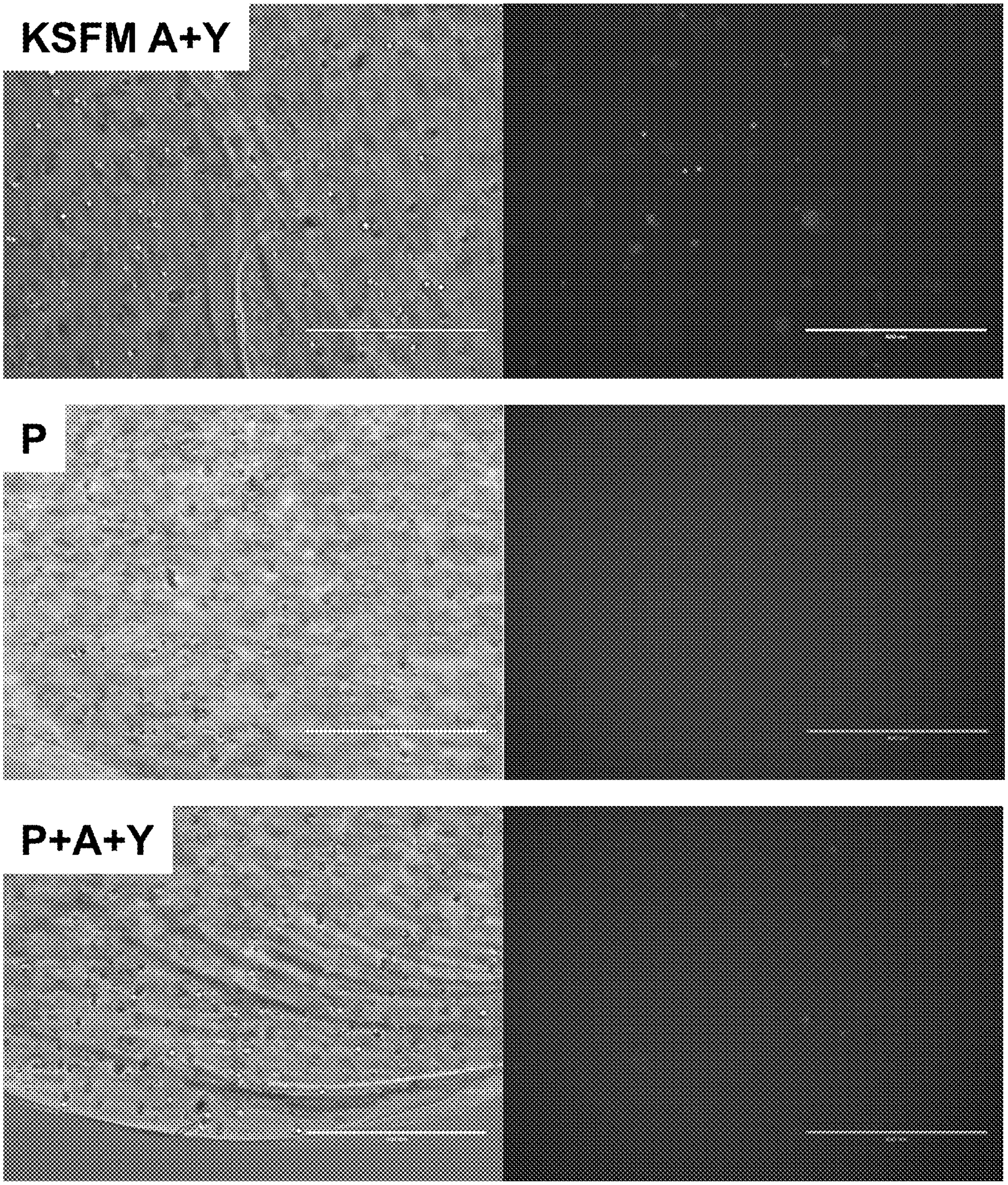
FIG. 6 shows airway epithelial cells expressing GFP encapsulated in alginate and cultured in submersion in Keratinocyte-SFM (KSFM; Gibco/Thermo Fisher 17005-042) supplemented with A 83-01 and Y-27632 (KSFM A+Y), PneumaCult™-ALI (P), or PneumaCult™-ALI supplemented with A83-01 and Y-27632 (P+A+Y) media. By day 7, most of the cells cultured in PneumaCult™-ALI medium were dead (shown by the loss of GFP expression). Some cells survived (shown as GFP-positive) in KSFM A+Y or P+A+Y medium, but they remained as single cells, and did not grow into spheres.

Airway epithelial cells expressing GFP (421/GFP, 20,000 cells) were encapsulated as single cell suspension in HyStem®-C hydrogel (ESI BIO, HyStem®-C Hydrogel Kit, Cat #GS313), or alginate (1%, VWR, 200005-674) and cultured in submersion in Keratinocyte-SFM (Gibco/Thermo Fisher 17005-042) supplied with prequalified human recombinant Epidermal Growth Factor 1-53 (EGF 1-53, used at 0.5 ng/mL) and Bovine Pituitary Extract (BPE, used at 30 μg/mL), and supplemented with 1 μM A 83-01, 5 μM Y-27632 and 3 μM isoproterenol (referred to herein as KSFM A+Y); PneumaCult™-ALI (P); or PneumaCult™-ALI supplemented with 1 μM A83-01 and 5 μM Y-27632 (P+A+Y) media. By day 7, most of the cells were dead in PneumaCult™-ALI medium as shown by the loss of GFP expression (see FIGS. 5 and 6). Some cells survived (shown as GFP-positive) in KSFM A+Y or P+A+Y medium, but they remained as single cells, and did not grow into spheres. This data indicates that unlike Matrigel™, HyStem®-C hydrogel or alginate lacks factors that promote cell attachment and survival. Thus, single airway epithelial cells did not form bronchospheres when they were encapsulated in HyStem-C hydrogel, or alginate.

Example 2: Apical Side Outward-Oriented (ASO) Epithelial Spheroids Generated from Cellular Aggregates In this example, apical side outward-oriented (ASO) epithelial spheroids were generated from cellular aggregates. Epithelial cells were grown on a basement membrane core, and the basal side of the epithelial cells attached to the basement membrane. The core was prepared by forming cellular aggregates. Since the epithelial cells produce most of the proteins found in the basement membrane, a core was produced by aggregating epithelial cells and allowing the epithelial cells to produce basement membrane proteins, including laminins and collagens. The cell aggregates were then cultured in suspension to prevent adherence to the culture vessels. Eventually the cells grew into spheroids with the apical side facing outwards. Thus, pre-aggregating airway epithelial cells and then culturing the aggregates in suspension lead to the formation of ASO epithelial spheroids.

Figure 7:
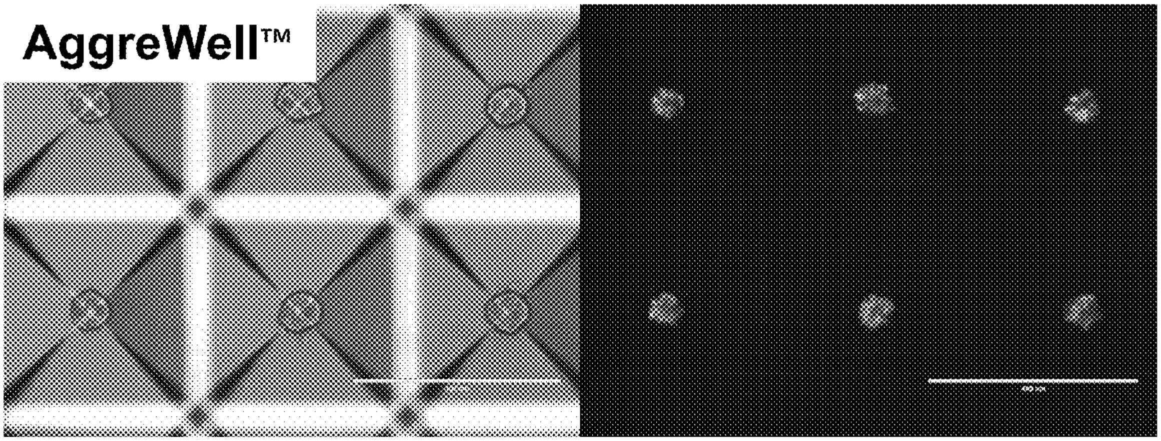
FIG. 7 shows aggregated airway epithelial cells expressing GFP before encapsulation in alginate, HyStem®-C hydrogel, or Matrigel™.

Specifically, airway epithelial cells expressing GFP (421/GFP, 100 cells or 50 cells) were induced to form aggregates using AggreWell™400 (STEMCELL Technologies, 34450) and cultured overnight in PneumaCult™-ALI supplemented with 1 μM A83-01 and 5 μM Y-27632 (P+A+Y) media; or Keratinocyte-SFM (Gibco/Thermo Fisher 17005-042) supplied with prequalified human recombinant Epidermal Growth Factor 1-53 (EGF 1-53, used at 0.5 ng/mL) and Bovine Pituitary Extract (BPE, used at 30 μg/mL), and supplemented with 1 μM A 83-01, 5 μM Y-27632 and 3 μM isoproterenol (KSFM A+Y)+1.5 mM $CaCl_2$. Aggregated airway epithelial cells expressing GFP are shown in FIG. 7.

Figure 8:
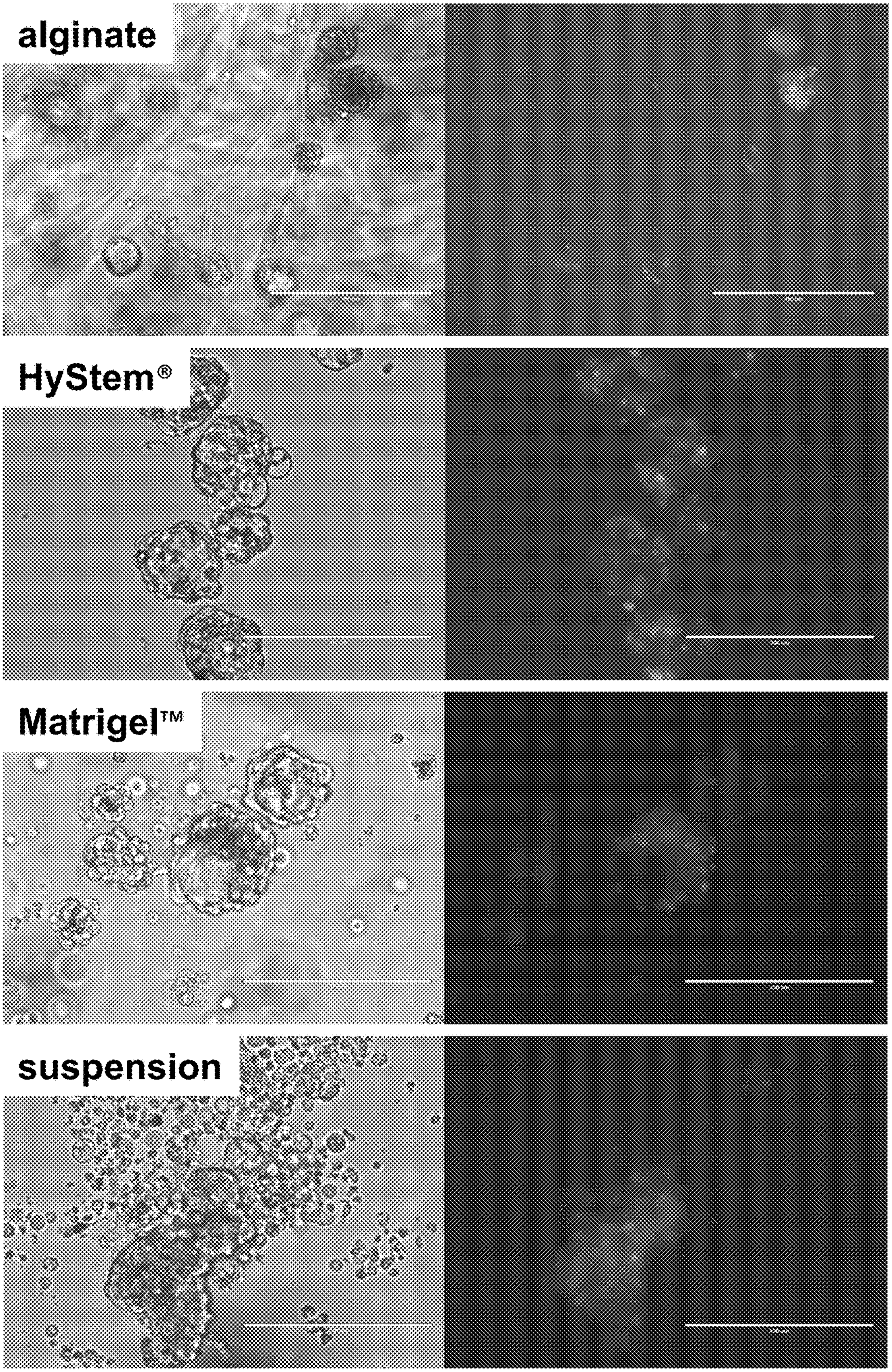
FIG. 8 shows pre-aggregating airway epithelial cells expressing GFP before encapsulation in alginate, HyStem®-C hydrogel, or Matrigel™ improved cell survival. By day 14, cells grew into hollow spheres with the apical side facing outwards. Airway cell aggregates cultured in liquid suspension in an ultra-low attachment plate also grew into spheres with the apical side facing outwards.
Figure 9:
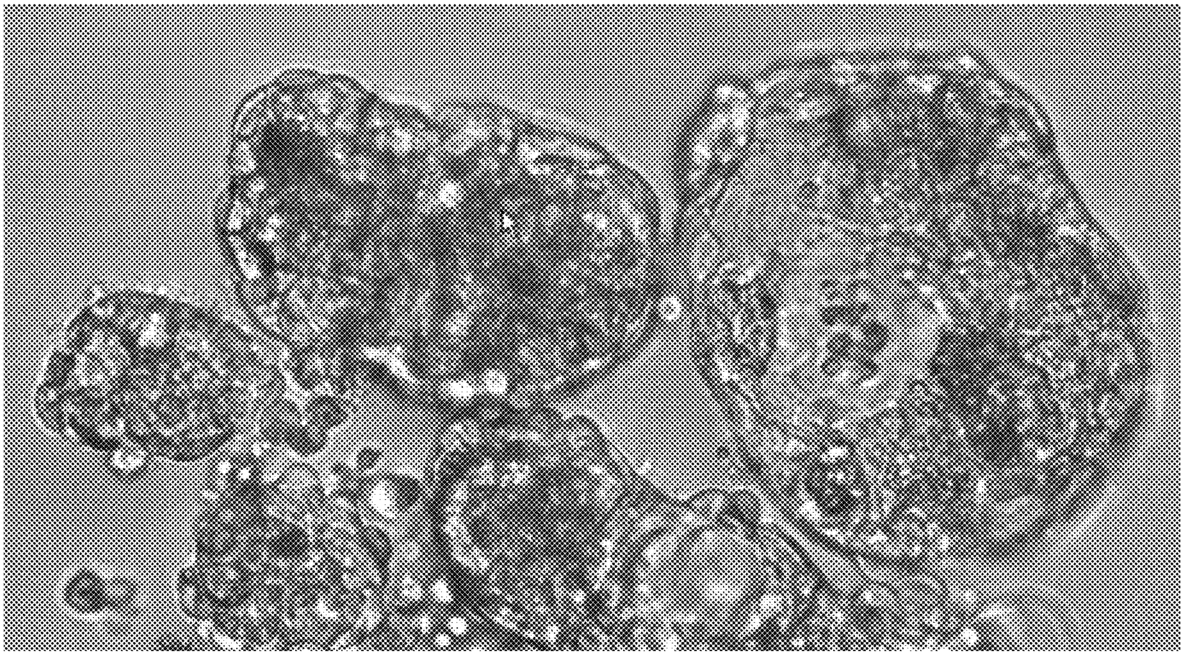
FIG. 9 shows airway epithelial cells expressing GFP which were pre-aggregated in AggreWell™400 and cultured in suspension in an ultra-low attachment well in PneumaCult™-ALI supplemented with A83-01 and Y-27632 (P+A+Y) medium. After 21 days, the aggregates grew into spheres with the apical side facing outwards.

The aggregates were then cultured as free-floating spheres in an ultra-low attachment plate (Corning, 3471) in P+A+Y medium. By day 14, cells grew into spheres with the apical side facing outwards (see FIG. 8, bottom panel). FIG. 9 shows airway epithelial cells expressing GFP which were pre-aggregated in AggreWell™400 and cultured in suspension in an ultra-low attachment well in P+A+Y medium. After 21 days, the aggregates grew into spheres with the apical side facing outwards.

Figure 10A:
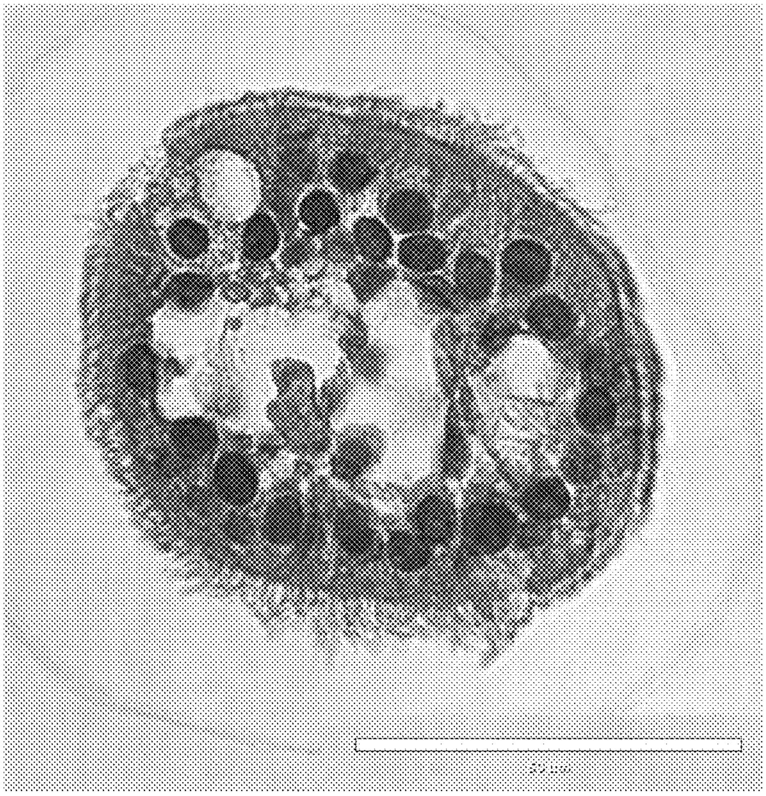
FIG. 10A and FIG. 10B show H&E staining of two ASO (apical side outward-oriented) spheroids made of airway epithelial cells cultured for 3 months in PneumaCult™-ALI supplemented with A83-01 and Y-27632 (P+A+Y) medium. The multiciliated cells are discernable with their cilia facing outwards. The size bar in FIG. 10A
Figure 10B:
Figure 11A:
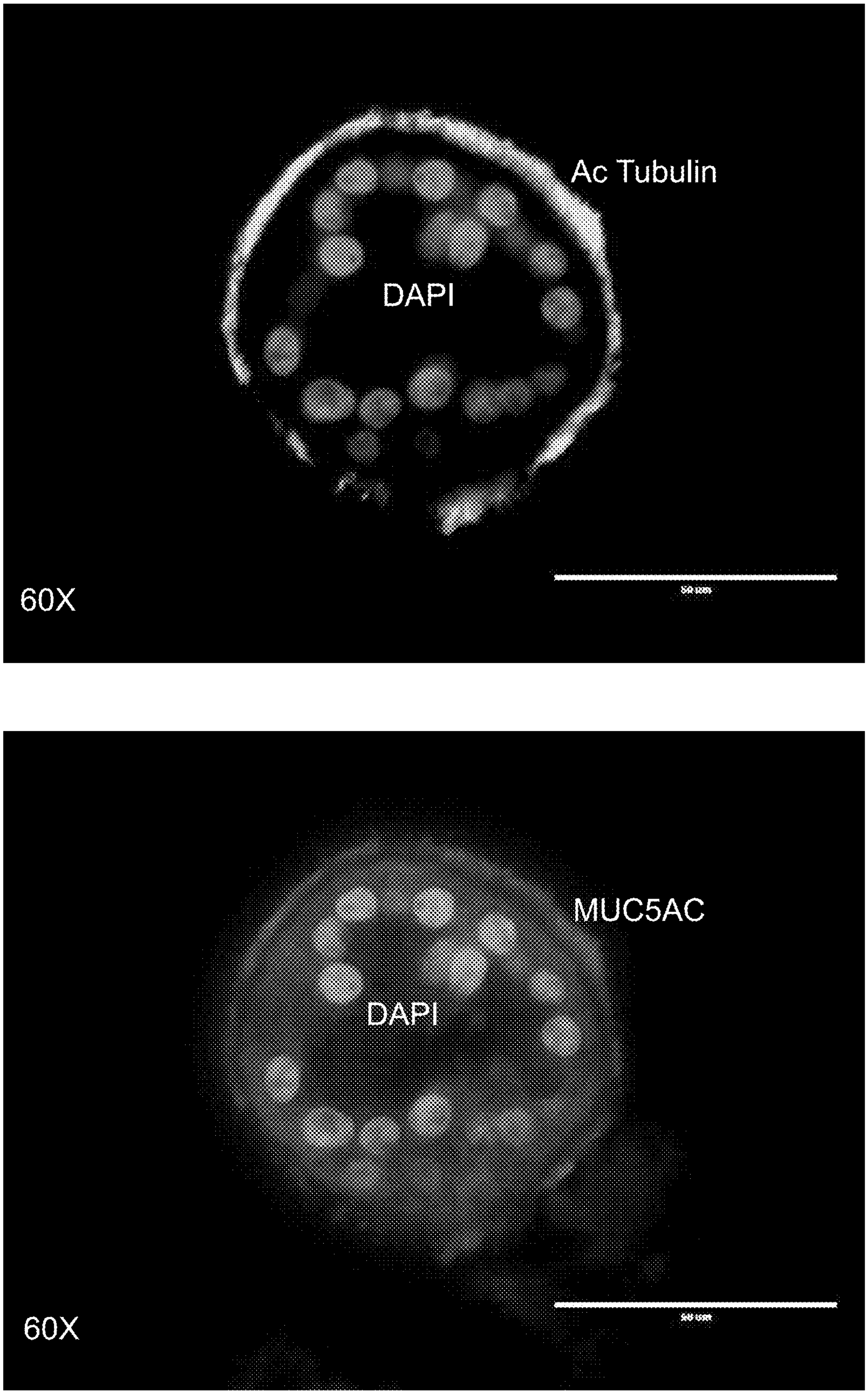
Figure 11B:
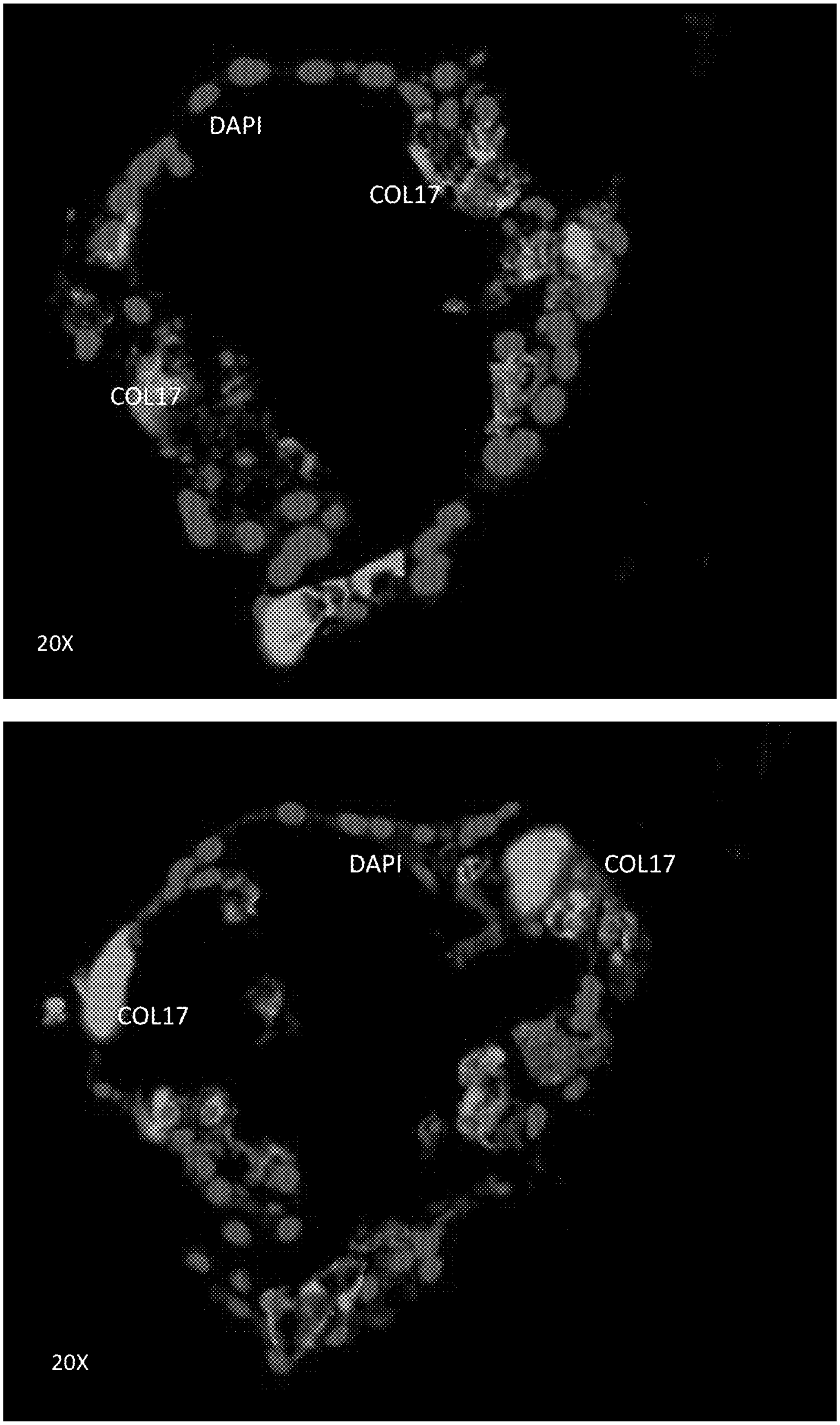
FIG. 11B shows two different ASO spheroids immunostained for expression of Collagen XVII (COL17) protein. Nuclei are stained with DAPI.
Figure 11C:
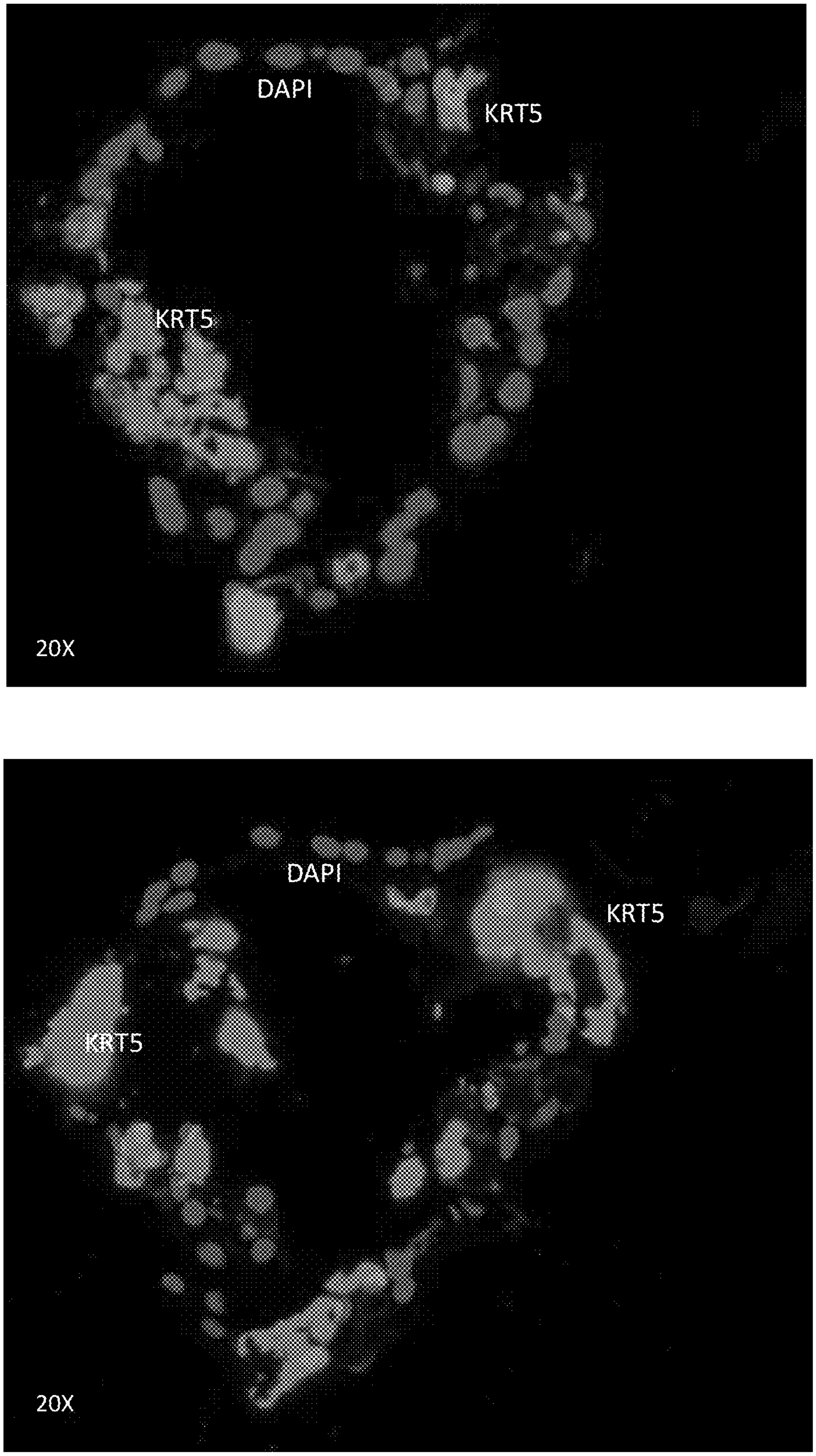
FIG. 11C shows two different ASO spheroids immunostained for expression of Keratin 5 (KRT5) protein. Nuclei are stained with DAPI.

The ASO epithelial spheroids were maintained in suspension culture for at least 3 months, and maintained mature functions such as spontaneous cilia beating. FIG. 10A and FIG. 10B show H&E staining of two ASO (apical side outward-oriented) spheroids made of airway epithelial cells cultured for three months in PneumaCult™-ALI supplemented with A83-01 and Y-27632 (P+A+Y) medium. The multiciliated cells are discernable with their cilia facing outwards. FIGS. 11A-11C show antibody staining of an ASO spheroid made of airway epithelial cells cultured in PneumaCult™-ALI supplemented with A83-01 and Y-27632 (P+A+Y) medium. By day 14, the expanded airway epithelial cells formed ASO spheroids with multiciliated cells (stained with an antibody to acetylated tubulin) and secretory cells (stained with an antibody to mucin 5AC); DAPI was used as nuclear counterstain (FIG. 11A). Expression of Collagen XVII (COL17) protein is shown in FIG.

11B, and expression of Keratin 5 (KRT5) protein is shown in FIG. 11C. Nuclei were stained with DAPI. Both Collagen XVII and Keratin 5 expression is representative of a basal airway epithelial phenotype. In FIG. 11B and FIG. 11C, both Collagen XVII and Keratin 5 protein are localized on the interior side of the spheroid, which is indicative of a basal cell layer oriented toward the lumen of the spheroid and an apical surface oriented toward the outside.

Figure 12:
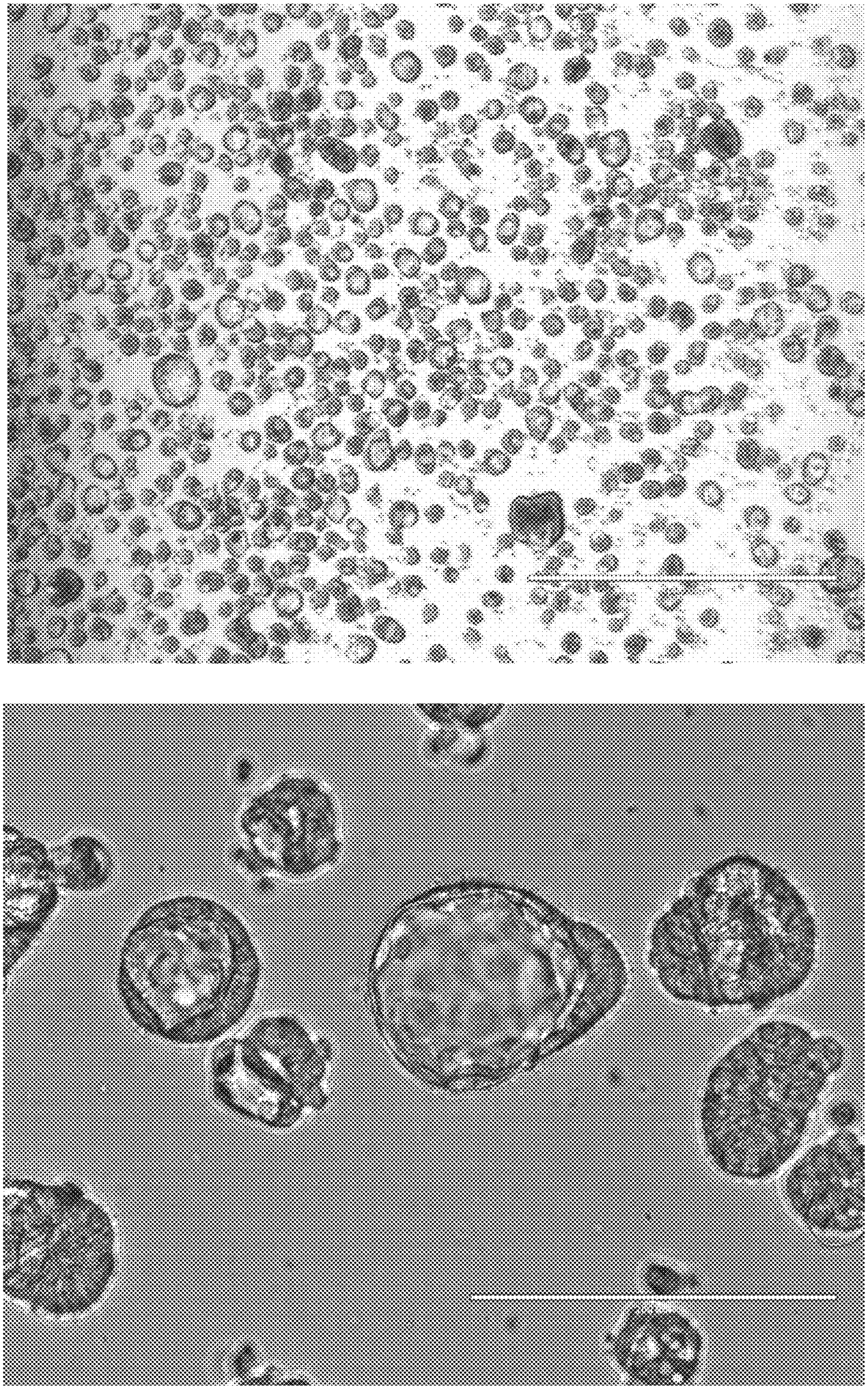
FIG. 12 shows epithelial spheroids cultured in suspension. Top: 21-day old ASO spheroids at 4×. Bottom: 21-day old ASO spheroids at 20×. The size bar for the top panel represents 1000 microns; the size bar for bottom represents 200 microns.

FIG. 12 shows a uniform size distribution for epithelial spheroids cultured in suspension. The ASO spheroids measured between 30-150 microns in diameter with few having diameters outside this range. In certain populations of spheroids, a bell curve size distribution was observed with a median diameter of about 75 microns. In certain populations of spheroids, a bell curve size distribution was observed with a median diameter of about 60 microns.

The ASO epithelial spheroids were cryopreserved in liquid nitrogen storage with P+A+Y+10% FBS+10% DMSO, and thawed according to standard protocol for regular cell cultures. After thawing from liquid nitrogen storage, the ASO epithelial spheroids were cultured in suspension in P+A+Y for at least two weeks and maintained mature function such as spontaneous cilia beating.

Example 3: Apical Side Outward-Oriented (ASO) Epithelial Spheroids Encapsulated in Hydrogel In this example, apical side outward-oriented (ASO) epithelial spheroids were generated from cellular aggregates and encapsulated in hydrogel. Epithelial cells were grown on a basement membrane core, and the basal side of the epithelial cells attached to the basement membrane. The core was prepared by forming cellular aggregates. Since the epithelial cells produce most of the proteins found in the basement membrane, a core was produced by aggregating epithelial cells and allowing the epithelial cells to produce basement membrane proteins, including laminins and collagens. The cell aggregates were then cultured in encapsulation in HyStem®-C, alginate or Matrigel™. Eventually the cells grew into spheroids with the apical side facing outwards. Thus, pre-aggregating airway epithelial cells and then culturing the aggregates in encapsulation in HyStem®-C, alginate or Matrigel™ under culture conditions provided herein lead to the formation of ASO epithelial spheroids.

Specifically, airway epithelial cells expressing GFP (421/GFP, 100 cells or 50 cells) were induced to form aggregates using AggreWell™400 (STEMCELL Technologies, 34450) and cultured overnight in PneumaCult™-ALI supplemented with 1 μM A83-01 and 5 μM Y-27632 (P+A+Y) media; or Keratinocyte-SFM (Gibco/Thermo Fisher 17005-042) supplied with prequalified human recombinant Epidermal Growth Factor 1-53 (EGF 1-53, used at 0.5 ng/mL) and Bovine Pituitary Extract (BPE, used at 30 μg/mL), and supplemented with 1 μM A 83-01, 5 μM Y-27632 and 3 μM isoproterenol (KSFM A+Y)+1.5 mM $CaCl_2$. Aggregated airway epithelial cells expressing GFP before encapsulation in alginate, HyStem®-C hydrogel, or Matrigel™ are shown in FIG. 7.

The aggregates were then encapsulated in HyStem®-C in P+A+Y medium, alginate in P+A+Y medium, or Matrigel™ in P+A+Y medium. Pre-aggregating airway epithelial cells expressing GFP before encapsulation in alginate, HyStem®-C hydrogel, or Matrigel™ improved cell survival. By day 14, cells grew into hollow spheres with the apical side facing outwards (see FIG. 8, top three panels). The ASO epithelial spheroids were cultured in encapsulation in HyStem®-C, alginate or Matrigel™ in P+A+Y medium for more than 1 month, and maintained mature functions such as spontaneous cilia beating.

Example 4: Apical Side Outward-Oriented (ASO) Epithelial Spheroids Generated on Microcarriers In this example, apical side outward-oriented (ASO) epithelial spheroids are generated on a substrate, typically microcarriers or microspheres. Epithelial cells are grown on microspheres or microcarriers comprising basement membrane proteins, and the basal side of the epithelial cells attaches to the basement membrane proteins. The microcarriers can be prepared by coating a substrate (e.g., microspheres or microcarriers such as Corning® Dissolvable Microcarriers, Corning 4979 or 4987) with basement membrane proteins, or extracellular matrix (e.g., Matrigel™).

Specifically, epithelial cells are cultured in the presence of Corning® Dissolvable Microcarriers (Corning 4979 or 4987) coated with basement membrane proteins (e.g., laminins such as LN-511, fibronectin, collagen IV, or Nidogen) or fragments of basement membrane proteins (such as fibronectin-mimetic peptides or laminin-mimetic peptides), or extracellular matrix (e.g., Matrigel™), and are cultured overnight in PneumaCult™-ALI supplemented with 1 μM A83-01 and 5 μM Y-27632 (P+A+Y) media; or Keratinocyte-SFM (Gibco/Thermo Fisher 17005-042) supplied with prequalified human recombinant Epidermal Growth Factor 1-53 (EGF 1-53, used at 0.5 ng/mL) and Bovine Pituitary Extract (BPE, used at 30 μg/mL), and supplemented with 1 μM A 83-01, 5 μM Y-27632 and 3 μM isoproterenol (KSFM A+Y)+1.5 mM $CaCl_2$, to allow the cells attach to the substrate.

The microcarriers are then grown as free-floating spheres in an ultra-low attachment plate (Corning, 3471) in P+A+Y medium to allow the cells grow to confluence and form apical side outward-oriented (ASO) epithelial spheroids. The microcarriers can then be quickly dissolved to release the spheroids following the instruction provided by the supplier.

The ASO epithelial spheroids are maintained in suspension culture for at least 3 months. The epithelial spheroids also are cryopreserved in liquid nitrogen storage with P+A+Y+10% FBS+10% DMSO, and thawed like regular cell cultures. After thawing from liquid nitrogen storage, the ASO epithelial spheroids are cultured in suspension in P+A+Y for at least two weeks.

Example 5: Examples of Embodiments

The examples set forth below illustrate certain embodiments and do not limit the technology.

A1. A method for producing a cellular spheroid comprising:

(a) aggregating a plurality of epithelial cells under aggregation conditions, thereby forming a cellular aggregate, wherein the epithelial cells comprise an apical membrane and a basal membrane; and (b) culturing the cellular aggregate under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior.

A1.1 A method for producing a cellular spheroid comprising:

(a) aggregating a plurality of epithelial cells under aggregation conditions, thereby forming a cellular aggregate, wherein the epithelial cells comprise an apical membrane and a basal membrane; and (b) culturing the cellular aggregate under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior; wherein the aggregation conditions and/or the spheroid-inducing culture conditions comprise one or more transforming growth factor beta (TGF-beta) inhibitors and one or more cytoskeletal structure modulators.

A2. The method of embodiment A1 or A1.1, wherein the aggregation conditions comprise culturing the epithelial cells in an aggregation well or container.

A3. The method of embodiment A1 or A1.1, wherein the aggregation conditions comprise culturing the epithelial cells in a hanging drop.

A4. The method of any one of embodiments A1 to A3, wherein the cellular aggregate comprises one or more basement membrane components.

A4.1 The method of any one of embodiments A1 to A4, wherein the epithelial cells in the cellular aggregate produce one or more basement membrane components.

A5. The method of embodiment A4 or A4.1, wherein the one or more basement membrane components comprise basement membrane proteins or fragments thereof.

A6. The method of embodiment A5, wherein the one or more basement membrane proteins comprise laminin.

A7. The method of embodiment A6, wherein the one or more basement membrane proteins comprise collagen.

A8. The method of embodiment A7, wherein the one or more basement membrane components comprise collagen IV.

A9. The method of embodiment A8, wherein the one or more basement membrane components comprise fibronectin.

A10. The method of embodiment A9, wherein the one or more basement membrane components comprise nidogen.

A11. The method of any one of embodiments A1 to A10, wherein the aggregation conditions are serum-free conditions.

A12. The method of any one of embodiments A1 to A11, wherein the aggregation conditions are feeder cell-free conditions.

A13. The method of any one of embodiments A1 to A12, wherein the aggregation conditions are defined conditions.

A14. The method of any one of embodiments A1 to A13, wherein the aggregation conditions are xeno-free conditions.

A15. The method of any one of embodiments A1 to A14, wherein the aggregation conditions comprise one or more transforming growth factor beta (TGF-beta) inhibitors.

A16. The method of any one of embodiments A1 to A15, wherein the aggregation conditions comprise one or more cytoskeletal structure modulators.

A17. The method of any one of embodiments A1 to A16, wherein the aggregation conditions comprise one or more transforming growth factor beta (TGF-beta) inhibitors and one or more cytoskeletal structure modulators.

A18. The method of any one of embodiments A15 to A17, wherein the one or more TGF-beta inhibitors comprise one or more ALK5 inhibitors.

A19. The method of embodiment A18, wherein the one or more ALK5 inhibitors are chosen from A83-01, GW788388, RepSox, and SB 431542.

A20. The method of any one of embodiments A16 to A19, wherein the one or more cytoskeletal structure modulators comprise one or more agents that disrupt cytoskeletal structure.

A21. The method any one of embodiments A16 to A20, wherein the one or more cytoskeletal structure modulators are chosen from one or more of a Rho-associated protein kinase inhibitor, a p21-activated kinase (PAK) inhibitor, and a myosin II inhibitor.

A22. The method of embodiment A21, wherein the one or more cytoskeletal structure modulators are chosen from one or more Rho-associated protein kinase inhibitors.

A23. The method of embodiment A22, wherein the one or more Rho-associated protein kinase inhibitors are chosen from Y-27632, SR 3677, thiazovivin, HA1100 hydrochloride, HA1077 and GSK-429286.

A24. The method of embodiment A21, wherein the one or more cytoskeletal structure modulators are chosen from one or more PAK inhibitors.

A25. The method of embodiment A24, wherein one or more PAK inhibitors comprise IPA3.

A26. The method of embodiment A21, wherein the one or more cytoskeletal structure modulators are chosen from one or more myosin II inhibitors.

A27. The method of embodiment A26, wherein the one or more myosin II inhibitors comprise blebbistatin.

A28. The method of any one of embodiments A1 to A27, wherein the aggregation conditions comprise calcium at a concentration of at least 0.5 mM.

A28.1 The method of any one of embodiments A1 to A27, wherein the aggregation conditions comprise calcium at a concentration of at least 1 mM.

A29. The method of any one of embodiments A1 to A27, wherein the aggregation conditions comprise calcium at a concentration of at least 1.5 mM.

A30. The method of any one of embodiments A1 to A29, wherein the spheroid-inducing culture conditions comprise culturing the cellular aggregate in liquid suspension.

A31. The method of any one of embodiments A1 to A29, wherein the spheroid-inducing culture conditions comprise encapsulating the cellular aggregate in a hydrogel.

A32. The method of any one of embodiments A1 to A29, wherein the spheroid-inducing culture conditions comprise encapsulating the cellular aggregate in an extracellular matrix.

A33. The method of any one of embodiments A1 to A32, wherein the spheroid-inducing culture conditions are serum-free conditions.

A34. The method of any one of embodiments A1 to A33, wherein the spheroid-inducing culture conditions are feeder cell-free conditions.

A35. The method of any one of embodiments A1 to A34, wherein the spheroid-inducing culture conditions are defined conditions.

A36. The method of any one of embodiments A1 to A35, wherein the spheroid-inducing culture conditions are xeno-free conditions.

A37. The method of any one of embodiments A1 to A36, wherein the spheroid-inducing culture conditions comprise one or more transforming growth factor beta (TGF-beta) inhibitors.

A38. The method of any one of embodiments A1 to A37, wherein the spheroid-inducing culture conditions comprise one or more cytoskeletal structure modulators.

A39. The method of any one of embodiments A1 to A38, wherein the spheroid-inducing culture conditions comprise one or more transforming growth factor beta (TGF-beta) inhibitors and one or more cytoskeletal structure modulators.

A40. The method of any one of embodiments A37 to A39, wherein the one or more TGF-beta inhibitors comprise one or more ALK5 inhibitors.

A41. The method of embodiment A40, wherein the one or more ALK5 inhibitors are chosen from A83-01, GW788388, RepSox, and SB 431542.

A42. The method of any one of embodiments A38 to A41, wherein the one or more cytoskeletal structure modulators comprise one or more agents that disrupt cytoskeletal structure.

A43. The method of any one of embodiments A38 to A42, wherein the one or more cytoskeletal structure modulators are chosen from one or more of a Rho-associated protein kinase inhibitor, a p21-activated kinase (PAK) inhibitor, and a myosin II inhibitor.

A44. The method of embodiment A43, wherein the one or more cytoskeletal structure modulators are chosen from one or more Rho-associated protein kinase inhibitors.

A45. The method of embodiment A44, wherein the one or more Rho-associated protein kinase inhibitors are chosen from Y-27632, SR 3677, thiazovivin, HA1100 hydrochloride, HA1077 and GSK-429286.

A46. The method of embodiment A43, wherein the one or more cytoskeletal structure modulators are chosen from one or more PAK inhibitors.

A47. The method of embodiment A46, wherein one or more PAK inhibitors comprise IPA3.

A48. The method of embodiment A43, wherein the one or more cytoskeletal structure modulators are chosen from one or more myosin II inhibitors.

A49. The method of embodiment A48, wherein the one or more myosin II inhibitors comprise blebbistatin.

A50. The method of any one of embodiments A1 to A49, wherein the spheroid-inducing culture conditions comprise calcium at a concentration of at least 0.5 mM.

A50.1 The method of any one of embodiments A1 to A49, wherein the spheroid-inducing culture conditions comprise calcium at a concentration of at least 1 mM.

A51. The method of any one of embodiments A1 to A49, wherein the spheroid-inducing culture conditions comprise calcium at a concentration of at least 1.5 mM.

A52. The method of any one of embodiments A1 to A51, wherein the spheroid is solid.

A53. The method of any one of embodiments A1 to A51, wherein the spheroid is hollow.

A54. The method of embodiment A53, wherein the spheroid interior comprises a lumen.

A55. The method of any one of embodiments A1 to A54, wherein each of the epithelial cells in the spheroid comprises a lateral membrane.

A56. The method of embodiment A55, wherein the epithelial cells in the spheroid comprise intercellular tight junctions at the lateral membrane.

A57. The method of any one of embodiments A1 to A56, wherein the spheroid exterior comprises cilia and/or microvilli.

A58. The method of any one of embodiments A1 to A57, wherein the spheroid interior comprises one or more basement membrane components.

A59. The method of any one of embodiments A1 to A58, wherein the cellular spheroid is produced ex vivo.

A60. The method of any one of embodiments A1 to A59, wherein the cellular spheroid is an isolated cellular spheroid.

A61. The method of any one of embodiments A1 to A60, wherein the cellular spheroid is an artificial cellular assembly.

A62. The method of any one of embodiments A1 to A61, wherein the epithelial cells in (a) comprise non-primary cultured epithelial cells.

A63. The method of any one of embodiments A1 to A62, wherein the epithelial cells in (a) comprise ex-vivo expanded epithelial cells.

A64. The method of any one of embodiments A1 to A63, wherein the epithelial cells in (a) comprise isolated epithelial cells.

A65. The method of any one of embodiments A1 to A64, wherein the epithelial cells in (a) comprise genetically engineered epithelial cells.

A66. The method of any one of embodiments A1 to A65, wherein the epithelial cells in (a) comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

A67. The method of embodiment A66, wherein the epithelial cells in (a) comprise airway epithelial cells.

A68. The method of embodiment A66, wherein the epithelial cells in (a) comprise keratinocyte epithelial cells.

A69. The method of embodiment A66, wherein the epithelial cells in (a) comprise prostate epithelial cells.

A70. The method of embodiment A66, wherein the epithelial cells in (a) comprise mammary epithelial cells.

A71. The method of any one of embodiments A1 to A70, wherein the epithelial cells in (a) comprise primary epithelial cells.

A72. The method of any one of embodiments A1 to A71, wherein the epithelial cells in (a) comprise expanded primary epithelial cells.

A73. The method of any one of embodiments A1 to A72, wherein the epithelial cells in (a) comprise isolated primary epithelial cells.

A74. The method of any one of embodiments A1 to A73, wherein the epithelial cells in (a) comprise anchorage dependent epithelial cells.

A75. The method of any one of embodiments A1 to A74, comprising prior to (a) obtaining the epithelial cells from a subject.

A76. The method of embodiment A75, wherein the subject is a human.

A77. The method of any one of embodiments A1 to A76, comprising prior to (a) isolating the epithelial cells from tissue from a subject, thereby generating isolated epithelial cells.

A78. The method of embodiment A77, wherein the isolated epithelial cells comprise no extracellular components from the tissue from the subject.

B1. A method for producing a cellular spheroid comprising:

(a) attaching one or more epithelial cells to a substrate under substrate attachment conditions, thereby forming a cell-substrate body, wherein the one or more epithelial cells comprise an apical membrane and a basal membrane; and (b) culturing the cell-substrate body under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior.

B1.1 A method for producing a cellular spheroid comprising:

(a) attaching one or more epithelial cells to a substrate under substrate attachment conditions, thereby forming a cell-substrate body, wherein the one or more epithelial cells comprise an apical membrane and a basal membrane; and (b) culturing the cell-substrate body under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior; wherein the substrate attachment conditions and/or the spheroid-inducing culture conditions comprise one or more transforming growth factor beta (TGF-beta) inhibitors and one or more cytoskeletal structure modulators.

B2. The method of embodiment B1 or B1.1, comprising after (b), dissolving the substrate.

B3. The method of embodiment B1, B1.1, or B2, wherein the substrate is a microsphere.

B4. The method of embodiment B1, B1.1 or B2, wherein the substrate is a microcarrier.

B5. The method of any one of embodiments B1 to B4, wherein the substrate comprises a coating.

B5.1 The method of embodiment B5, wherein the coating comprises one or more basement membrane components.

B6. The method of embodiment B5.1, wherein the one or more basement membrane components comprise one or more basement membrane proteins or fragments thereof.

B7. The method of embodiment B6, wherein the one or more basement membrane proteins comprise one or more of laminin, collagen, fibronectin, and nidogen.

B8. The method of embodiment B6, wherein the one or more basement membrane proteins comprise collagen IV.

B9. The method of embodiment B5, wherein the one or more basement membrane components comprise mimetic peptides.

B10. The method of embodiment B9, wherein the one or more basement membrane components comprise fibronectin-mimetic peptides and/or laminin-mimetic peptides.

B11. The method of any one of embodiments B1 to B10, wherein the substrate attachment conditions are serum-free conditions.

B12. The method of any one of embodiments B1 to B11, wherein the substrate attachment conditions are feeder cell-free conditions.

B13. The method of any one of embodiments B1 to B12, wherein the substrate attachment conditions are defined conditions.

B14. The method of any one of embodiments B1 to B13, wherein the substrate attachment conditions are xeno-free conditions.

B15. The method of any one of embodiments B1 to B14, wherein the substrate attachment conditions comprise one or more transforming growth factor beta (TGF-beta) inhibitors.

B16. The method of any one of embodiments B1 to B15, wherein the substrate attachment conditions comprise one or more cytoskeletal structure modulators.

B17. The method of any one of embodiments B1 to B16, wherein the substrate attachment conditions comprise one or more transforming growth factor beta (TGF-beta) inhibitors and one or more cytoskeletal structure modulators.

B18. The method of any one of embodiments B15 to B17, wherein the one or more TGF-beta inhibitors comprise one or more ALK5 inhibitors.

B19. The method of embodiment B18, wherein the one or more ALK5 inhibitors are chosen from A83-01, GW788388, RepSox, and SB 431542.

B20. The method of any one of embodiments B16 to B19, wherein the one or more cytoskeletal structure modulators comprise one or more agents that disrupt cytoskeletal structure.

B21. The method of any one of embodiments B16 to B20, wherein the one or more cytoskeletal structure modulators are chosen from one or more of a Rho-associated protein kinase inhibitor, a p21-activated kinase (PAK) inhibitor, and a myosin II inhibitor.

B22. The method of embodiment B21, wherein the one or more cytoskeletal structure modulators are chosen from one or more Rho-associated protein kinase inhibitors.

B23. The method of embodiment B22, wherein the one or more Rho-associated protein kinase inhibitors are chosen from Y-27632, SR 3677, thiazovivin, HA1100 hydrochloride, HA1077 and GSK-429286.

B24. The method of embodiment B21, wherein the one or more cytoskeletal structure modulators are chosen from one or more PAK inhibitors.

B25. The method of embodiment B24, wherein one or more PAK inhibitors comprise IPA3.

B26. The method of embodiment B21, wherein the one or more cytoskeletal structure modulators are chosen from one or more myosin II inhibitors.

B27. The method of embodiment B26, wherein the one or more myosin II inhibitors comprise blebbistatin.

B28. The method of any one of embodiments B1 to B27, wherein the substrate attachment conditions comprise calcium at a concentration of at least 0.5 mM.

B28.1 The method of any one of embodiments B1 to B27, wherein the substrate attachment conditions comprise calcium at a concentration of at least 1 mM.

B29. The method of any one of embodiments B1 to B27, wherein the substrate attachment conditions comprise calcium at a concentration of at least 1.5 mM.

B30. The method of any one of embodiments B1 to B29, wherein the spheroid-inducing culture conditions comprise culturing the cell-substrate body in liquid suspension.

B31. The method of any one of embodiments B1 to B29, wherein the spheroid-inducing culture conditions comprise encapsulating the cell-substrate body in a hydrogel.

B32. The method of any one of embodiments B1 to B29, wherein the spheroid-inducing culture conditions comprise encapsulating the cell-substrate body in an extracellular matrix.

B33. The method of any one of embodiments B1 to B32, wherein the spheroid-inducing culture conditions are serum-free conditions.

B34. The method of any one of embodiments B1 to B33, wherein the spheroid-inducing culture conditions are feeder cell-free conditions.

B35. The method of any one of embodiments B1 to B34, wherein the spheroid-inducing culture conditions are defined conditions.

B36. The method of any one of embodiments B1 to B35, wherein the spheroid-inducing culture conditions are xeno-free conditions.

B37. The method of any one of embodiments B1 to B36, wherein the spheroid-inducing culture conditions comprise one or more transforming growth factor beta (TGF-beta) inhibitors.

B38. The method of any one of embodiments B1 to B37, wherein the spheroid-inducing culture conditions comprise one or more cytoskeletal structure modulators.

B39. The method of any one of embodiments B1 to B38, wherein the spheroid-inducing culture conditions comprise one or more transforming growth factor beta (TGF-beta) inhibitors and one or more cytoskeletal structure modulators.

B40. The method of any one of embodiments B37 to B39, wherein the one or more TGF-beta inhibitors comprise one or more ALK5 inhibitors.

B41. The method of embodiment B40, wherein the one or more ALK5 inhibitors are chosen from A83-01, GW788388, RepSox, and SB 431542.

B42. The method of any one of embodiments B39 to B41, wherein the one or more cytoskeletal structure modulators comprise one or more agents that disrupt cytoskeletal structure.

B43. The method of any one of embodiments B39 to B42, wherein the one or more cytoskeletal structure modulators are chosen from one or more of a Rho-associated protein kinase inhibitor, a p21-activated kinase (PAK) inhibitor, and a myosin II inhibitor.

B44. The method of embodiment B43, wherein the one or more cytoskeletal structure modulators are chosen from one or more Rho-associated protein kinase inhibitors.

B45. The method of embodiment B44, wherein the one or more Rho-associated protein kinase inhibitors are chosen from Y-27632, SR 3677, thiazovivin, HA1100 hydrochloride, HA1077 and GSK-429286.

B46. The method of embodiment B43, wherein the one or more cytoskeletal structure modulators are chosen from one or more PAK inhibitors.

B47. The method of embodiment B46, wherein one or more PAK inhibitors comprise IPA3.

B48. The method of embodiment B43, wherein the one or more cytoskeletal structure modulators are chosen from one or more myosin II inhibitors.

B49. The method of embodiment B48, wherein the one or more myosin II inhibitors comprise blebbistatin.

B50. The method of any one of embodiments B1 to B49, wherein the spheroid-inducing culture conditions comprise calcium at a concentration of at least 0.5 mM.

B50.1 The method of any one of embodiments B1 to B49, wherein the spheroid-inducing culture conditions comprise calcium at a concentration of at least 1 mM.

B51. The method of any one of embodiments B1 to B49, wherein the spheroid-inducing culture conditions comprise calcium at a concentration of at least 1.5 mM.

B52. The method of any one of embodiments B1 to B51, wherein the spheroid is solid.

B53. The method of any one of embodiments B1 to B51, wherein the spheroid is hollow.

B54. The method of embodiment B53, wherein the spheroid interior comprises a lumen.

B55. The method of any one of embodiments B1 to B54, wherein each of the epithelial cells in the spheroid comprises a lateral membrane.

B56. The method of embodiment B55, wherein the epithelial cells in the spheroid comprise intercellular tight junctions at the lateral membrane.

B57. The method of any one of embodiments B1 to B56, wherein the spheroid exterior comprises cilia and/or microvilli.

B58. The method of any one of embodiments B1 to B57, wherein the spheroid interior comprises one or more basement membrane components.

B59. The method of any one of embodiments B1 to B58, wherein the cellular spheroid is produced ex vivo.

B60. The method of any one of embodiments B1 to B59, wherein the cellular spheroid is an isolated cellular spheroid.

B61. The method of any one of embodiments B1 to B60, wherein the cellular spheroid is an artificial cellular assembly.

B62. The method of any one of embodiments B1 to B61, wherein the epithelial cells in (a) comprise non-primary cultured epithelial cells.

B63. The method of any one of embodiments B1 to B62, wherein the epithelial cells in (a) comprise ex-vivo expanded epithelial cells.

B64. The method of any one of embodiments B1 to B63, wherein the epithelial cells in (a) comprise isolated epithelial cells.

B65. The method of any one of embodiments B1 to B64, wherein the epithelial cells in (a) comprise genetically engineered epithelial cells.

B66. The method of any one of embodiments B1 to B65, wherein the epithelial cells comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

B67. The method of embodiment B66, wherein the epithelial cells comprise airway epithelial cells.

B68. The method of embodiment B66, wherein the epithelial cells comprise keratinocyte epithelial cells.

B69. The method of embodiment B66, wherein the epithelial cells comprise prostate epithelial cells.

B70. The method of embodiment B66, wherein the epithelial cells comprise mammary epithelial cells.

B71. The method of any one of embodiments B1 to B70, wherein the epithelial cells in (a) comprise primary epithelial cells.

B72. The method of any one of embodiments B1 to B71, wherein the epithelial cells in (a) comprise expanded primary epithelial cells.

B73. The method of any one of embodiments B1 to B72, wherein the epithelial cells in (a) comprise isolated primary epithelial cells.

B74. The method of any one of embodiments B1 to B73, wherein the epithelial cells in (a) comprise anchorage dependent epithelial cells.

B75. The method of any one of embodiments B1 to B74, comprising prior to (a) obtaining the epithelial cells from a subject.

B76. The method of embodiment B75, wherein the subject is a human.

B77. The method of any one of embodiments B1 to B76, comprising prior to (a) isolating the epithelial cells from tissue from a subject, thereby generating isolated epithelial cells.

B78. The method of embodiment B77, wherein the isolated epithelial cells comprise no extracellular components from the tissue from the subject.

C1. An artificial cellular assembly comprising epithelial cells assembled into a spheroid, wherein:

the spheroid comprises an interior and an exterior;

each of the epithelial cells comprises an apical membrane and a basal membrane; and for some or all of the epithelial cells in the spheroid, the basal membrane is in the spheroid interior and the apical membrane is on the spheroid exterior.

C1.1 The artificial cellular assembly of embodiment C1, wherein the epithelial cells were obtained from a subject.

C1.2 The artificial cellular assembly of embodiment C2, wherein the subject is a human subject.

C2. The artificial cellular assembly of embodiment C1, C1.1, or C1.2, wherein the spheroid is solid.

C3. The artificial cellular assembly of embodiment C1, C1.1, or C1.2, wherein the spheroid is hollow.

C4. The artificial cellular assembly of embodiment C3, wherein the spheroid interior comprises a lumen.

C5. The artificial cellular assembly of any one of embodiments C1 to C4, wherein each of the epithelial cells comprises a lateral membrane.

C6. The artificial cellular assembly of embodiment C5, wherein the epithelial cells comprise intercellular junctions at the lateral membrane.

C7. The artificial cellular assembly of any one of embodiments C1 to C6, wherein the spheroid exterior comprises cilia and/or microvilli.

C8. The artificial cellular assembly of any one of embodiments C1 to C7, wherein the spheroid interior comprises one or more basement membrane components.

C9. The artificial cellular assembly of embodiment C8, wherein the one or more basement membrane components comprise one or more basement membrane proteins or fragments thereof.

C10. The artificial cellular assembly of embodiment C9, wherein the one or more basement membrane proteins comprise one or more of laminin, collagen, fibronectin, and nidogen.

C11. The artificial cellular assembly of embodiment C9, wherein the one or more basement membrane proteins comprise collagen IV.

C12. The artificial cellular assembly of embodiment C8, wherein the one or more basement membrane components comprise mimetic peptides.

C13. The artificial cellular assembly of embodiment C12, wherein the one or more basement membrane components comprise fibronectin-mimetic peptides and/or laminin-mimetic peptides.

C14. The artificial cellular assembly of any one of embodiments C8 to C13, wherein the one or more basement membrane components are produced by the epithelial cells.

C14.1 The artificial cellular assembly of any one of embodiments C8 to C14, wherein the one or more basement membrane components were not obtained from the subject.

C15. The artificial cellular assembly of any one of embodiments C8 to C13, wherein the epithelial cells are attached to a substrate.

C16. The artificial cellular assembly of embodiment C15, wherein the substrate is a microsphere.

C17. The artificial cellular assembly of embodiment C15, wherein the substrate is a microcarrier.

C18. The artificial cellular assembly of any one of embodiments C15 to C17, wherein the one or more basement membrane components are provided on the substrate.

C19. The artificial cellular assembly of any one of embodiments C1 to C18, wherein the spheroid is produced ex vivo.

C20. The artificial cellular assembly of any one of embodiments C1 to C19, wherein the spheroid is an isolated spheroid.

C21. The artificial cellular assembly of any one of embodiments C1 to C20, wherein the epithelial cells comprise primary epithelial cells.

C21.1 The artificial cellular assembly of any one of embodiments C1 to C21, wherein the epithelial cells comprise anchorage dependent epithelial cells.

C22. The artificial cellular assembly of any one of embodiments C1 to C20, wherein the epithelial cells are derived from non-primary cultured epithelial cells.

C22.1 The artificial cellular assembly of embodiment C22, wherein the epithelial cells are derived from anchorage dependent non-primary cultured epithelial cells.

C23. The artificial cellular assembly of any one of embodiments C1 to C22.1, wherein the epithelial cells are derived from ex-vivo expanded epithelial cells.

C24. The artificial cellular assembly of any one of embodiments C1 to C23, wherein the epithelial cells comprise isolated epithelial cells.

C25. The artificial cellular assembly of any one of embodiments C1 to C23, wherein the epithelial cells are derived from isolated epithelial cells.

C26. The artificial cellular assembly of any one of embodiments C1 to C25, wherein the epithelial cells are derived from genetically engineered epithelial cells.

C27. The artificial cellular assembly of any one of embodiments C1 to C26, wherein the epithelial cells comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

C28. The artificial cellular assembly of embodiment C27, wherein the epithelial cells comprise airway epithelial cells.

C29. The artificial cellular assembly of embodiment C27, wherein the epithelial cells comprise keratinocyte epithelial cells.

C30. The artificial cellular assembly of embodiment C27, wherein the epithelial cells comprise prostate epithelial cells.

C31. The artificial cellular assembly of embodiment C27, wherein the epithelial cells comprise mammary epithelial cells.

D1. A cellular spheroid produced by or obtainable by a method comprising:
- (a) aggregating a plurality of epithelial cells under aggregation conditions, thereby forming a cellular aggregate, wherein the epithelial cells comprise an apical membrane and a basal membrane; and
- (b) culturing the cellular aggregate under spheroid-inducing culture conditions, thereby generating a cellular spheroid wherein:
  - (i) the spheroid comprises an interior and an exterior, and
  - (ii) for some or all of the epithelial cells in the spheroid, the basal membrane is in the spheroid interior and the apical membrane is on the spheroid exterior.

D1.1 A cellular spheroid produced by or obtainable by a method comprising:
- (a) aggregating a plurality of epithelial cells under aggregation conditions, thereby forming a cellular aggregate, wherein the epithelial cells comprise an apical membrane and a basal membrane; and
- (b) culturing the cellular aggregate under spheroid-inducing culture conditions, thereby generating a cellular spheroid wherein:
  - (i) the spheroid comprises an interior and an exterior, and
  - (ii) for some or all of the epithelial cells in the spheroid, the basal membrane is in the spheroid interior and the apical membrane is on the spheroid exterior; wherein the aggregation conditions and/or the spheroid-inducing culture conditions comprise one or more transforming growth factor beta (TGF-beta) inhibitors and one or more cytoskeletal structure modulators.

D2. The cellular spheroid of embodiment D1 or D1.1, wherein the aggregation conditions comprise culturing the epithelial cells in an aggregation well or container.

D3. The cellular spheroid of embodiment D1 or D1.1, wherein the aggregation conditions comprise culturing the epithelial cells in a hanging drop.

D4. The cellular spheroid of any one of embodiments D1 to D3, wherein the cellular aggregate comprises one or more basement membrane components.

D4.1 The cellular spheroid of any one of embodiments D1 to D4, wherein the epithelial cells in the cellular aggregate produce one or more basement membrane components.

D5. The cellular spheroid of embodiment D4 or D4.1, wherein the one or more basement membrane components comprise one or more basement membrane proteins or fragments thereof.

D6. The cellular spheroid of embodiment D5, wherein the one or more basement membrane proteins comprise collagen.

D7. The cellular spheroid of embodiment D6, wherein the one or more basement membrane proteins comprise collagen IV.

D8. The cellular spheroid of embodiment D7, wherein the one or more basement membrane components comprise laminin.

D9. The cellular spheroid of embodiment D8, wherein the one or more basement membrane components comprise fibronectin.

D10. The cellular spheroid of embodiment D9, wherein the one or more basement membrane components comprise nidogen.

D11. The cellular spheroid of any one of embodiments D1 to D10, wherein the aggregation conditions are serum-free conditions.

D12. The cellular spheroid of any one of embodiments D1 to D11, wherein the aggregation conditions are feeder cell-free conditions.

D13. The cellular spheroid of any one of embodiments D1 to D12, wherein the aggregation conditions are defined conditions.

D14. The cellular spheroid of any one of embodiments D1 to D13, wherein the aggregation conditions are xeno-free conditions.

D15. The cellular spheroid of any one of embodiments D1 to D14, wherein the aggregation conditions comprise one or more transforming growth factor beta (TGF-beta) inhibitors.

D16. The cellular spheroid of any one of embodiments D1 to D15, wherein the aggregation conditions comprise one or more cytoskeletal structure modulators.

D17. The cellular spheroid of any one of embodiments D1 to D16, wherein the aggregation conditions comprise one or more transforming growth factor beta (TGF-beta) inhibitors and one or more cytoskeletal structure modulators.

D18. The cellular spheroid of any one of embodiments D15 to D17, wherein the one or more TGF-beta inhibitors comprise one or more ALK5 inhibitors.

D19. The cellular spheroid of embodiment D18, wherein the one or more ALK5 inhibitors are chosen from A83-01, GW788388, RepSox, and SB 431542.

D20. The cellular spheroid of method of any one of embodiments D16 to D19, wherein the one or more cytoskeletal structure modulators comprise one or more agents that disrupt cytoskeletal structure.

D21. The cellular spheroid of method of any one of embodiments D16 to D20, wherein the one or more cytoskeletal structure modulators are chosen from one or more of a Rho-associated protein kinase inhibitor, a p21-activated kinase (PAK) inhibitor, and a myosin II inhibitor.

D22. The cellular spheroid of embodiment D21, wherein the one or more cytoskeletal structure modulators are chosen from one or more Rho-associated protein kinase inhibitors.

D23. The cellular spheroid of embodiment D22, wherein the one or more Rho-associated protein kinase inhibitors are chosen from Y-27632, SR 3677, thiazovivin, HA1100 hydrochloride, HA1077 and GSK-429286.

D24. The cellular spheroid of embodiment D21, wherein the one or more cytoskeletal structure modulators are chosen from one or more PAK inhibitors.

D25. The cellular spheroid of embodiment D24, wherein one or more PAK inhibitors comprise IPA3.

D26. The cellular spheroid of embodiment D21, wherein the one or more cytoskeletal structure modulators are chosen from one or more myosin II inhibitors.

D27. The cellular spheroid of embodiment D26, wherein the one or more myosin II inhibitors comprise blebbistatin.

D28. The cellular spheroid of any one of embodiments D1 to D27, wherein the aggregation conditions comprise calcium at a concentration of at least 0.5 mM.

D28.1 The cellular spheroid of any one of embodiments D1 to D27, wherein the aggregation conditions comprise calcium at a concentration of at least 1 mM.

D29. The cellular spheroid of any one of embodiments D1 to D27, wherein the aggregation conditions comprise calcium at a concentration of at least 1.5 mM.

D30. The cellular spheroid of any one of embodiments D1 to D29, wherein the spheroid-inducing culture conditions comprise culturing the cellular aggregate in liquid suspension.

D31. The cellular spheroid of any one of embodiments D1 to D29, wherein the spheroid-inducing culture conditions comprise encapsulating the cellular aggregate in a hydrogel.

D32. The cellular spheroid of any one of embodiments D1 to D29, wherein the spheroid-inducing culture conditions comprise encapsulating the cellular aggregate in an extracellular matrix.

D33. The cellular spheroid of any one of embodiments D1 to D32, wherein the spheroid-inducing culture conditions are serum-free conditions.

D34. The cellular spheroid of any one of embodiments D1 to D33, wherein the spheroid-inducing culture conditions are feeder cell-free conditions.

D35. The cellular spheroid of any one of embodiments D1 to D34, wherein the spheroid-inducing culture conditions are defined conditions.

D36. The cellular spheroid of any one of embodiments D1 to D35, wherein the spheroid-inducing culture conditions are xeno-free conditions.

D37. The cellular spheroid of any one of embodiments D1 to D36, wherein the spheroid-inducing culture conditions comprise one or more transforming growth factor beta (TGF-beta) inhibitors.

D38. The cellular spheroid of any one of embodiments D1 to D37, wherein the spheroid-inducing culture conditions comprise one or more cytoskeletal structure modulators.

D39. The cellular spheroid of any one of embodiments D1 to D38, wherein the spheroid-inducing culture conditions comprise one or more transforming growth factor beta (TGF-beta) inhibitors and one or more cytoskeletal structure modulators.

D40. The cellular spheroid of any one of embodiments D37 to D39, wherein the one or more TGF-beta inhibitors comprise one or more ALK5 inhibitors.

D41. The cellular spheroid of embodiment D40, wherein the one or more ALK5 inhibitors are chosen from A83-01, GW788388, RepSox, and SB 431542.

D42. The cellular spheroid of method of any one of embodiments D38 to D41, wherein the one or more cytoskeletal structure modulators comprise one or more agents that disrupt cytoskeletal structure.

D43. The cellular spheroid of any one of embodiments D38 to D42, wherein the one or more cytoskeletal structure modulators are chosen from one or more of a Rho-associated protein kinase inhibitor, a p21-activated kinase (PAK) inhibitor, and a myosin II inhibitor.

D44. The cellular spheroid of embodiment D43, wherein the one or more cytoskeletal structure modulators are chosen from one or more Rho-associated protein kinase inhibitors.

D45. The cellular spheroid of embodiment D44, wherein the one or more Rho-associated protein kinase inhibitors are chosen from Y-27632, SR 3677, thiazovivin, HA1100 hydrochloride, HA1077 and GSK-429286.

D46. The cellular spheroid of embodiment D43, wherein the one or more cytoskeletal structure modulators are chosen from one or more PAK inhibitors.

D47. The cellular spheroid of embodiment D46, wherein one or more PAK inhibitors comprise IPA3.

D48. The cellular spheroid of embodiment D43, wherein the one or more cytoskeletal structure modulators are chosen from one or more myosin II inhibitors.

D49. The cellular spheroid of embodiment D48, wherein the one or more myosin II inhibitors comprise blebbistatin.

D50. The cellular spheroid of any one of embodiments D1 to D49, wherein the spheroid-inducing culture conditions comprise calcium at a concentration of at least 0.5 mM.

D50.1 The cellular spheroid of any one of embodiments D1 to D49, wherein the spheroid-inducing culture conditions comprise calcium at a concentration of at least 1 mM.

D51. The cellular spheroid of any one of embodiments D1 to D49, wherein the spheroid-inducing culture conditions comprise calcium at a concentration of at least 1.5 mM.

D52. The cellular spheroid of any one of embodiments D1 to D51, wherein the spheroid is solid.

D53. The cellular spheroid of any one of embodiments D1 to D51, wherein the spheroid is hollow.

D54. The cellular spheroid of embodiment D53, wherein the spheroid interior comprises a lumen.

D55. The cellular spheroid of any one of embodiments D1 to D54, wherein each of the epithelial cells in the spheroid comprises a lateral membrane.

D56. The cellular spheroid of embodiment D55, wherein the epithelial cells in the spheroid comprise intercellular tight junctions at the lateral membrane.

D57. The cellular spheroid of any one of embodiments D1 to D56, wherein the spheroid exterior comprises cilia and/or microvilli.

D58. The cellular spheroid of any one of embodiments D1 to D57, wherein the spheroid interior comprises one or more basement membrane components.

D59. The cellular spheroid of any one of embodiments D1 to D58, wherein the cellular spheroid is produced ex vivo.

D60. The cellular spheroid of any one of embodiments D1 to D59, wherein the cellular spheroid is an isolated cellular spheroid.

D61. The cellular spheroid of any one of embodiments D1 to D60, wherein the cellular spheroid is an artificial cellular assembly.

D62. The cellular spheroid of any one of embodiments D1 to D61, wherein the epithelial cells in (a) comprise non-primary cultured epithelial cells.

D63. The cellular spheroid of any one of embodiments D1 to D62, wherein the epithelial cells in (a) comprise ex-vivo expanded epithelial cells.

D64. The cellular spheroid of any one of embodiments D1 to D63, wherein the epithelial cells in (a) comprise isolated epithelial cells.

D65. The cellular spheroid of any one of embodiments D1 to D64, wherein the epithelial cells in (a) comprise genetically engineered epithelial cells.

D66. The cellular spheroid of any one of embodiments D1 to D65, wherein the epithelial cells comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

D67. The cellular spheroid of embodiment D66, wherein the epithelial cells comprise airway epithelial cells.

D68. The cellular spheroid of embodiment D66, wherein the epithelial cells comprise keratinocyte epithelial cells.

D69. The cellular spheroid of embodiment D66, wherein the epithelial cells comprise prostate epithelial cells.

D70. The cellular spheroid of embodiment D66, wherein the epithelial cells comprise mammary epithelial cells.

D71. The cellular spheroid of any one of embodiments D1 to D70, wherein the epithelial cells in (a) comprise primary epithelial cells.

D72. The cellular spheroid of any one of embodiments D1 to D71, wherein the epithelial cells in (a) comprise expanded primary epithelial cells.

D73. The cellular spheroid of any one of embodiments D1 to D72, wherein the epithelial cells in (a) comprise isolated primary epithelial cells.

D74. The cellular spheroid of any one of embodiments D1 to D73, wherein the epithelial cells in (a) comprise anchorage dependent epithelial cells.

D75. The cellular spheroid of any one of embodiments D1 to D74, wherein the method comprises, prior to (a), obtaining the epithelial cells from a subject.

D76. The cellular spheroid of embodiment D75, wherein the subject is a human.

D77. The cellular spheroid of any one of embodiments D1 to D76, wherein the method comprises, prior to (a), isolating the epithelial cells from tissue from a subject, thereby generating isolated epithelial cells.

D78. The cellular spheroid of embodiment D77, wherein the isolated epithelial cells comprise no extracellular components from the tissue from the subject.

E1. A cellular spheroid produced by or obtainable by a method comprising:

(a) attaching one or more epithelial cells to a substrate under substrate attachment conditions, thereby forming a cell-substrate body, wherein the one or more epithelial cells comprise an apical membrane and a basal membrane; and (b) culturing the cell-substrate body under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior.

E1.1 A cellular spheroid produced by or obtainable by a method comprising:

(a) attaching one or more epithelial cells to a substrate under substrate attachment conditions, thereby forming a cell-substrate body, wherein the one or more epithelial cells comprise an apical membrane and a basal membrane; and (b) culturing the cell-substrate body under spheroid-inducing culture conditions, thereby generating a cellular spheroid wherein:

(i) the spheroid comprises an interior and an exterior, and (ii) for some or all of the epithelial cells in the spheroid, the basal membrane is in the spheroid interior and the apical membrane is on the spheroid exterior; wherein the substrate attachment conditions and/or the spheroid-inducing culture conditions comprise one or more transforming growth factor beta (TGF-beta) inhibitors and one or more cytoskeletal structure modulators.

E2. The cellular spheroid of embodiment E1 or E1.1, comprising after (b), dissolving the substrate.

E3. The cellular spheroid of embodiment E1, E1.1, or E2, wherein the substrate is a microsphere.

E4. The cellular spheroid of embodiment E1, E1.1, or E2, wherein the substrate is a microcarrier.

E5. The cellular spheroid of any one of embodiments E1 to E4, wherein the substrate comprises a coating.

E5.1 The cellular spheroid of embodiment E5, wherein the coating comprises one or more basement membrane components.

E6. The cellular spheroid of embodiment E5.1, wherein the one or more basement membrane components comprise one or more basement membrane proteins or fragments thereof.

E7. The cellular spheroid of embodiment E6, wherein the one or more basement membrane proteins comprise one or more of laminin, collagen, fibronectin, and nidogen.

E8. The cellular spheroid of embodiment E6, wherein the one or more basement membrane proteins comprise collagen IV.

E9. The cellular spheroid of embodiment E5, wherein the one or more basement membrane components comprise mimetic peptides.

E10. The cellular spheroid of embodiment E9, wherein the one or more basement membrane components comprise fibronectin-mimetic peptides and/or laminin-mimetic peptides.

E11. The cellular spheroid of any one of embodiments E1 to E10, wherein the substrate attachment conditions are serum-free conditions.

E12. The cellular spheroid of any one of embodiments E1 to E11, wherein the substrate attachment conditions are feeder cell-free conditions.

E13. The cellular spheroid of any one of embodiments E1 to E12, wherein the substrate attachment conditions are defined conditions.

E14. The cellular spheroid of any one of embodiments E1 to E13, wherein the substrate attachment conditions are xeno-free conditions.

E15. The cellular spheroid of any one of embodiments E1 to E14, wherein the substrate attachment conditions comprise one or more transforming growth factor beta (TGF-beta) inhibitors.

E16. The cellular spheroid of any one of embodiments E1 to E15, wherein the substrate attachment conditions comprise one or more cytoskeletal structure modulators.

E17. The cellular spheroid of any one of embodiments E1 to E16, wherein the substrate attachment conditions comprise one or more transforming growth factor beta (TGF-beta) inhibitors and one or more cytoskeletal structure modulators.

E18. The cellular spheroid of any one of embodiments E15 to E17, wherein the one or more TGF-beta inhibitors comprise one or more ALK5 inhibitors.

E19. The cellular spheroid of embodiment E18, wherein the one or more ALK5 inhibitors are chosen from A83-01, GW788388, RepSox, and SB 431542.

E20. The cellular spheroid of any one of embodiments E16 to E19, wherein the one or more cytoskeletal structure modulators comprise one or more agents that disrupt cytoskeletal structure.

E21. The cellular spheroid of any one of embodiments E16 to E20, wherein the one or more cytoskeletal structure modulators are chosen from one or more of a Rho-associated protein kinase inhibitor, a p21-activated kinase (PAK) inhibitor, and a myosin II inhibitor.

E22. The cellular spheroid of embodiment E21, wherein the one or more cytoskeletal structure modulators are chosen from one or more Rho-associated protein kinase inhibitors.

E23. The cellular spheroid of embodiment E22, wherein the one or more Rho-associated protein kinase inhibitors are chosen from Y-27632, SR 3677, thiazovivin, HA1100 hydrochloride, HA1077 and GSK-429286.

E24. The cellular spheroid of embodiment E21, wherein the one or more cytoskeletal structure modulators are chosen from one or more PAK inhibitors.

E25. The cellular spheroid of embodiment E24, wherein one or more PAK inhibitors comprise IPA3.

E26. The cellular spheroid of embodiment E21, wherein the one or more cytoskeletal structure modulators are chosen from one or more myosin II inhibitors.

E27. The cellular spheroid of embodiment E26, wherein the one or more myosin II inhibitors comprise blebbistatin.

E28. The cellular spheroid of any one of embodiments E1 to E27, wherein the substrate attachment conditions comprise calcium at a concentration of at least 0.5 mM.

E28.1 The cellular spheroid of any one of embodiments E1 to E27, wherein the substrate attachment conditions comprise calcium at a concentration of at least 1 mM.

E29. The cellular spheroid of any one of embodiments E1 to E27, wherein the substrate attachment conditions comprise calcium at a concentration of at least 1.5 mM.

E30. The cellular spheroid of any one of embodiments E1 to E29, wherein the spheroid-inducing culture conditions comprise culturing the cell-substrate body in liquid suspension.

E31. The cellular spheroid of any one of embodiments E1 to E29, wherein the spheroid-inducing culture conditions comprise encapsulating the cell-substrate body in a hydrogel.

E32. The cellular spheroid of any one of embodiments E1 to E29, wherein the spheroid-inducing culture conditions comprise encapsulating the cell-substrate body in an extracellular matrix.

E33. The cellular spheroid of any one of embodiments E1 to E32, wherein the spheroid-inducing culture conditions are serum-free conditions.

E34. The cellular spheroid of any one of embodiments E1 to E33, wherein the spheroid-inducing culture conditions are feeder cell-free conditions.

E35. The cellular spheroid of any one of embodiments E1 to E34, wherein the spheroid-inducing culture conditions are defined conditions.

E36. The cellular spheroid of any one of embodiments E1 to E35, wherein the spheroid-inducing culture conditions are xeno-free conditions.

E37. The cellular spheroid of any one of embodiments E1 to E36, wherein the spheroid-inducing culture conditions comprise one or more transforming growth factor beta (TGF-beta) inhibitors.

E38. The cellular spheroid of any one of embodiments E1 to E37, wherein the spheroid-inducing culture conditions comprise one or more cytoskeletal structure modulators.

E39. The cellular spheroid of any one of embodiments E1 to E38, wherein the spheroid-inducing culture conditions comprise one or more transforming growth factor beta (TGF-beta) inhibitors and one or more cytoskeletal structure modulators.

E40. The cellular spheroid of any one of embodiments E37 to E39, wherein the one or more TGF-beta inhibitors comprise one or more ALK5 inhibitors.

E41. The cellular spheroid of embodiment E40, wherein the one or more ALK5 inhibitors are chosen from A83-01, GW788388, RepSox, and SB 431542.

E42. The cellular spheroid of any one of embodiments E39 to E41, wherein the one or more cytoskeletal structure modulators comprise one or more agents that disrupt cytoskeletal structure.

E43. The cellular spheroid of any one of embodiments E39 to E42, wherein the one or more cytoskeletal structure modulators are chosen from one or more of a Rho-associated protein kinase inhibitor, a p21-activated kinase (PAK) inhibitor, and a myosin II inhibitor.

E44. The cellular spheroid of embodiment E43, wherein the one or more cytoskeletal structure modulators are chosen from one or more Rho-associated protein kinase inhibitors.

E45. The cellular spheroid of embodiment E44, wherein the one or more Rho-associated protein kinase inhibitors are chosen from Y-27632, SR 3677, thiazovivin, HA1100 hydrochloride, HA1077 and GSK-429286.

E46. The cellular spheroid of embodiment E43, wherein the one or more cytoskeletal structure modulators are chosen from one or more PAK inhibitors.

E47. The cellular spheroid of embodiment E46, wherein one or more PAK inhibitors comprise IPA3.

E48. The cellular spheroid of embodiment E43, wherein the one or more cytoskeletal structure modulators are chosen from one or more myosin II inhibitors.

E49. The cellular spheroid of embodiment E48, wherein the one or more myosin II inhibitors comprise blebbistatin.

E50. The cellular spheroid of any one of embodiments E1 to E49, wherein the spheroid-inducing culture conditions comprise calcium at a concentration of at least 0.5 mM.

E50.1 The cellular spheroid of any one of embodiments E1 to E49, wherein the spheroid-inducing culture conditions comprise calcium at a concentration of at least 1 mM.

E51. The cellular spheroid of any one of embodiments E1 to E49, wherein the spheroid-inducing culture conditions comprise calcium at a concentration of at least 1.5 mM.

E52. The cellular spheroid of any one of embodiments E1 to E51, wherein the spheroid is solid.

E53. The method of any one of embodiments E1 to E51, wherein the spheroid is hollow.

E54. The cellular spheroid of embodiment E53, wherein the spheroid interior comprises a lumen.

E55. The cellular spheroid of any one of embodiments E1 to E54, wherein each of the epithelial cells in the spheroid comprises a lateral membrane.

E56. The cellular spheroid of embodiment E55, wherein the epithelial cells in the spheroid comprise intercellular tight junctions at the lateral membrane.

E57. The cellular spheroid of any one of embodiments E1 to E56, wherein the spheroid exterior comprises cilia and/or microvilli.

E58. The cellular spheroid of any one of embodiments E1 to E57, wherein the spheroid interior comprises one or more basement membrane components.

E59. The cellular spheroid of any one of embodiments E1 to E58, wherein the cellular spheroid is produced ex vivo.

E60. The cellular spheroid of any one of embodiments E1 to E59, wherein the cellular spheroid is an isolated cellular spheroid.

E61. The cellular spheroid of any one of embodiments E1 to E60, wherein the cellular spheroid is an artificial cellular assembly.

E62. The cellular spheroid of any one of embodiments E1 to E61, wherein the epithelial cells in (a) are non-primary cultured epithelial cells.

E63. The cellular spheroid of any one of embodiments E1 to E62, wherein the epithelial cells in (a) are ex-vivo expanded epithelial cells.

E64. The cellular spheroid of any one of embodiments E1 to E63, wherein the epithelial cells in (a) are isolated epithelial cells.

E65. The cellular spheroid of any one of embodiments E1 to E64, wherein the epithelial cells in (a) are genetically engineered epithelial cells.

E66. The cellular spheroid of any one of embodiments E1 to E65, wherein the epithelial cells comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

E67. The cellular spheroid of embodiment E66, wherein the epithelial cells comprise airway epithelial cells.

E68. The cellular spheroid of embodiment E66, wherein the epithelial cells comprise keratinocyte epithelial cells.

E69. The cellular spheroid of embodiment E66, wherein the epithelial cells comprise prostate epithelial cells.

E70. The cellular spheroid of embodiment E66, wherein the epithelial cells comprise mammary epithelial cells.

E71. The cellular spheroid of any one of embodiments E1 to E70, wherein the epithelial cells in (a) comprise primary epithelial cells.

E72. The cellular spheroid of any one of embodiments E1 to E71, wherein the epithelial cells in (a) comprise expanded primary epithelial cells.

E73. The cellular spheroid of any one of embodiments E1 to E72, wherein the epithelial cells in (a) comprise isolated primary epithelial cells.

E74. The cellular spheroid of any one of embodiments E1 to E73, wherein the epithelial cells in (a) comprise anchorage dependent epithelial cells.

E75. The cellular spheroid of any one of embodiments E1 to E74, wherein the method comprises, prior to (a), obtaining the epithelial cells from a subject.

E76. The cellular spheroid of embodiment E75, wherein the subject is a human.

E77. The cellular spheroid of any one of embodiments E1 to E76, wherein the method comprises, prior to (a), isolating the epithelial cells from tissue from a subject, thereby generating isolated epithelial cells.

E78. The cellular spheroid of embodiment E77, wherein the isolated epithelial cells comprise no extracellular components from the tissue from the subject.

F1. A population of cellular spheroids, wherein:
- each spheroid comprises an interior and an exterior;
- each spheroid comprises epithelial cells, wherein
  - the epithelial cells comprise primary epithelial cells;
  - each of the epithelial cells comprises an apical membrane and a basal membrane; and
  - for some or all of the epithelial cells in the spheroid, the basal membrane is in the spheroid interior and the apical membrane is on the spheroid exterior; and
- the population of cellular spheroids is a homogeneous population or a substantially homogeneous population.

F1.1 The population of cellular spheroids of embodiment F1, wherein the epithelial cells were obtained from a subject.

F1.2 The population of cellular spheroids of embodiment F2, wherein the subject is a human subject.

F2. The population of cellular spheroids of embodiment F1, F1.1 or F1.2, wherein each spheroid is solid.

F3. The population of cellular spheroids of embodiment F1, F1.1 or F1.2, wherein each spheroid is hollow.

F4. The population of cellular spheroids of embodiment F3, wherein each spheroid interior comprises a lumen.

F5. The population of cellular spheroids of any one of embodiments F1 to F4, wherein each of the epithelial cells comprises a lateral membrane.

F6. The population of cellular spheroids of embodiment F5, wherein the epithelial cells comprise intercellular junctions at the lateral membrane.

F7. The population of cellular spheroids of any one of embodiments F1 to F6, wherein each spheroid exterior comprises cilia and/or microvilli.

F8. The population of cellular spheroids of any one of embodiments F1 to F7, wherein each spheroid interior comprises one or more basement membrane components.

F9. The population of cellular spheroids of embodiment F8, wherein the one or more basement membrane components comprise one or more basement membrane proteins or fragments thereof.

F10. The population of cellular spheroids of embodiment F9, wherein the one or more basement membrane proteins comprise one or more of laminin, collagen, fibronectin, and nidogen.

F11. The population of cellular spheroids of embodiment F9, wherein the one or more basement membrane proteins comprise collagen IV.

F12. The population of cellular spheroids of embodiment F8, wherein the one or more basement membrane components comprise mimetic peptides.

F13. The population of cellular spheroids of embodiment F12, wherein the one or more basement membrane components comprise fibronectin-mimetic peptides and/or laminin-mimetic peptides.

F14. The population of cellular spheroids of any one of embodiments F8 to F13, wherein the one or more basement membrane components are produced by the epithelial cells.

F14.1 The population of cellular spheroids of any one of embodiments F8 to F14, wherein the one or more basement membrane components were not obtained from the subject.

F15. The population of cellular spheroids of any one of embodiments F8 to F13, wherein the epithelial cells are attached to a substrate.

F16. The population of cellular spheroids of embodiment F15, wherein the substrate is a microsphere.

F17. The population of cellular spheroids of embodiment F15, wherein the substrate is a microcarrier.

F18. The population of cellular spheroids of any one of embodiments F15 to F17, wherein the one or more basement membrane components are provided on the substrate.

F19. The population of cellular spheroids of any one of embodiments F1 to F18, wherein the spheroids are produced ex vivo.

F20. The population of cellular spheroids of any one of embodiments F1 to F19, wherein the spheroids are isolated spheroids.

F21. The population of cellular spheroids of any one of embodiments F1 to F20, wherein the cellular spheroids are artificial cellular assemblies.

F22. The population of cellular spheroids of any one of embodiments F1 to F21, wherein the epithelial cells comprise anchorage dependent epithelial cells.

F23. The population of cellular spheroids of any one of embodiments F1 to F22, wherein the epithelial cells are derived from ex-vivo expanded primary epithelial cells.

F24. The population of cellular spheroids of any one of embodiments F1 to F23, wherein the epithelial cells comprise isolated epithelial cells.

F25. The population of cellular spheroids of any one of embodiments F1 to F24, wherein the epithelial cells comprise one or more of prostate epithelial cells, mammary epithelial cells, hepatocytes, liver epithelial cells, biliary epithelial cells, gall bladder cells, pancreatic islet cells, pancreatic beta cells, pancreatic ductal epithelial cells, pulmonary epithelial cells, lung epithelial cells, airway epithelial cells, nasal epithelial cells, tracheal epithelial cells, bronchial epithelial cells, kidney epithelial cells, bladder epithelial cells, urethral epithelial cells, stomach epithelial cells, esophageal epithelial cells, large intestinal epithelial cells, small intestinal epithelial cells, testicular epithelial cells, ovarian epithelial cells, fallopian tube epithelial cells, thyroid epithelial cells, parathyroid epithelial cells, adrenal epithelial cells, thymus epithelial cells, pituitary epithelial cells, glandular epithelial cells, amniotic epithelial cells, retinal pigmented epithelial cells, sweat gland epithelial cells, sebaceous epithelial cells, hair follicle epithelial cells, keratinocyte epithelial cells, dermal keratinocytes, ocular epithelial cells, corneal epithelial cells, oral mucosal epithelial cells, and cervical epithelial cells.

F26. The population of cellular spheroids of embodiment F25, wherein the epithelial cells comprise airway epithelial cells.

F27. The population of cellular spheroids of embodiment F25, wherein the epithelial cells comprise keratinocyte epithelial cells.

F28. The population of cellular spheroids of embodiment F25, wherein the epithelial cells comprise prostate epithelial cells.

F29. The population of cellular spheroids of embodiment F25, wherein the epithelial cells comprise mammary epithelial cells.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms “comprising,” “consisting essentially of,” and “consisting of” may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term “a” or “an” can refer to one of or a plurality of the elements it modifies (e.g., “a reagent” can mean one or more reagents) unless it is contextually clear either one of the elements or more than one of the elements is described. The term “about” as used herein refers to a value within 10% of the underlying parameter (i.e., plus or minus 10%), and use of the term “about” at the beginning of a string of values modifies each of the values (i.e., “about 1, 2 and 3” refers to about 1, about 2 and about 3). For example, a weight of “about 100 grams” can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for producing a cellular spheroid comprising:

(a) aggregating a plurality of primary epithelial cells in an aggregation well, an aggregation container, or in a hanging drop under serum-free aggregation conditions, thereby forming a cellular aggregate, wherein the aggregation well or the aggregation container is a conical shaped well or tube, a round bottom well or tube, or an inverse pyramid-shaped well or tube, and wherein the aggregation conditions comprise one or more transforming growth factor beta (TGF-beta) inhibitors; and (b) transferring the cellular aggregate from step (a) into a new culture vessel or culture environment; and (c) culturing the cellular aggregate under non-adherent and serum-free spheroid-inducing culture conditions, thereby generating a cellular spheroid wherein:

(i) the spheroid comprises an interior and an exterior, wherein a basal side is in the spheroid interior and an apical side is on the spheroid exterior, and (iii) the spheroid-inducing culture conditions comprise (1) one or more TGF-beta inhibitors, or (2) one or more cytoskeletal structure modulators chosen from one or more of a Rho-associated protein kinase inhibitor, a p21-activate kinase (PAK) inhibitor, and a myosin II inhibitor, or both (1) and (2).

2. The method of claim 1, wherein the aggregation conditions further comprise one or more cytoskeletal structure modulators chosen from one or more of a Rho-associated protein kinase inhibitor, a p21-activated kinase (PAK) inhibitor, and a myosin II inhibitor.

3. The method of claim 2, wherein the one or more TGF-beta inhibitors comprise one or more ALK5, ALK4, and/or ALK7 inhibitors.

4. The method of claim 3, wherein the one or more ALK5, ALK4, and/or ALK7 inhibitors are chosen from A83-01, GW788388, RepSox, and SB 431542.

5. The method of claim 2, wherein the one or more Rho-associated protein kinase inhibitors are chosen from Y-27632, SR 3677, thiazovivin, HA1100 hydrochloride, HA1077 and GSK-429286; the one or more PAK inhibitors comprise IPA3; and the one or more myosin II inhibitors comprise blebbistatin.

6. The method of claim 1, wherein the aggregation conditions, the spheroid-inducing culture conditions, or the aggregation conditions and the spheroid-inducing culture conditions comprise calcium at a concentration of at least 0.5 mM, at least 1 mM, or at least 1.5 mM.

7. The method of claim 1, wherein the spheroid-inducing culture conditions comprise culturing the cellular aggregate in liquid suspension, encapsulating the cellular aggregate in a hydrogel, or encapsulating the cellular aggregate in an extracellular matrix.

8. The method of claim 1, wherein the aggregation conditions, the spheroid-inducing culture conditions, or the aggregation conditions and the spheroid-inducing culture conditions are bovine pituitary extract (BPE)-free conditions.

9. The method of claim 1, wherein the aggregation, the spheroid-inducing culture conditions, or the substrate attachment conditions and the spheroid-inducing culture conditions are feeder cell-free conditions.

10. The method of claim 1, wherein the aggregation conditions, the spheroid-inducing culture conditions, or the substrate attachment conditions and the spheroid-inducing culture conditions comprise defined culture media.

11. The method of claim 1, wherein the aggregation conditions, the spheroid-inducing culture conditions, or the substrate attachment conditions and the spheroid-inducing culture conditions are xeno-free conditions.

* * * * *